(12) United States Patent
Sciavolino et al.

(10) Patent No.: US 11,135,298 B2
(45) Date of Patent: *Oct. 5, 2021

(54) COMPOSITIONS AND METHODS RELATING TO SALTS OF SPECIALIZED PRO-RESOLVING MEDIATORS

(71) Applicant: Thetis Pharmaceuticals LLC, Branford, CT (US)

(72) Inventors: Frank C. Sciavolino, Waterford, CT (US); Gary Mathias, Ridgefield, CT (US); Michael C. Van Zandt, Guilford, CT (US); Gunnar Erik Jagdmann, Jr., Branford, CT (US); Jessica J. Dworak, Middletown, CT (US)

(73) Assignee: Thetis Pharmaceuticals LLC, Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/535,754

(22) Filed: Aug. 8, 2019

(65) Prior Publication Data

US 2020/0179521 A1    Jun. 11, 2020

Related U.S. Application Data

(63) Continuation of application No. 15/824,606, filed on Nov. 28, 2017, now Pat. No. 10,420,843, which is a continuation-in-part of application No. 15/535,936, filed as application No. PCT/US2017/035752 on Jun. 2, 2017, now Pat. No. 10,130,719.

(60) Provisional application No. 62/345,043, filed on Jun. 3, 2016.

(51) Int. Cl.
| | |
|---|---|
| *A61K 47/54* | (2017.01) |
| *A61K 47/62* | (2017.01) |
| *C07C 59/42* | (2006.01) |
| *C07C 229/26* | (2006.01) |
| *C07C 237/12* | (2006.01) |
| *C07C 237/22* | (2006.01) |
| *A61P 1/06* | (2006.01) |
| *A61P 1/12* | (2006.01) |
| *A61P 29/00* | (2006.01) |
| *A61P 1/04* | (2006.01) |
| *A61K 31/202* | (2006.01) |
| *A61K 31/232* | (2006.01) |
| *A61K 38/03* | (2006.01) |
| *A61K 45/06* | (2006.01) |
| *A61P 1/00* | (2006.01) |

(52) U.S. Cl.
CPC ......... *A61K 47/541* (2017.08); *A61K 31/202* (2013.01); *A61K 31/232* (2013.01); *A61K 38/03* (2013.01); *A61K 45/06* (2013.01); *A61K 47/62* (2017.08); *A61P 1/00* (2018.01); *A61P 1/04* (2018.01); *A61P 1/06* (2018.01); *A61P 1/12* (2018.01); *A61P 29/00* (2018.01); *C07C 59/42* (2013.01); *C07C 229/26* (2013.01); *C07C 237/12* (2013.01); *C07C 237/22* (2013.01); *A61K 2800/00* (2013.01)

(58) Field of Classification Search
CPC .... A61K 47/541; C07C 59/42; C07C 229/26; C07C 59/00
USPC ......................................................... 514/560
See application file for complete search history.

(56) References Cited

U.S. PATENT DOCUMENTS

| | | |
|---|---|---|
| 4,599,152 A | 7/1986 | Ashmead |
| 4,804,539 A | 2/1989 | Guo et al. |
| 4,863,898 A | 9/1989 | Ashmead |
| 4,883,658 A | 11/1989 | Holly |
| 4,914,088 A | 4/1990 | Glonek et al. |
| 5,061,815 A | 10/1991 | Leu |
| 5,075,104 A | 12/1991 | Gressel et al. |
| 5,278,151 A | 1/1994 | Korb et al. |
| 5,294,607 A | 3/1994 | Glonek et al. |
| 5,371,108 A | 12/1994 | Korb et al. |
| 5,441,951 A | 8/1995 | Serhan |
| 5,578,586 A | 11/1996 | Glonek et al. |
| 5,648,512 A | 7/1997 | Serhan |
| 5,795,909 A | 8/1998 | Shashoua et al. |

(Continued)

FOREIGN PATENT DOCUMENTS

| | | |
|---|---|---|
| AU | 2012227298 A1 | 4/2014 |
| CN | 103340300 A | 10/2013 |

(Continued)

OTHER PUBLICATIONS

Cayman Chemical, Product Information Resolvin E1, 2019, recovered from https://www.caymanchem.com/pdfs/10007848.pdf on Jan. 25, 2021, pp. 1-2. (Year: 2019).*

(Continued)

*Primary Examiner* — Ana Z Muresan

(74) *Attorney, Agent, or Firm* — Munel Liberto, Esq.; Mintz Levin Cohn Ferris Glovsky and Popeo, P.C.

(57) ABSTRACT

The present invention relates to compounds of Formulas I-IV and compositions comprising same, including pharmaceutical compositions. The compounds of Formulas I-IV represent new salt forms of specialized pro-resolving mediators ("SPMs") which include lipoxins, resolvins, protectins, and their aspirin-triggered counterparts. The SPM salts described here contain at least one or two SPM molecules ionically bound to at least one basic function that is provided by a scaffold as described in Formulas I-IV. Also provided are methods for pharmaceutical and non-pharmaceutical uses of such compounds and compositions describing same.

33 Claims, 8 Drawing Sheets

(56) References Cited

U.S. PATENT DOCUMENTS

| | | | |
|---|---|---|---|
| 6,048,897 A | 4/2000 | Serhan | |
| 6,316,648 B1 | 11/2001 | Serhan | |
| 6,372,790 B1 | 4/2002 | Bonhomme et al. | |
| 6,491,950 B1 | 12/2002 | Gutierrez-Rocca et al. | |
| 6,517,870 B1 | 2/2003 | Nishii et al. | |
| 6,569,075 B2 | 5/2003 | Serhan | |
| 6,602,902 B2 | 8/2003 | Shashoua et al. | |
| 6,627,658 B2 | 9/2003 | Serhan et al. | |
| 6,667,064 B2 | 12/2003 | Surette | |
| 6,670,396 B2 | 12/2003 | Serhan et al. | |
| 6,720,001 B2 | 4/2004 | Chen et al. | |
| 6,881,854 B2 | 4/2005 | Ptock et al. | |
| 6,887,901 B1 | 5/2005 | Serhan | |
| 6,893,627 B2 | 5/2005 | Ribnicky et al. | |
| 7,053,230 B2 | 5/2006 | Serhan et al. | |
| 7,105,572 B2 | 9/2006 | Sato | |
| 7,195,914 B2 | 3/2007 | Surette | |
| 7,199,151 B2 | 4/2007 | Shashoua et al. | |
| 7,214,387 B2 | 5/2007 | Sanghvi et al. | |
| 7,223,770 B2 | 5/2007 | Zhang et al. | |
| 7,288,569 B2 | 10/2007 | Serhan | |
| 7,294,728 B2 | 11/2007 | Serhan | |
| 7,304,089 B2 | 12/2007 | Kramer et al. | |
| 7,378,444 B2 | 5/2008 | Goodman et al. | |
| 7,429,395 B2 | 9/2008 | Campbell-Tofte | |
| 7,547,454 B2 * | 6/2009 | Gupta | A61K 8/19 424/642 |
| 7,553,870 B2 | 6/2009 | Shibuya | |
| 7,579,025 B2 | 8/2009 | Campbell-Tofte | |
| 7,595,341 B2 | 9/2009 | Goodman et al. | |
| 7,619,002 B2 | 11/2009 | Shibuya | |
| 7,666,898 B2 | 2/2010 | Chang et al. | |
| 7,670,612 B2 | 3/2010 | Miller | |
| 7,709,669 B2 | 5/2010 | Serhan et al. | |
| 7,737,178 B2 | 6/2010 | Serhan et al. | |
| 7,741,369 B2 | 6/2010 | Serhan | |
| 7,973,073 B2 | 7/2011 | Mylari et al. | |
| 8,008,282 B2 | 8/2011 | Serhan et al. | |
| 8,034,842 B2 | 10/2011 | Bryhn et al. | |
| 8,058,312 B2 | 11/2011 | Kim et al. | |
| 8,076,377 B2 | 12/2011 | Kim et al. | |
| 8,119,691 B2 | 2/2012 | Serhan et al. | |
| 8,178,707 B2 | 5/2012 | Gleason et al. | |
| 8,349,896 B2 | 1/2013 | Serhan et al. | |
| 8,378,131 B2 | 2/2013 | Gleason et al. | |
| 8,642,073 B2 | 2/2014 | Mannino et al. | |
| 8,710,041 B2 | 4/2014 | Osterloh et al. | |
| 8,765,811 B2 | 7/2014 | Mylari et al. | |
| 8,906,964 B2 | 12/2014 | Bobotas et al. | |
| 8,933,124 B2 | 1/2015 | Mylari et al. | |
| 9,012,501 B2 | 4/2015 | Sachetto et al. | |
| 9,242,008 B2 | 1/2016 | Sciavolino et al. | |
| 9,394,318 B2 | 7/2016 | Lewis | |
| 9,505,709 B2 | 11/2016 | Mathias et al. | |
| 9,999,626 B2 | 6/2018 | Sciavolino et al. | |
| 10,130,719 B2 | 11/2018 | Sciavolino et al. | |
| 10,420,843 B2 * | 9/2019 | Sciavolino | A61K 31/232 |
| 2003/0077335 A1 | 4/2003 | Richardson et al. | |
| 2003/0220301 A1 | 11/2003 | Lal et al. | |
| 2005/0158374 A1 | 7/2005 | Wong et al. | |
| 2005/0165102 A1 | 7/2005 | Wong et al. | |
| 2005/0182029 A1 | 8/2005 | Lal | |
| 2005/0182089 A1 | 8/2005 | Friedl et al. | |
| 2006/0159746 A1 | 7/2006 | Troup et al. | |
| 2006/0229359 A1 | 10/2006 | Zhang et al. | |
| 2006/0240095 A1 | 10/2006 | Junien et al. | |
| 2006/0293288 A1 | 12/2006 | Serhan et al. | |
| 2007/0009246 A1 | 1/2007 | Lee | |
| 2007/0060532 A1 | 3/2007 | Junien et al. | |
| 2007/0092461 A1 | 4/2007 | Gupta | |
| 2007/0207196 A1 | 9/2007 | Zhang | |
| 2008/0045559 A1 | 2/2008 | Zhang et al. | |
| 2008/0200533 A1 | 8/2008 | Krishnan | |
| 2008/0260819 A1 | 10/2008 | Fleming et al. | |
| 2009/0047340 A1 | 2/2009 | Guilford | |
| 2009/0054513 A1 | 2/2009 | Webster et al. | |
| 2009/0156612 A1 | 6/2009 | Kuroita et al. | |
| 2009/0227560 A1 | 9/2009 | Kuroita et al. | |
| 2010/0035990 A1 | 2/2010 | Bryhn et al. | |
| 2010/0105773 A1 | 4/2010 | Smith et al. | |
| 2010/0121048 A1 | 5/2010 | Kuroita et al. | |
| 2010/0137587 A1 | 6/2010 | Takanobu et al. | |
| 2010/0324010 A1 | 12/2010 | Imaeda et al. | |
| 2011/0046053 A1 | 2/2011 | Kidron | |
| 2011/0052678 A1 | 3/2011 | Shantha et al. | |
| 2011/0171142 A1 | 7/2011 | Lara | |
| 2011/0237813 A1 | 9/2011 | Gleason et al. | |
| 2012/0178813 A1 | 7/2012 | Mylari et al. | |
| 2012/0189569 A1 | 7/2012 | Gupta | |
| 2012/0245229 A1 | 9/2012 | Ji et al. | |
| 2012/0258087 A1 | 10/2012 | Jedlinski et al. | |
| 2013/0095140 A1 | 4/2013 | Baron et al. | |
| 2013/0281535 A1 | 10/2013 | Mylari et al. | |
| 2013/0281536 A1 | 10/2013 | Pinchera et al. | |
| 2014/0100273 A1 | 4/2014 | Bobotas et al. | |
| 2014/0107360 A1 | 4/2014 | Mylari et al. | |
| 2014/0118419 A1 | 5/2014 | Wu et al. | |
| 2014/0249221 A1 | 9/2014 | Mylari et al. | |
| 2015/0126602 A1 | 5/2015 | Bannenberg et al. | |
| 2015/0366980 A1 | 12/2015 | Sciavolino et al. | |
| 2016/0199385 A1 | 7/2016 | Sciavolino et al. | |
| 2018/0110751 A1 | 4/2018 | Sciavolino et al. | |
| 2018/0200375 A1 | 7/2018 | Sciavolino et al. | |
| 2021/0138072 A1 | 5/2021 | Sciavolino et al. | |

FOREIGN PATENT DOCUMENTS

| | | | |
|---|---|---|---|
| CN | 104430341 A | 3/2015 | |
| EP | 2705844 A1 | 3/2014 | |
| JP | H09508619 A | 9/1997 | |
| JP | 2000191416 A | 7/2000 | |
| JP | 2000212145 A | 8/2000 | |
| JP | 2004175790 A | 6/2004 | |
| WO | 95/16661 A1 | 6/1995 | |
| WO | 2003068209 A1 | 8/2003 | |
| WO | 2003093449 A2 | 11/2003 | |
| WO | 2003093449 A3 | 11/2003 | |
| WO | 2004028469 A2 | 4/2004 | |
| WO | 2004082402 A2 | 9/2004 | |
| WO | 2005041923 A1 | 5/2005 | |
| WO | 2005042539 A1 | 5/2005 | |
| WO | WO-2005089744 A2 * | 9/2005 | A61K 31/445 |
| WO | 2005118612 A1 | 12/2005 | |
| WO | 2007041440 A2 | 4/2007 | |
| WO | 2007041440 A3 | 4/2007 | |
| WO | 2008022807 A2 | 2/2008 | |
| WO | 2008022807 A3 | 2/2008 | |
| WO | 2008068041 A1 | 6/2008 | |
| WO | 2009038396 A2 | 3/2009 | |
| WO | 201012799 A2 | 2/2010 | |
| WO | 2010127099 A2 | 11/2010 | |
| WO | 2013103902 A1 | 7/2013 | |
| WO | 2014011814 A1 | 1/2014 | |
| WO | 2014011895 A2 | 1/2014 | |
| WO | 2014011895 A3 | 1/2014 | |
| WO | 2015171516 A1 | 11/2015 | |
| WO | 2015195491 A1 | 12/2015 | |
| WO | 2017041094 A1 | 3/2017 | |
| WO | 2017102703 A1 | 6/2017 | |
| WO | 2017210604 A1 | 12/2017 | |
| WO | 2019/108605 A1 | 6/2019 | |

OTHER PUBLICATIONS

International Search Report and Written Opinion dated Feb. 19, 2019 for International Application No. PCT/US2018/062784, filed Nov. 28, 2018 (15 pages).

Alagha, A. et al. (2011). "The preparation and crystal structure of acetatobis(L-arginine)zinc(II) acetate trihydrate, the first reported x-ray structure of a zinc(II)-arginine complex," Inorganica Chimica Acta 377(1):185-187.

Amino Acid Structures. Web. Nov. 14, 2013. http://www.cem.msu.edu/-cem 252/sp97/ch24/ch24aa/html.

(56) References Cited

OTHER PUBLICATIONS

Arita, M. et al. (Aug. 11, 2006). "Metabolic Inactivation of Resolvin E1 and Stabilization of Its Anti-Inflammatory Actions." Journal of Biological Chemistry 281 (32), 22847-54.

Brown, N. (2015). "Novel synthetic routes towards the anti-inflammatory mediator resolvin E1, and methodology development." (Thesis, Loughborough University. 195 pages.

Calder, P. (Nov. 2012). "Mechanisms of action of (n-3) fatty acids." The Journal of Nutrition 142:592S-599S. Doi: 103945/jn.111.155259. 8 pages.

Charles, M. et al. (2000). "Treatment with Metformin of Non-Diabetic Men with Hypertension, Hypertriglyceridaemia and Central Fat Distribution: The BIGPRO 1.2 Trial." Diabetes Metabolic Research Reviews 16:2-7.

Cold Spring Harbor Protocols. 2006. Web. Nov. 13, 2013. http://cshprotocols.cship.org.

Dalli, J. "Novel n-3 immunoresolvents: structures and actions." Jun. 2013. Scientific Reports 3:1940 Doi: 10.1038/srep01940. 13 pages.

Dudev, T. et al., "Competitive binding in magnesium coordination chemistry: water versus ligands of biological interest." 1999. Journal of the American Chemical Society 121:7665-7673.

Dyall, S. (Apr. 2015). "Long-chain omega-3 fatty acids and the brain: a review of the independent and shared effects of EPA, DPA, and DHA." Frontiers in Aging Science vol. 7, article 52. Doi: 10.3389/fnagi.2015.00052. 15 pages.

Eicosapentaenoic Acid pKa (Nov. 14, 2013). STN Registry File. Web.

Farrukh, A. et al. (Jul. 16, 2014). "Is there a role for fish oil in inflammatory bowel disease?", World J. Clin. Cases, 2(7), pp. 250-252.

Goldberg, R. et al. (Aug. 26, 2013). "Lifestyle and Metformin Treatment Favorably Influence Lipoprotein Subfraction Distribution in the Diabetes Prevention Program." Journal of Clinical Endocrinology Metabolism epub. ahead of print Aug. 26, 2013.

Hartwell, I. et al. (Mar. 1970). "Preparation and Characterization of Tyrosine and Lysine Metal Chelate Polyesters and Polyamides," Journal of the American Chemical Society 92(5):1284-1289.

International Search Report issued in PCT/US2013/049984 dated Nov. 28, 2013. 6 pages.

International Search Report dated Sep. 16, 2015, for PCT Application No. PCT/US2015/035686, filed Jun. 12, 2015, 6 pages.

International Search Report dated Sep. 6, 2017, for PCT Application No. PCT/US2017/035752, filed Jun. 2, 2017, 7 pages.

Lim, Y. et al., (2015). "Biological roles of resolvins and related substances in the resolution of pain." BioMed Research International, Article ID 830930. http://dx.doi.org/10.1155/2015/830930. 14 pages.

Lombardo, D. (Jan. 13, 2015). "Synthesis of a benzene-annulated analogue of resolvin E1 and other lipid mediators." Ph.D. Thesis, Curtin University, Perth, AU, XP055627963.

Maclean, C. (2005). et al., "Systematic review of the effects of n3 fatty acids in inflammatory bowel disease" American Journal of Clinical Nutrition, 82(3), pp. 611-619.

Maddipati, K. et al. (Jan. 4, 2011). "Stability and analysis of eicosanoids and docosanoids in tissue culture media." Prostaglandins and Other Lipid Mediators 94(1):59-72.

Ogawa, N. (Nov. 4, 2009). "Total synthesis of resolvin E1." Tetrahedron Letters 50(44):6079-6082.

Oh, S. et al. (Feb. 2011). "Pro-resolving actions and stereoselective biosynthesis of 18S E-series resolvins in human leukocytes and murine inflammation." Journal of Clinical Investigation 121(2):569-581. http://dx.doi.org/10.1172/JCI42545.

Piazzi, G. et al., (2014). "Eicosapentaenoic acid free fatty acid prevents and suppresses colonic neoplasia in colitis-associated colorectal cancer acting on Notch signaling and gut microbiota", Nov. 2014, International Journal of Cancer, 135(9), pp. 2004-2013.

Prandimet. RxList. Web. Nov. 14, 2013. http://www.rxlist.com/prandimet-drug.htm.

Scifinder search result of substances in US 2012/0258087 A1 (accessed on Mar. 1, 2017).

Serhan, C. et al., (Oct. 9, 2015). "Lipid mediators in the resolution of inflammation." Cold Spring Harbor Perspectives in Biology; 7:a016311. 21 pages.

Serhan, C. (Jun. 2014). "Novel pro-resolving lipid mediators in inflammation are leads for resolution physiology." Nature 510(7503): 92-101. Doi: 10.1038/nature13479.

Serhan, C.(Apr. 2012). "Infection regulates pro-resolving mediators that lower antibiotic requirements." Apr. 2012. Nature vol. 484 doi: 10.1038/nature11042. 31 pages.

Sugiyama et al.(2008). "Eicosapentaenoic Acid Lowers Plasma and Liver Cholesterol Levels in the Presence of Peroxisome Profferators-Activate Receptor Alpha." Life Sciences. 83:19-28.

Tucker, S. (Mar. 2013). "Emerging targets in lipid-based therapy." Biochemical Pharmacology vol. 85(5):673-688. Doi: 10.1016/j.bcp.2012.11.028. 16 pages.

Winkler, J. (Jan., 2011). "Resolvin D4 stereoassignment and its novel actions in host protection and bacterial clearance." Scientific Reports 6:18972, Doi:10.1038/srep18972. 11 pages.

Written Opinion dated Sep. 16, 2015, for PCT Application No. PCT/US2015/035686, filed Jun. 12, 2015, 13 pages.

Written Opinion dated Sep. 6, 2017, for PCT Application No. PCT/US2017/035752, filed Jun. 2, 2017, 8 pages.

Wulffele, M. et al. (2004). "The Effect of Metformin on Blood Pressure, Plasma Cholesterol and Triglycerides in Type 2 Diabetes Mellitus: A Systematic Review." Journal of Internal Medicine 256(1):1-14.

Yin, L-H. et al., (Oct. 2016). "Structural characterization of calcium glycinate, magnesium glycinate and zinc glycinate." Journal of Innovative Optical Health Sciences 10(3):1650052-1-1650052-10. 10 pages.

Ishida et al. (Jan. 2010) "Resolvin E1, An Endogenous Lipid Mediator Derived from Eicosapentaenoic Acid, Prevents Dextran Sulfate Sodium Induced Colitis", Inflammatory Bowel Disease, 16(1):87-95 (13 pages).

Kose et al. (2014) "Synthesis, Spectral, Thermal Studies of Co(II), Ni(II), Cu(II) and Zn(II)-arginato Complexes. Crystal Structure of Monoaquabis(arginato-KO,KN)copper(II). [Cu(arg)2(H2O)]. NaNO3", Journal of the Chinese Chemical Society, 61(8):881-890.

Kydynov et al. (1990) "Thermal Stability of Lysine Complexes of Transition-Metal Chlorides, Sulfates", Khimiko-Tekhnologicheskiei Biologicheskie Nauki, 3:05 pages.

Laroui et al. (2012) "Dextran Sodium Sulfate (DSS) Induces Colitis in Mice by Forming Nano-Lipocomplexes with Medium-Chain-Length Fatty Acids in the Colon", PLoS One, 7(3):12 pages.

Li et al. (2013) "Total Synthesis of the Endogenous Inflammation Resolving Lipid Resolvin D2 Using a Common Lynchpin", Beilstein Journal of Organic Chemistry, 9:2762-2766.

Morin et al. (May 15, 2016) "MAG-EPA Reduces Severity of DSS-Induced Colitis in Rats", American Journal of Physiology Gastrointestinal and Liver Physiology, 310(10):G808-G821.

Rashid et al. (Feb. 2008) "Topical Omega-3 and Omega-6 Fatty Acids for Treatment of Dry Eye", Archives of Ophthalmology, 126(2):219-225.

Stevenson et al. (Jan. 2012) "Dry Eye Disease: An Immune-mediated Ocular Surface Disorder", Archives of Ophthalmology, 130(1):90-100.

Vasku et al. (Dec. 1986) "Comparative Study on Myocardial Damage in Irradiated for a Long Time and Nonirradiated Rats After Administration of FCOL", Strahlentherapie and Onkologie, 162(12):798-805.

Weiming et al. (Dec. 2001) "Theoretical study of the structure of a zinc complex of L-lysine", Journal of Molecular Science. 17(4):247-250. (English Abstract Sumitted).

Wei-Ming et al. (Jun. 2000) "The Research on Zinc Coordination No. 5 Odd Structure in Zinc Complex with L-Lysine", Journal of Molecular Science, 16(2):114-117. (English Abstract Sumitted).

Xianxian et al. (Apr. 2012) "Research of Synthesis Process for new Type Laminine Antihypertensives", Journal of Chemical Industry & Engineering. 33(2):38-40. (English Abstract Sumitted).

\* cited by examiner

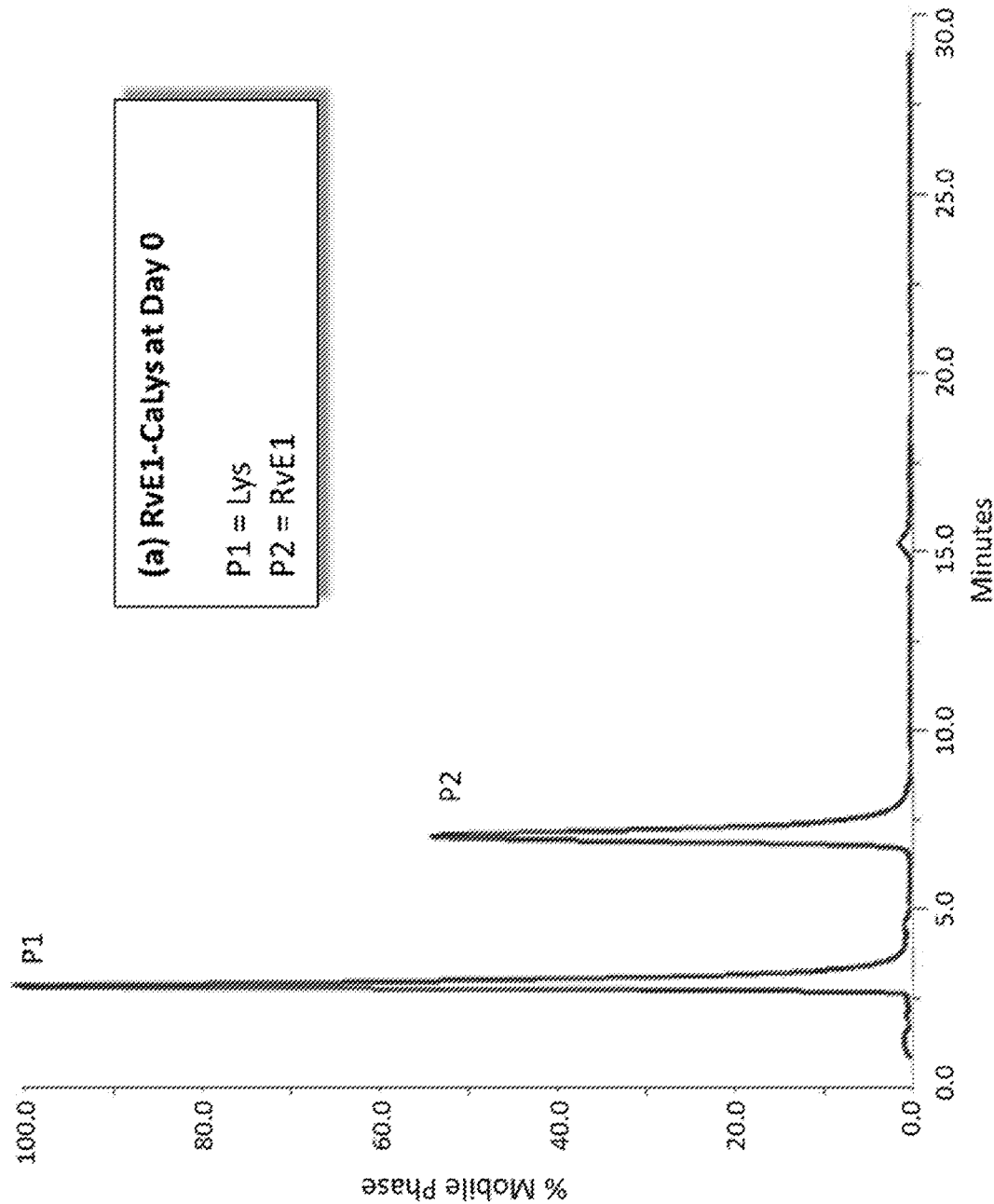

COMPOSITIONS AND METHODS RELATING TO SALTS OF SPECIALIZED PRO-RESOLVING MEDIATORS

CROSS-REFERENCE TO RELATED APPLICATIONS

This application in a continuation of U.S. patent application Ser. No. 15/824,606, filed on Nov. 28, 2017, issued as U.S. Pat. No. 10,420,843, which is a continuation in part of U.S. Ser. No. 15/535,936, filed Jun. 14, 2017, issued as U.S. Pat. No. 10,130,719, which is a national stage entry, filed under 35 U.S.C. § 371, of International Application No. PCT/US2017/035752, filed on Jun. 2, 2017, which claims the benefit of priority from U.S. Provisional Application Ser. No. 62/345,043, filed on Jun. 3, 2016, the contents of which are incorporated herein by reference in their entirety.

FIELD OF THE INVENTION

The present invention relates to new chemical entities which are salt forms of lipid molecules, and their use.

BACKGROUND OF THE INVENTION

The inflammatory response in animal tissues has two phases, initiation and resolution. At the cellular level, initiation is characterized by edema and the accumulation of immune cells such as neutrophils, monocytes, and macrophages. The initiation phase of the inflammatory response has long been recognized as an active process driven by metabolites of arachidonic acid such as the prostaglandins $PGE_2$ and $PGD_2$, which are chemo-attractants for eosinophils, neutrophils and monocytes, and the leukotrienes, especially $LTB_4$ which elicit adhesion, chemotaxis, and aggregation of leukocytes. In order for the inflamed tissue to return to a healthy state, the excess inflammatory cells, cellular debris, and other remnants of the host defense and any invading microorganisms must be cleared. This 'resolution' phase of the inflammatory response was for many years believed to be a passive process, the result of the dilution of the chemo-attractants of the initiation phase. Today, resolution of inflammation is recognized as an active process, driven by various molecules. For example, protectins and resolvins are autacoids produced locally at the site of inflammation. They assist in resolving inflammation by recruiting non-inflammatory monocytes which differentiate into macrophages that can remove excess neutrophils and cellular debris. These molecules are part of a class of 'specialized pro-resolving mediators' ("SPMs") of inflammation. Other SPMs include lipoxins, aspirin-triggered resolvins and aspirin-triggered protectins. See Serhan et al., "Lipid Mediators of Inflammation", *Cold Spring Harb Perspect Biol* 2015; 7:a016311.

Excessive inflammation is widely recognized as a unifying component in many chronic diseases including vascular diseases, metabolic diseases, and neurological diseases. See e.g., Serhan, C. N., *Nature* 2014 510:92-101. Accordingly, the ability to resolve excessive inflammation is of importance to human and animal health.

Researchers have established a role for various SPMs in numerous disease models, including those relating to Alzheimer's disease, burn wounds, chronic pancreatitis, diabetic wounds, dermatitis, pulmonary inflammation, peripheral nerve injury, obesity, allergic airway response, amyotrophic lateral sclerosis, acute lung injury, fibrosis, bacterial infection, peritonitis, dry eye, tissue regeneration, pain, adipose tissue inflammation, localized aggressive periodontitis, colitis, temporomandibular joint inflammation, arthritis, postoperative pain, postsurgical cognitive decline, endotoxin shock, HSV-keratitis, allograft rejection, heart ischemia, bacterial pneumonia, cigarette smoke-induced lung inflammation, vascular inflammation, fibromyalgia, and vagotomy. See e.g., Serhan et al., "Lipid Mediators of Inflammation", *Cold Spring Harb Perspect Biol* 2015; 7:a016311. U.S. Pat. Nos. 8,008,282 and 6,627,658 describe lipoxin analogs and their use as inhibitors of angiogenesis. U.S. Pat. Nos. 5,441,951, 5,648,512, 6,048,897, 6,316,648, 6,569,075, 6,887,901, 7,288,569, and 7,294,728, 7,741,369, and 7,741,369 describe lipoxin compounds and their use in treating cell proliferative disorders. U.S. Pat. No. 8,119,691 describes lipoxins and aspirin triggered lipoxins and their analogs in the treatment of asthma and inflammatory airway disease.

US 20060293288 describes the use of resolvins to treat gastrointestinal inflammation and diseases such as ulcerative colitis, Crohn's disease, infectious enteritis, antibiotic associative diarrhea, *Clostridium difficile* colitis, microscopic or lymphocytic colitis, collagenous colitis, colon polyps, familial polyps, familial polyposis syndrome, Gardner's Syndrome, *Helicobacter pylori*, irritable bowel syndrome, non-specific diarrheal illnesses, and intestinal cancers.

U.S. Pat. Nos. 6,670,396, 7,053,230, 7,709,669, 7,737,178, and 8,349,896 describe aspirin triggered lipid mediators and their use in methods for treating inflammation, for example where the inflammation manifests as Crohn's disease, ulcerative colitis, distal proctitis, rheumatoid spondylitis, arthritis, rheumatoid arthritis, osteoarthritis, gouty arthritis, psoriasis, dermatitis, eczematous dermatitis, atopic or seborrheic dermatitis, allergic or irritant contact dermatitis, eczema craquelee, photoallergic dermatitis, phototoxic dermatitis, phytophotodermatitis, radiation dermatitis, stasis dermatitis, arterial inflammation, coronary infarct damage, restenosis, uveitis, iritis, conjunctivitis, adult respiratory distress syndrome, bronchitis, cystic fibrosis, a spasmogenic condition, asthma, idiopathic bronchial asthma, arterial smooth muscle constriction, coronary spasm, myocardial infarction, ischemia-induced myocardial injury, cerebral spasm, stroke, inflammatory bowel disorder, spastic colon, mucous colitis, an allergic condition, eczema, an allergic bowel disease, coeliac disease, an allergic eye condition, hay fever, allergic rhinitis, allergic conjunctivitis, a condition involving blood platelet aggregation, coronary thrombosis, phlebitis, or phlebothrombosis, and methods of treating cardiovascular disease.

US 20120245229 describes methods of treating neuropathic pain, including pain associated with diabetic neuropathy or HIV infection, methods of treating post-operative pain, inflammatory pain, pain associated with cancer, and pain associated with fibromyalgia, by administering resolvins.

Lim et al. describes the analgesic potency of SPMs in a large number of inflammatory pain models and characterizes resolvins and related substances as therapeutic candidates for preventing deterioration of inflammation and pathologic pain. See Lim et al. "Biological Roles of Resolvins and Related Substances in the Resolution of Pain" *BioMed Research International* 2015, pp. 1-14, Article ID 830930. Lin also notes that "the powerful potencies" and "negligible adverse effects" of these molecules make them attractive candidates agents for clinical use.

US 20150126602 describes oils with anti-inflammatory activity containing natural specialized proresolving mediators and their precursors, such as 18HEPE and 17HDHA, and methods of using same for treating an inflammatory condition such as cardiovascular disease (including atherosclerosis, high blood pressure, hypercholesterolemia, hypertriglyceridemia, endothelial hyporeactivity, cardiac infarction and cerebral stroke), metabolic syndrome (e.g., characterized by loss of insulin sensitivity, obesity, hepatic steatosis and/or cholestasis), neurodegenerative disease (e.g., Alzheimer's disease, Parkinson disease, multiple sclerosis and apraxia), atopic/allergic reactions, osteoarthritis, rheumatoid arthritis, inflammatory pain, acne, psoriasis, rosacea, asthma, acute lung injury, chronic obstructive pulmonary disease, cystic fibrosis, sepsis, allergic rhinitis, sinusitis, periodontitis, inflammatory bowel disease, Crohn's disease, macular degeneration, dry eye syndrome, gastric ulceration, cancer, and auto-inflammatory disorders.

U.S. Pat. Nos. 7,378,444 and 7,595,341 describe analogs of lipid mediators derived from omega-3 fatty acids and methods of use for treating inflammatory, angioproliferative, cardiovascular, thrombophlebotic, vascular, ocular, dermatologic, neurodegenerative, pulmonary, endocrine, reproductive, rheumatologic and gastrointestinal diseases.

There is a need to develop compositions able to deliver SPMs and other lipid mediators of inflammation, including their analogs and derivatives, in therapeutically effective amounts to target tissues in order to fulfill the therapeutic promise of these compounds and translate the many promising in vitro and cellular pharmacology observations into clinical benefits. The present invention addresses these needs.

SUMMARY OF THE INVENTION

The present invention provides new salt forms of specialized pro-resolving mediators (referred to herein as "SPMs") which include lipoxins, resolvins, protectins, and their aspirin-triggered counterparts. The SPM salts described here contain at least one or two SPM molecules ionically bound to at least one basic function that is provided by a scaffold as described in Formulas I-IV. For example, in compounds of Formulas I and III, the scaffold is peptide-based; in compounds of Formula IV, the scaffold is a divalent metal-amino acid chelate or divalent metal-peptide chelate; and in compounds of Formula II, the scaffold is either a dipeptide or a monovalent metal or non-metal dipeptide.

The at least one or two SPM molecules forming the anionic counterion component of the salts described here may be referred to as "the SPM component" of the compounds and compositions described herein. In embodiments, the SPM component comprises or consists of an E series resolvin. In embodiments, the E series resolvin is selected from resolvin E1 (RvE1), resolvin E2 (RvE2), resolvin E3 (RvE3), and the aspirin-triggered (AT) counterparts of these resolvins, AT-RvE1, AT-RvE2, and AT-RvE3. In embodiments, the SPM component comprises or consists of an SPM selected from the group consisting of resolvin D1 (RvD1), resolvin D2 (RvD2), resolvin E1 (RvE1), protectin DX (PDX), and lipoxin A4 (LXA4). In embodiments, the SPM component comprises or consists of an SPM selected from an aspirin-triggered (AT) resolvin, lipoxin, or protectin. In embodiments, the AT resolvin, lipoxin, or protectin is selected from the group consisting of AT-RvD1, AT-RvD2, AT-PD1, AT-LXA4, and AT-RvE1. In embodiments, the SPM component is selected from the group consisting of RvE1, LXA4, AT-LXA4, and AT-RvE1. In embodiments, the SPM component consists of RvE1 or LXA4. The chemical names and formulas of these SPM compounds are provided for reference infra, in Tables 1-4.

Specific, non-limiting examples of the structures of some compounds of Formulas I, III, and IV are shown in Table 5.

In embodiments, an SPM salt described here is stabilized against chemical degradation compared to the free acid form of the SPM. In embodiments, an SPM salt described here has improved bioavailability compared to the free acid form of the SPM.

The compounds described here can be readily combined, e.g., by physical admixture, with each other and with other biologically active agents to produce a solid dosage form, or dissolved in aqueous media to produce a liquid dosage form. The compounds described here are thus suitable for formulation as aqueous liquids, e.g., for parenteral forms of administration including via intravenous and intramuscular injection, in addition to their suitability for formulation as solid dosage forms, such as oral or rectal dosage forms. These and other advantages are described in more detail infra.

In embodiments, the compounds and compositions described here are useful for treating a disease or disorder characterized by excessive inflammation.

In embodiments, the disease or disorder is an inflammatory bowel disease (IBD) related disease or disorder selected from ulcerative colitis, Crohn's disease, proctitis, pouchitis, Crohn's disease of the pouch, eosinophilic colitis, lymphocytic colitis, collagenous colitis, diversion colitis, chemical colitis, and ischemic colitis. In embodiments, the IBD-related disease or disorder is ulcerative colitis or Crohn's disease. In embodiments, the IBD-related disease or disorder is pouchitis.

In embodiments, the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

Compounds of Formula I

In embodiments, the disclosure provides compounds of Formula I or an enantiomer, polymorph, solvate, or hydrate thereof:

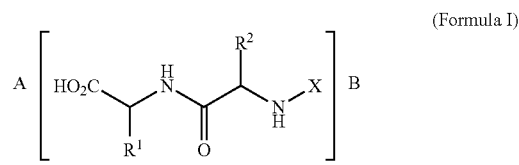

(Formula I)

wherein
A and B are each independently an SPM molecule;
A and B may be the same or different;
either A or B, but not both, may be absent,
$R^1$ and $R^2$ are each independently a $C_1$-$C_{10}$ alkyl comprising at least one basic function and is optionally branched;
X is H or CO—Z and Z is a single amino acid residue or a peptide comprising 2 to 18 amino acid residues;
when either A or B is absent:
one of $R^1$, $R^2$ and CO—Z is protonated; or
X is H and is positively charged; and
the one of $R^1$, $R^2$ and the CO—Z that is protonated or the positively charged H forms an ionic bond with either A or B; and
when A and B are both present:
two of $R^1$, $R^2$ and CO—Z are protonated; or
one of $R^1$, $R^2$ and CO—Z is protonated, and X is H and is positively charged; and
the two of $R^1$, $R^2$ and the CO—Z that are protonated or the one of $R^1$, $R^2$ and the CO—Z that is protonated and the positively charged H each respectively form an ionic bond with A and B.

Compounds of Formula I comprise a peptide component consisting of at least 2 amino acid moieties, and one or two SPM molecules (A, B) as the SPM component. In embodiments, A and B are the same or different and each is independently selected from an E series resolvin. In embodiments, the E series resolvin is selected from RvE1, RvE2, RvE3, AT-RvE1, AT-RvE2, and AT-RvE3. In embodiments, A and B are the same and each is independently selected from the group consisting of LXA4, AT-LXA4, PDX, RvE1, AT-RvE1, RvD1, AT-RvD1, RvD2 and AT-RvD2. The SPM component is described in more detail below.

The peptide component may be from 2 to 10 or 2 to 20 amino acids in length, preferably 2, 3, 4, or 5 amino acids in length. The peptide component consists of 2 amino acid residues when X is H, or is a peptide of from 3 to 5, 3 to 10, or 3 to 20 amino acid residues where X is CO—Z.

In embodiments, X is H and the peptide component consists of a dipeptide of amino acids independently selected from lysine, arginine, and glutamine, or a derivative of one or more of the foregoing. In embodiments, X is H and the peptide component consists of a dipeptide of lysine.

In embodiments, X is H and $R^1$ and $R^2$ are each independently selected from —$(CH_2)_3$—NHC$(NH_2^+)$—$NH_2$, —$(CH_2)_4$—$NH_3^+$, and —$(CH_2)_2$—C(O)$NH_3^+$. In embodiments, $R^1$ and $R^2$ are the same. In embodiments, $R^1$ and $R^2$ are different.

In embodiments, A and B are the same and selected from the group consisting of RvE1, RvE2, RvE3, AT-RvE1, AT-RvE2, and AT-RvE3; $R^1$ and $R^2$ are both —$(CH_2)_4$—$Y^2$, $Y^2$ is $NH_3^+$, and X is H. This selection of $R^1$, $R^2$, and $Y^2$ may be referred to herein as a "lysyl lysine" (which may be abbreviated herein as "lys-lys") dipeptide. In this embodiment, the peptide component is a lysine dipeptide.

In embodiments, A and B are the same and selected from the group consisting of RvD1, RvD2, RvE1, PDX, LXA4, AT-RvD1, AT-RvD2, AT-PD1, AT-LXA4, and AT-RvE1; $R^1$ and $R^2$ are both —$(CH_2)_4$—$Y^2$, $Y^2$ is $NH_3^+$, and X is H. As noted above, this selection of $R^1$, $R^2$, and $Y^2$ may be referred to herein as a "lysyl lysine" dipeptide or a "lys-lys" dipeptide. In this embodiment, the peptide component is a lysine dipeptide.

In embodiments, the compound of Formula I is selected from a mono or bis RvE1 lys-lys. In an embodiment, the compound of Formula I is bis RvE1 lys-lys. In embodiments, the compound of Formula I is selected from a mono or bis AT-RvE1 lys-lys. In an embodiment, the compound of Formula I is bis AT-RvE1 lys-lys.

In embodiments, the compound of Formula I is selected from a mono or bis RvE2 lys-lys. In an embodiment, the compound of Formula I is bis RvE2 lys-lys. In embodiments, the compound of Formula I is selected from a mono or bis AT-RvE2 lys-lys. In an embodiment, the compound of Formula I is bis AT-RvE2 lys-lys.

In embodiments, the compound of Formula I is selected from a mono or bis RvE3 lys-lys. In an embodiment, the compound of Formula I is bis RvE3 lys-lys. In embodiments, the compound of Formula I is selected from a mono or bis AT-RvE3 lys-lys. In an embodiment, the compound of Formula I is bis AT-RvE3 lys-lys.

In embodiments, the compound of Formula I is selected from a mono or bis LXA4 lys-lys. In an embodiment, the compound of Formula I is bis LXA4 lys-lys. In embodiments, the compound of Formula I is selected from a mono or bis AT-LXA4 lys-lys. In an embodiment, the compound of Formula I is bis AT-LXA4 lys-lys.

In embodiments, the compound of Formula I is selected from a mono or bis RvD1 lys-lys. In embodiments, the compound of Formula I is selected from a mono or bis AT-RvD1 lys-lys.

In embodiments, the compound of Formula I is selected from a mono or bis RvD2 1 lys-lys. In embodiments, the compound of Formula I is selected from a mono or bis AT-RvD2 lys-lys.

In embodiments, the compound of Formula I is selected from a mono or bis PDX lys-lys.

Exemplary compounds of the lysyl lysine embodiment of Formula I are provided in Table 5. In embodiments, the compound of Formula I is selected from the group consisting of Compounds 4, 9, 44, 49, 54, and 59 (E series) of Table 5. In embodiments, the compound of Formula I is selected from the group consisting of Compounds 4, 9, 14, 19, 24, 29, 34, and 39 of Table 5. In embodiments, the compound of Formula I is selected from the group consisting of Compounds 4, 9, 24, 29, 34, and 39 of Table 5. In embodiments, the compound of Formula I is selected from the group consisting of Compounds 4 and 9 of Table 5.

In embodiments, a Compound of Formula I, or a composition comprising same, is used in a method for treating a disease or disorder characterized by excessive inflammation. In embodiments, the disease or disorder is disorder is an IBD-related disease or disorder selected from ulcerative colitis, Crohn's disease, proctitis, pouchitis, Crohn's disease of the pouch, eosinophilic colitis, lymphocytic colitis, collagenous colitis, diversion colitis, chemical colitis, and ischemic colitis. In embodiments, the IBD-related disease or disorder is ulcerative colitis or Crohn's disease. In embodiments, the IBD-related disease or disorder is pouchitis.

In embodiments, the disclosure provides a method for treating an IBD-related disease or disorder as described above, the method comprising administering to a subject in need of such treatment, a Compound of Formula I. In embodiments of the methods, the Compound of Formula I is selected from a mono or bis RvE1 lys-lys, a mono or bis AT-RvE1 lys-lys, a mono or bis RvE2 lys-lys, a mono or bis AT-RvE2 lys-lys, a mono or bis RvE3 lys-lys, and a mono or bis AT-RvE3 lys-lys. In embodiments of the methods, the Compound of Formula I is selected from a mono or bis RvE1 lys-lys, a mono or bis AT-RvE1 lys-lys, a mono or bis LXA4 lys-lys, and a mono or bis AT-LXA4 lys-lys.

Compounds of Formula II

In embodiments, the disclosure provides compounds of Formula II or an enantiomer, polymorph, solvate, or hydrate thereof:

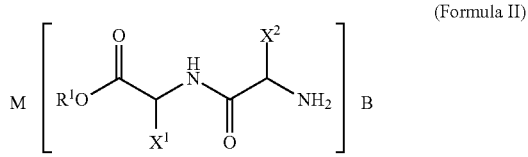

(Formula II)

where $R^1$ is H, or absent. $X^1$ and $X^2$ are each independently the side chain of an amino acid residue. M is a positively charged optional molecule. B is an SPM molecule.

A compound of Formula II consists of at least (i) a dipeptide component and (ii) an SPM component (B), with a positively charged optional molecule (M). The dipeptide component contains $X^1$ and $X^2$ which may be the same or different, and are each the side chain of an amino acid residue. In embodiments, at least one of $X^1$ and $X^2$ is the side chain of an amino acid residue selected from serine, threonine, glycine, alanine, valine, leucine, isoleucine, methionine, and phenylalanine. In embodiments, where one of $X^1$ and $X^2$ is the side chain of an amino acid residue selected from serine, threonine, glycine, alanine, valine, leucine, isoleucine, methionine, and phenylalanine, the remainder of $X^1$ or $X^2$ is the side chain of an amino acid independently selected from lysine, arginine, histidine, aspartate, glutamate, serine, threonine, asparagine, glutamine, cysteine, glycine, proline, alanine, valine, isoleucine, leucine, methionine, phenylalanine, tyrosine, and tryptophan. In embodiments, the remainder is the side chain of lysine. In embodiments, at least one of $X^1$ and $X^2$ is the side chain of glycine, valine, serine, leucine, or histidine, and the remainder is the side chain of lysine.

The positively charged optional molecule (M) has at least one basic function in protonated form which forms an ionic bond with the terminal carboxyl of the amino acid component. In embodiments, M is a monovalent metal cation, e.g., $Na^+$, $K^+$, or a molecule having at least one basic function, such as a monovalent amine-based cation, e.g., tri-ethanolamine, or tri-ethylamine, or a basic pharmaceutical compound such as metformin or gabapentin.

As described in more detail below, the compounds of Formula II encompass simple salts of dipeptides and an SPM (Formula IIa), simple metal salts of the dipeptides and an SPM with a monovalent metal (Formula IIb), and simple non-metal salts of the dipeptides and an SPM with a non-metal molecule having at least one basic function (Formula IIc).

In embodiments of the compound of Formula II, B is an E series resolvin. In embodiments of the compound of Formula II, B is selected from the group consisting of RvE1, RvE2, RvE3, AT-RvE1, AT-RvE2, and AT-RvE3.

In embodiments of the compound of Formula II, B is selected from the group consisting of RvD1, RvD2, RvE1, PDX, LXA4, AT-RvD1, AT-RvD2, AT-LXA4, and AT-RvE1.

In embodiments, the compound of Formula II is a glycine dipeptide where $R^1$ is H, $X^1$ and $X^2$ are each H, M is absent and B is selected from the group consisting of RvE1, RvE2, RvE3, AT-RvE1, AT-RvE2, and AT-RvE3.

In embodiments, the compound of Formula II is a glycine dipeptide where $R^1$ is H, $X^1$ and $X^2$ are each H, M is absent and B is selected from the group consisting of RvD1, RvD2, RvE1, PDX, LXA4, AT-RvD1, AT-RvD2, AT-LXA4, and AT-RvE1.

In embodiments, the disclosure provides a method for treating a disease or disorder selected from an IBD-related disease or disorder as described above, the method comprising administering to a subject in need of such treatment, a Compound of Formula II.

Compounds of Formula III

In embodiments, the disclosure provides compounds of Formula III or an enantiomer, polymorph, solvate, or hydrate thereof:

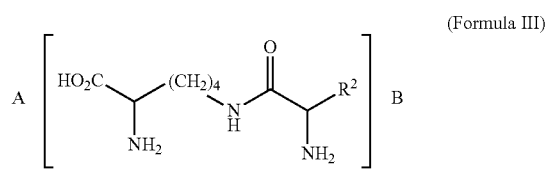

(Formula III)

wherein
$R^2$ is a $C_1$-$C_{10}$ alkyl comprising at least one basic function;
A and B are each independently an SPM molecule;
A and B may be the same or different; and
either A or B, but not both, may be absent.

In embodiments, $R^2$ is the side chain of an amino acid residue selected from lysine, arginine, and glutamine. In embodiments, $R^2$ is selected from the group consisting of $-(CH_2)_3-NHC(NH_2^+)NH_2$, $-(CH_2)_4-NH_3^+$, and $-(CH_2)_2-C(O)NH_3^+$. In embodiments, $R^2$ is $-(CH_2)_4-NH_3^+$.

In an embodiment of the compound of Formula III, A and B are the same or different and each is independently selected from an E series resolvin and $R^2$ is $-(CH_2)_4-NH_3^+$. In embodiments, the E series resolvin is selected from RvE1, RvE2, RvE3, AT-RvE1, AT-RvE2, and AT-RvE3. This selection of $R^2$ may be referred to herein as a "linear lysyl lysine" (linear lys-lys) dipeptide. In this embodiment, the peptide component is a lysine dipeptide. In embodiments, A and B are the same.

In an embodiment of the compound of Formula III, A and B are the same and selected from the group consisting of RvD1, RvD2, RvE1, PDX, LXA4, AT-RvD1, AT-RvD2, AT-PD1, AT-LXA4, and AT-RvE1, and $R^2$ is $-(CH_2)_4-NH_3^+$. This selection of $R^2$ may be referred to herein as a "linear lysyl lysine" (linear "lys-lys") dipeptide. In this embodiment, the peptide component is a lysine dipeptide.

In embodiments, the compound of Formula III is selected from a mono or bis RvE1 linear lys-lys. In an embodiment, the compound of Formula III is bis RvE1 linear lys-lys. In embodiments, the compound of Formula III is selected from a mono or bis AT-RvE1 linear lys-lys. In an embodiment, the compound of Formula III is bis AT-RvE1 linear lys-lys.

In embodiments, the compound of Formula III is selected from a mono or bis RvE2 linear lys-lys. In an embodiment, the compound of Formula III is bis RvE2 linear lys-lys. In embodiments, the compound of Formula III is selected from a mono or bis AT-RvE2 linear lys-lys. In an embodiment, the compound of Formula III is bis AT-RvE2 linear lys-lys.

In embodiments, the compound of Formula III is selected from a mono or bis RvE3 linear lys-lys. In an embodiment, the compound of Formula III is bis RvE3 linear lys-lys. In embodiments, the compound of Formula III is selected from a mono or bis AT-RvE3 linear lys-lys. In an embodiment, the compound of Formula III is bis AT-RvE3 linear lys-lys.

In embodiments, the compound of Formula III is selected from a mono or bis LXA4 linear lys-lys. In an embodiment, the compound of Formula III is bis LXA4 linear lys-lys. In embodiments, the compound of Formula III is selected from a mono or bis AT-LXA4 lys-lys. In an embodiment, the compound of Formula III is bis AT-LXA4 linear lys-lys.

In embodiments, the compound of Formula III is selected from a mono or bis RvD1 linear lys-lys. In embodiments, the compound of Formula III is selected from a mono or bis AT-RvD1 linear lys-lys.

In embodiments, the compound of Formula III is selected from a mono or bis RvD2 linear lys-lys. In embodiments, the compound of Formula III is selected from a mono or bis AT-RvD2 linear lys-lys.

In embodiments, the compound of Formula III is selected from a mono or bis PDX linear lys-lys.

Exemplary compounds of Formula III are provided in Table 5. In embodiments, the compound of Formula III is selected from the group consisting of Compounds 5, 10, 45, 50, 55, and 60 (E series) of Table 5. In embodiments, a compound of Formula III is selected from the group consisting of Compounds 5, 10, 15, 20, 25, 30, 35, and 40 of Table 5. In embodiments, a compound of Formula III is selected from the group consisting of Compounds 5 and 10 (RvE1 and AT-RvE1 embodiments) of Table 5. In embodiments, a compound of Formula III is selected from the group consisting of Compounds 15 and 20 (LXA4 and AT-LXA4 embodiments) of Table 5.

In embodiments, a Compound of Formula III, or a composition comprising same, is used in a method for treating a disease or disorder characterized by excessive inflammation. In embodiments, the disease or disorder is disorder is an IBD-related disease or disorder selected from ulcerative colitis, Crohn's disease, proctitis, pouchitis, Crohn's disease of the pouch, eosinophilic colitis, lymphocytic colitis, collagenous colitis, diversion colitis, chemical colitis, and ischemic colitis. In embodiments, the IBD-related disease or disorder is ulcerative colitis or Crohn's disease. In embodiments, the IBD-related disease or disorder is pouchitis.

In embodiments, the disclosure provides a method for treating an IBD-related disease or disorder as described above, the method comprising administering to a subject in need of such treatment, a Compound of Formula III. In embodiments of the methods, the Compound of Formula III is selected from a mono or bis RvE1 linear lys-lys, a mono or bis AT-RvE1 linear lys-lys, a mono or bis RvE2 linear lys-lys, a mono or bis AT-RvE2 linear lys-lys, a mono or bis RvE3 linear lys-lys, and a mono or bis AT-RvE3 linear lys-lys. In embodiments, the Compound of Formula III for use in the method is selected from a mono or bis RvE1 linear lys-lys, a mono or bis At-RvE1 linear lys-lys, a mono or bis LXA4 linear lys-lys, and a mono or bis AT-LXA4 linear lys-lys.

Compounds of Formula IV

In embodiments, the disclosure provides compounds of Formula IV or an enantiomer, polymorph, solvate, or hydrate thereof:

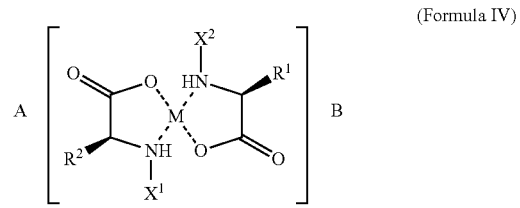

(Formula IV)

wherein
M is a divalent metal;
A and B are each independently an SPM anion;
A and B may be the same or different;
either A or B, but not both, may be absent;
$R^1$ and $R^2$ are each independently a $C_1$-$C_{10}$ alkyl comprising at least one basic function;
$X^1$ and $X^2$ are each independently H or CO—Z and Z is a peptide comprising 1 to 5 amino acids or a pharmaceutically acceptable salt thereof;
when either A or B is absent:
one of $R^1$, $R^2$ and the two CO—Z's is protonated; or
one of the two H's is positively charged; and
the one of $R^1$, $R^2$ and the two CO—Z's that is protonated or the one of the positively charged H's forms an ionic bond with either A or B; and
when A and B are both present:
two of $R^1$, $R^2$ and the two CO—Z's are protonated; or
one of $R^1$, $R^2$ and the two CO—Z's is protonated, and one of the two H's is positively charged; and
the two of $R^1$, $R^2$ and the two CO—Z's that are protonated or the one of $R^1$, $R^2$ and the two CO—Z's that is protonated and the positively charged H each respectively form an ionic bond with A and B.

Compounds of Formula IV have two amino acid moieties coordinated around a divalent metal cation as the amino acid component and one or two SPM molecules as the SPM component. In embodiments, the divalent metal is $Mg^{2+}$, $Ca^{2+}$, $Mn^{2+}$, $Fe^{2+}$, $Cu^{2+}$, $Co^{2+}$, $Ni^{2+}$, $Mo^{2+}$ or $Zn^{2+}$. In embodiments, the divalent metal is $Mg^{2+}$. In embodiments, the divalent metal is $Ca^{2+}$. In embodiments, the divalent metal is $Zn^{2+}$. In embodiments, the amino acid component includes or consists of lysine or arginine. In embodiments, the amino acid component includes lysine or arginine. In embodiments, the basic function of $R^1$ and $R^2$ is selected from a primary amine, a secondary amine, a tertiary amine, and a guanidine. In embodiments, basic function refers to —$NH_3$, —$NHC(NH_2^+)$—$NH_2$, —$NHR^6R^7$, or —$NR^6R^7R^8$, wherein $R^6$, $R^7$, $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a hydrogen bond donor. In embodiments, the basic function is a positively charged amine.

In embodiments, $R^1$ and $R^2$ are each the side chain of an amino acid residue having a basic function. In embodiments, $R^1$ and $R^2$ are the same and the amino acid residue is lysine or arginine.

In embodiments, $R^1$ and $R^2$ are independently selected from —$(CH_2)_3$—$Y^1$, and —$(CH_2)_4$—$Y^2$, where $Y^1$ and $Y^2$ are each a basic function which may be the same or different. In embodiments, $R^1$ is —$CH_2CH_2NH_3$. In embodiments, $R^2$ is —CH$_2$CH$_2$NH$_3$. In embodiments, R$^1$ is —CH$_2$CH$_2$CH$_2$CH$_2$NH$_3$. In embodiments, R$^2$ is —CH$_2$CH$_2$CH$_2$CH$_2$NH$_3$.

In embodiments, R$^1$ and R$^2$ are both —(CH$_2$)$_4$—Y$^2$, and Y$^2$ is —NH$_3^+$.

In embodiments, R$^1$ and R$^2$ are both —(CH$_2$)$_3$—Y$^1$, and Y$^1$ is —NHC(NH$_2^+$)NH$_2$.

In embodiments, R$^1$ is —(CH$_2$)$_3$—Y$^1$, Y$^1$ is —NHC(NH$_2^+$)NH$_2$, R$^2$ is —(CH$_2$)$_4$—Y$^2$, and Y$^2$ is NH$_3^+$. In embodiments, R$^1$ is —(CH$_2$)$_4$—Y$^2$, Y$^2$ is NH$_3$, R$^2$ is —(CH$_2$)$_3$—Y$^1$, and Y$^1$ is NHC(NH$_2^+$)NH$_2$.

In embodiments, X$^1$ and X$^2$ are the same and are hydrogen (H).

In embodiments, the SPM molecule of A and B is as described infra.

In an embodiment of the compound of Formula IV, A and B are the same or different and each is independently selected from an E series resolvin. In embodiments, the E series resolvin is selected from RvE1, RvE2, RvE3, AT-RvE1, AT-RvE2, and AT-RvE3, M is Mg$^{2+}$, Ca$^{2+}$, or Zn$^{2+}$, R$^1$ and R$^2$ are both —(CH$_2$)$_4$—Y$^2$ and Y$^2$ is NH$_3$+; and X$^1$ and X$^2$ are H. This selection of R$^1$, R$^2$, and Y$^2$ may be referred to herein as the metal "di-lysinate", e.g., "magnesium di-lysinate" or "Mg-di-lysinate". In Table 5, the metal di-lysinate name is abbreviated "SPM-Mlys" where "M" is the metal, e.g., Mg, Ca, or Zn. In this embodiment, the peptide component consists of a lysine dipeptide. In embodiments, A and B are the same.

In an embodiment of the compound of Formula IV, A and B are the same and selected from the group consisting of RvD1, RvD2, RvE1, PDX, LXA4, AT-RvD1, AT-RvD2, AT-PD1, AT-LXA4, and AT-RvE1; M is Mg$^{2+}$, Ca$^{2+}$, or Zn$^{2+}$, R$^1$ and R$^2$ are both —(CH$_2$)$_4$—Y$^2$ and Y$^2$ is NH$_3$+; and X$^1$ and X$^2$ are H. This selection of R$^1$, R$^2$, and Y$^2$ may be referred to herein as the metal "di-lysinate", e.g., "magnesium di-lysinate" or "Mg-di-lysinate". In this embodiment, the peptide component consists of a lysine dipeptide.

In embodiments, the compound of Formula IV is selected from a mono or bis RvE1 Mg-di-lysinate. In an embodiment, the compound of Formula IV is bis RvE1 Mg-di-lysinate. In embodiments, the compound of Formula IV is selected from a mono or bis AT-RvE1 Mg-di-lysinate. In an embodiment, the compound of Formula IV is bis AT-RvE1 Mg-di-lysinate.

In embodiments, the compound of Formula IV is selected from a mono or bis RvE2 Mg-di-lysinate. In an embodiment, the compound of Formula IV is bis RvE2 Mg-di-lysinate. In embodiments, the compound of Formula IV is selected from a mono or bis AT-RvE2 Mg-di-lysinate. In an embodiment, the compound of Formula IV is bis AT-RvE2 Mg-di-lysinate.

In embodiments, the compound of Formula IV is selected from a mono or bis RvE3 Mg-di-lysinate. In an embodiment, the compound of Formula IV is bis RvE3 Mg-di-lysinate. In embodiments, the compound of Formula IV is selected from a mono or bis AT-RvE3 Mg-di-lysinate. In an embodiment, the compound of Formula IV is bis AT-RvE3 Mg-di-lysinate.

In embodiments, the compound of Formula IV is selected from a mono or bis LXA4 Mg-di-lysinate. In an embodiment, the compound of Formula IV is bis LXA4 Mg-di-lysinate. In embodiments, the compound of Formula IV is selected from a mono or bis AT-LXA4 Mg-di-lysinate. In an embodiment, the compound of Formula IV is bis AT-LXA4 Mg-di-lysinate.

In embodiments, the compound of Formula IV is selected from a mono or bis RvD1 Mg-di-lysinate. In embodiments, the compound of Formula IV is selected from a mono or bis AT-RvD1 Mg-di-lysinate.

In embodiments, the compound of Formula IV is selected from a mono or bis RvD2 Mg-di-lysinate. In embodiments, the compound of Formula IV is selected from a mono or bis AT-RvD2 Mg-di-lysinate.

In embodiments, the compound of Formula IV is selected from a mono or bis PDX Mg-di-lysinate.

Exemplary compounds of Formula IV are provided in Table 5. In embodiments, the compound of Formula IV is selected from the group consisting of Compounds 1-3, 6-8, 41-43, 46-48, 51-53, and 56-58 (E series) of Table 5. In embodiments, a compound of Formula IV is selected from the group consisting of Compounds 1-3, 6-8, 11-13, 16-18, 21-23, 26-28, 31-33, and 36-38 of Table 5. In embodiments, a compound of Formula IV is selected from the group consisting of Compounds 1-3 and 6-8 of Table 5 (RvE1 and AT-RvE1 embodiments). In embodiments, a compound of Formula IV is selected from the group consisting of Compounds 11-13 and 16-18 of Table 5 (LXA4 and AT-LXA4 embodiments). In embodiments, a compound of Formula IV is selected from the group consisting of Compounds 21-23 and 26-28 of Table 5 (RvD1 and AT-RvD1 embodiments).

In embodiments, a Compound of Formula IV, or a composition comprising same, is used in a method for treating a disease or disorder characterized by excessive inflammation. In embodiments, the disease or disorder is disorder is an IBD-related disease or disorder selected from ulcerative colitis, Crohn's disease, proctitis, pouchitis, Crohn's disease of the pouch, eosinophilic colitis, lymphocytic colitis, collagenous colitis, diversion colitis, chemical colitis, and ischemic colitis. In embodiments, the IBD-related disease or disorder is ulcerative colitis or Crohn's disease. In embodiments, the IBD-related disease or disorder is pouchitis.

In embodiments, the disclosure provides a method for treating a disease or disorder selected from an IBD-related disease or disorder as described above, the method comprising administering to a subject in need of such treatment, a Compound of Formula IV. In embodiments of the methods, the Compound of Formula IV is selected from a mono or bis RvE1 Mg, Ca, or Zn di-lysinate, a mono or bis AT-RvE1 Mg, Ca, or Zn di-lysinate, a mono or bis RvE2 Mg, Ca, or Zn di-lysinate, a mono or bis AT-RvE2 Mg, Ca, or Zn di-lysinate, a mono or bis RvE3 Mg, Ca, or Zn di-lysinate, and a mono or bis AT-RvE3 Mg, Ca, or Zn di-lysinate. In embodiments, the Compound of Formula IV is selected from a mono or bis RvE1 Mg, Ca, or Zn di-lysinate, a mono or bis AT-RvE1 Mg, Ca, or Zn di-lysinate, a mono or bis LXA4 Mg, Ca, or Zn di-lysinate, and a mono or bis AT-LXA4 Mg, Ca, or Zn di-lysinate. In embodiments, the di-lysinate is a magnesium di-lysinate.

The SPM Component

As discussed above, the compounds represented by Formulas I-IV each contain at least one or two SPM molecules, which may be referred to herein as the "SPM component" of the compound, and a scaffold portion to which the SPM component is ionically bound. The terms "mono" and "bis" refer to one (mono) or two (bis) SPM molecules in the salt compound.

The term "SPM" refers to SPMs such as protectins and resolvins as well as to lipoxins and aspirin-triggered lipid mediators (e.g., aspirin-triggered lipoxins and protectins), as described in more detail infra. Examples of particular SPM molecules that may form the SPM component of the compounds described here, as well as their precursor molecules, are given in Tables 1-4 infra. It is understood that the neutral compounds described in these tables may become charged (i.e., deprotonated) if solvated at the appropriate pH.

In embodiments, the SPM component of a compound described here comprises or consists of one or two SPM molecules selected from mediators derived from arachidonic acid (AA) (Table 1), mediators derived from eicosapentaenoic acid (EPA) (Table 2); mediators derived from docosahexaenoic acid (DHA) (Table 3); and aspirin-triggered mediators (Table 4). In embodiments, the SPM component of a compound described here comprises or consists of two SPM molecules selected from Tables 1-4. In embodiments, the two SPM molecules are the same or different. In embodiments, the two SPM molecules are the same and are selected from an E series resolvin; in embodiments, the E series resolvin is selected from RvE1, RvE2, RvE3, AT-RvE1, AT-RvE2, and AT-RvE3. In embodiments, the two SPM molecules are the same and are selected from the group consisting of RvD1, RvD2, RvE1, PDX, LXA4, AT-RvD1, AT-RvD2, AT-PD1, AT-LXA4, and AT-RvE1. In embodiments, the SPM component of a compound described here consists of one or two SPM molecules selected from an E series resolvin; in embodiments, the E series resolvin is selected from RvE1, RvE2, RvE3, AT-RvE1, AT-RvE2, and AT-RvE3. In embodiments, the SPM component of a compound described here consists of one or two SPM molecules selected from the group consisting of RvD1, RvD2, RvE1, PDX, LXA4, AT-RvD1, AT-RvD2, AT-PD1, AT-LXA4, and AT-RvE1. In embodiments, the SPM component is selected from an E series resolvin; in embodiments, the E series resolvin is selected from RvE1, RvE2, RvE3, AT-RvE1, AT-RvE2, and AT-RvE3. In embodiments, the SPM component is selected from RvE1, AT-RvE1, LXA4, and AT-LXA4.

The present disclosure also provides compositions including a single compound described herein, or compositions comprising mixtures of two or more different compounds described herein. In embodiments, the composition is a pharmaceutical or veterinary composition and the carrier is acceptable for administration to humans or animals.

In embodiments, the composition is a pharmaceutical composition in the form of a solid oral dosage form, a dosage form suitable for rectal administration, or a parenteral dosage form. In embodiments, the dosage form suitable for rectal administration is an ointment, suppository, or enema. In embodiments, the parenteral dosage form is suitable for intravenous, intra-arterial, or intramuscular administration, e.g., via injection of an aqueous liquid.

The present disclosure also provides methods of use for the compounds described here, and for the compositions comprising same. In embodiments, a compound described here, or a composition comprising same, is useful for treating a disease or disorder in which resolution of inflammation provides a beneficial effect, such as those characterized by chronic or excessive inflammation. For example, the compounds and compositions described here are useful in treating gastrointestinal diseases and disorders, pulmonary diseases and disorders, arthritic diseases and disorders, cardiovascular diseases and disorders, metabolic diseases and disorders, infectious diseases and disorders, and neurological diseases and disorders.

In embodiments, the disclosure provides methods of treating a gastrointestinal (GI) disease or disorder by administering to a subject in need of such treatment a Compound of Formula I, II, III, or IV, wherein the GI disease or disorder is selected from those described infra in the section entitled "Pharmaceutical Uses". In embodiments of the methods, the compound is a Compound of Formula I having a lysyl-lysine dipeptide component and an SPM component selected from an E series resolvin; in embodiments, the E series resolvin is selected from RvE1, RvE2, RvE3, AT-RvE1, AT-RvE2, and AT-RvE3. In embodiments of the methods, the compound is a Compound of Formula I having a lysyl-lysine dipeptide component and an SPM component selected from the group consisting of RvD1, RvD2, RvE1, PDX, LXA4, AT-RvD1, AT-RvD2, AT-LXA4, and AT-RvE1. In embodiments, the SPM component is selected from RvE1, AT-RvE1, LXA4, and AT-LXA4. In embodiments of the methods, the compound is a Compound of Formula IV having a magnesium, calcium, or zinc di-lysinate peptide component and an SPM component selected from an E series resolvin; in embodiments, the E series resolvin is selected from RvE1, RvE2, RvE3, AT-RvE1, AT-RvE2, and AT-RvE3. In embodiments of the methods, the compound is a Compound of Formula IV having a magnesium, calcium, or zinc di-lysinate peptide component and an SPM component selected from the group consisting of RvD1, RvD2, RvE1, PDX, LXA4, AT-RvD1, AT-RvD2, AT-LXA4, and AT-RvE1. In embodiments, the SPM component is selected from RvE1, AT-RvE1, LXA4, and AT-LXA4. The SPM component may be mono or bis, but is preferably bis.

The present disclosure also provides a package or kit comprising a unit dosage form of a compound described herein, or a composition comprising same, at least one container for holding the unit dosage forms, and instructions for use.

DETAILED DESCRIPTION OF THE INVENTION

Figure 1A:
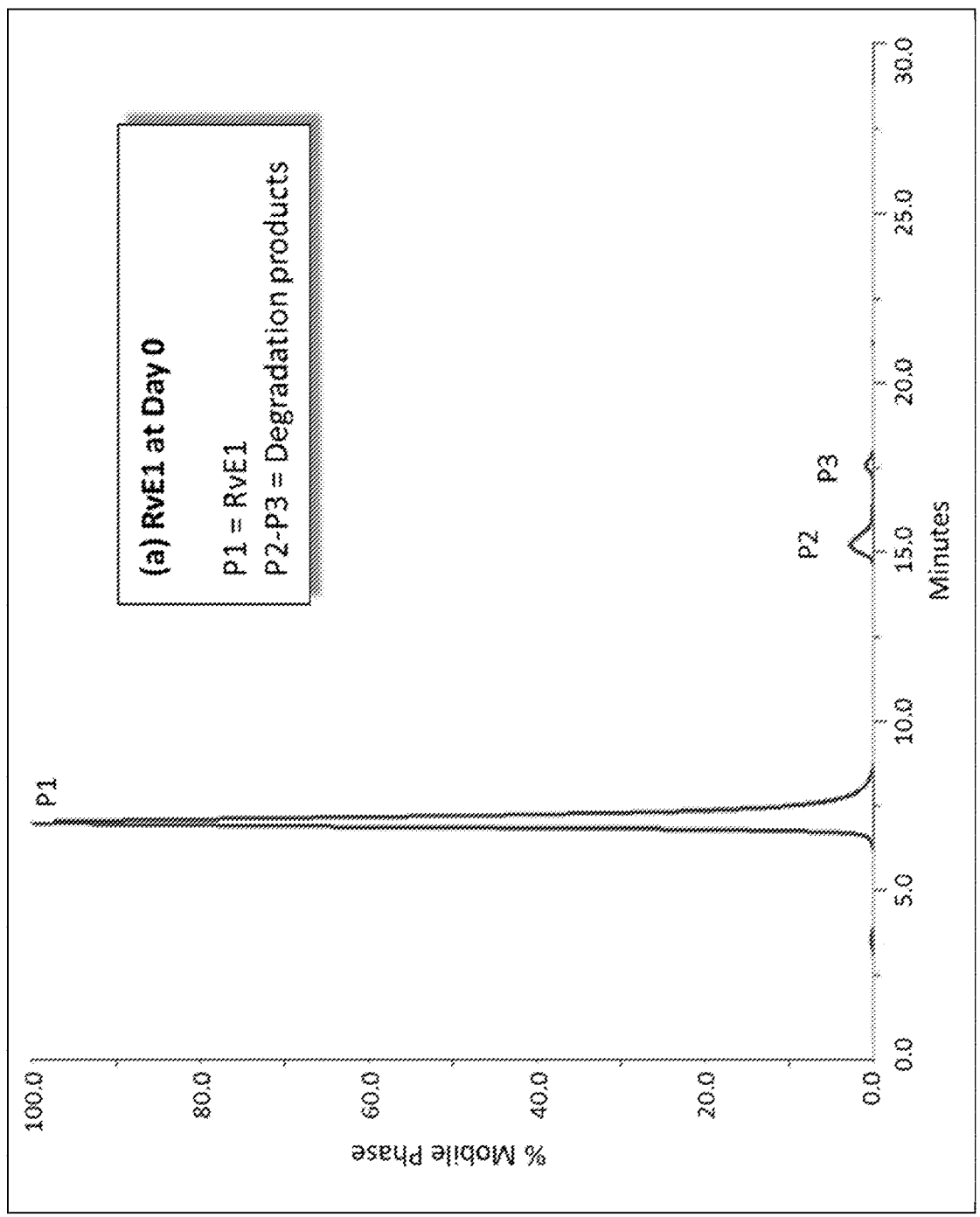
FIG. 1A,B: Chemical Stability of RvE1. A, HPLC trace of RvE1 free acid at time zero. B, HPLC trace of RvE1 at 8-weeks.

The present invention provides new salt forms of specialized pro-resolving mediators (referred to herein as "SPMs") which include lipoxins, resolvins, protectins, and their aspirin-triggered counterparts, as described in more detail infra. The compounds described here advantageously provide SPM molecules in a pharmacologically useful form due at least in part to their increased physical and/or chemical stability.

The compounds described here contain at least one or two SPM molecules ionically bound to at least one basic function that is provided by a scaffold as described in Formulas I-IV below. In general, the carboxylic acid moiety of the SPM molecule or molecules forming the SPM component of the compounds described here is deprotonated to form an ionic bond with a basic function (or functions) of the scaffold portion of the compound.

The compounds described herein can exist in unsolvated forms as well as solvated forms, including hydrated forms. In general, the solvated forms are equivalent to unsolvated forms and are intended to be encompassed within the scope of the present invention. In general, all physical forms are equivalent for the uses contemplated by the present invention and are intended to be within the scope of the present invention.

The abbreviations used herein have their conventional meaning within the chemical and biological arts. The chemical structures and formulae set forth herein are constructed according to the standard rules of chemical valency known in the chemical arts. For example, in instances where a substituents such as —$NH_3$ are shown without a charge, it is understood to possess a formal charge, i.e. $NH_3^+$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons).

The term "basic function" refers to a positively charged or protonated primary amine, a positively charged secondary amine, a positively charged tertiary amine, or a positively charged guanidine. In embodiments, basic function refers to —$NH_3$, —$NHC(NH_2^+)NH_2$, —$NHR^6R^7$, —$NR^6R^7R^8$, wherein $R^6$, $R^7$, and $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a positively charged amine.

It is understood that due to resonance a charge may be distributed across the molecule. The chemical structures and formulae set forth herein are constructed according to the standard rules of chemical valency known in the chemical arts, and as such one of skill in the art would recognize the equivalency of the moieties possessing resonance structures. For example, —$NHC(NH_2^+)NH_2$ refers to

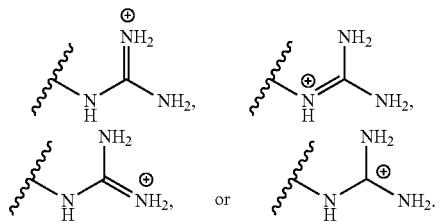

In embodiments, the "side chain of an amino acid" or "side chain" or "side-chain" as used herein is used in accordance with its ordinary meaning and refers to the functional substituent contained on naturally occurring amino acids. Naturally occurring amino acids are those encoded by the genetic code (e.g. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the side chain of an amino acid is ionized (e.g., it has a formal charge).

In embodiments, the side chain is selected from the group consisting of H,

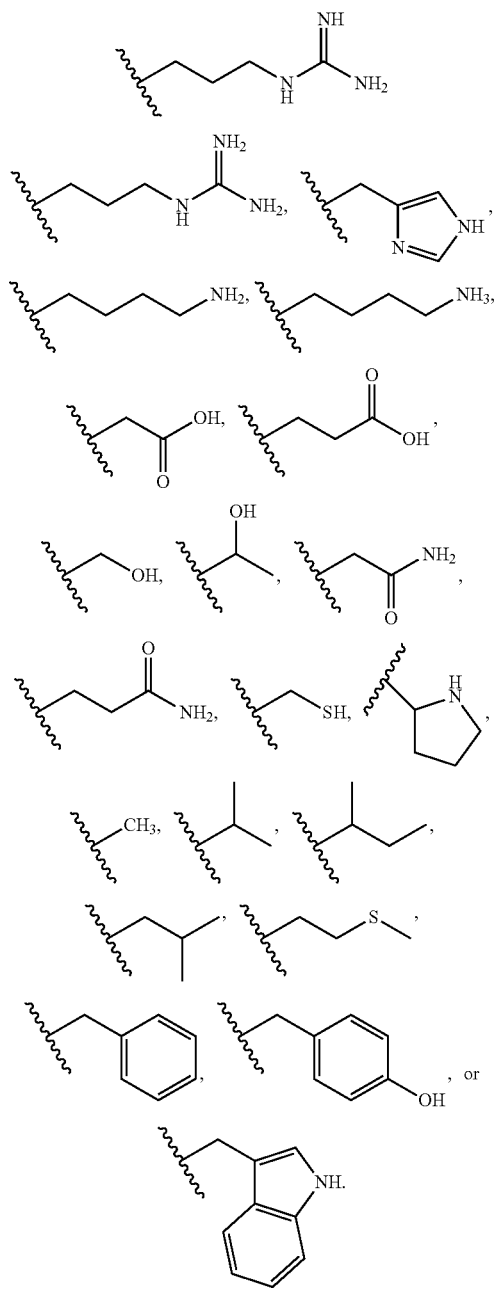

In embodiments, the side chain is H. In embodiments, the side chain is

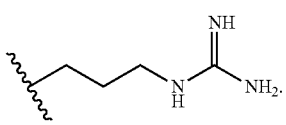 [SMILES: *CCCNC(=N)N]

In embodiments, the side chain is

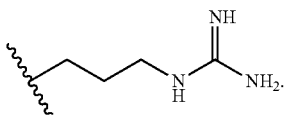 [SMILES: *CCCNC(=N)N]

In embodiments, the side chain is

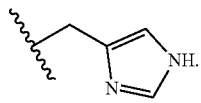

In embodiments, the side chain is

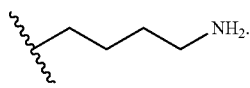

In embodiments, the side chain is

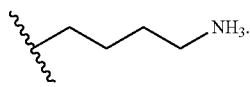

In embodiments, the side chain is

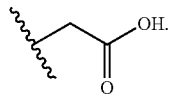

In embodiments, the side chain is

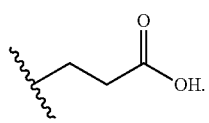

In embodiments, the side chain is

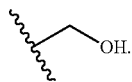

In embodiments, the side chain is

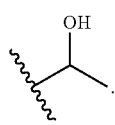

In embodiments, the side chain is

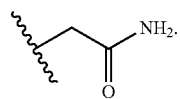

In embodiments, the side chain is

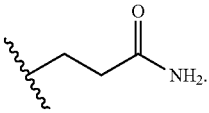 [SMILES: *CCC(N)=O]

In embodiments, the side chain is

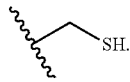

In embodiments, the side chain is

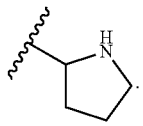

In embodiments, the side chain may optionally be joined to an adjacent nitrogen to form a unsubstituted heterocycloalkyl (e.g., pyyrolidinyl).

In embodiments, the side chain is

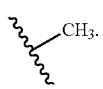

In embodiments, the side chain is

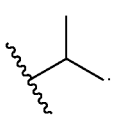

In embodiments, the side chain is

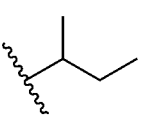

In embodiments, the side chain is

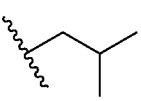

In embodiments, the side chain is

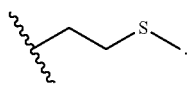 [SMILES: *CCSC]

In embodiments, the side chain is

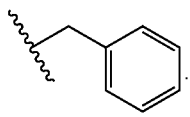

In embodiments, the side chain is

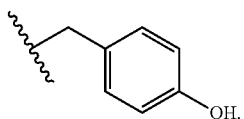 [SMILES: *Cc1ccc(O)cc1]

In embodiments, the side chain is

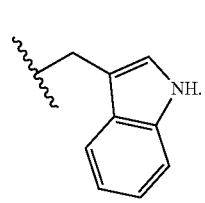 [SMILES: *Cc1c[nH]c2ccccc12]

The side chain of glycine is H. The side chain of arginine is

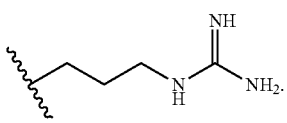

The side chain of arginine is

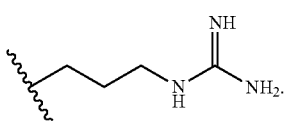 [SMILES: *CCCNC(=N)N]

The side chain of histidine is

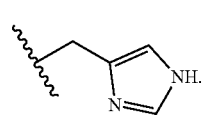 [SMILES: *Cc1c[nH]cn1]

The side chain of lysine is

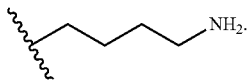

The side chain of aspartic acid is

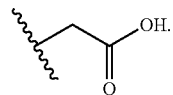

The side chain of glutamic acid is

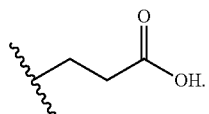

The side chain of serine is

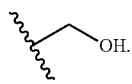 [SMILES: *CO]

The side chain of threonine is

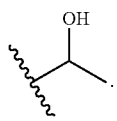

The side chain of asparagine is

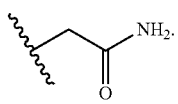

The side chain of glutamine is

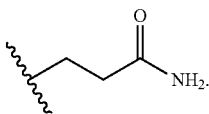 [SMILES: *CCC(N)=O]

The side chain of cysteine is

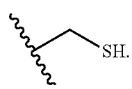

The side chain of proline is

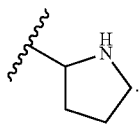

The side chain of alanine is

The side chain of valine is

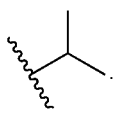 [SMILES: *C(C)C]

The side chain of isoleucine is

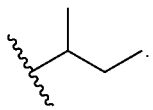 [SMILES: *C(C)CC]

The side chain of leucine is

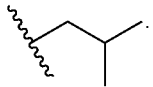 [SMILES: *CC(C)C]

The side chain of methionine is

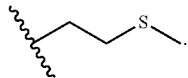

The side chain of phenylalanine is

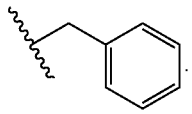

The side chain of tyrosine is

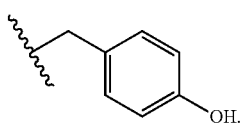 [SMILES: *Cc1ccc(O)cc1]

The side chain of tryptophan is

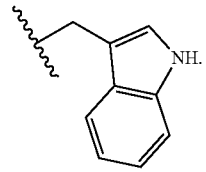 [SMILES: *Cc1c[nH]c2ccccc12]

The term "non-natural amino acid side-chain" refers to the functional substituent of compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride,cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-(3-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl]acetic acid purum, Boc-3-(2-quinolyl)-Ala-OH, N—Boc-1,2,3,6-tetrahydro-2-pyridinecarboxylic acid, Boc-3-(4-thiazolyl)-Ala-OH, Boc-3-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

Formula I Compounds

In embodiments, the disclosure provides compounds of Formula I, including enantiomers, polymorphs, solvates, and hydrates thereof:

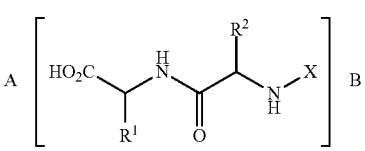

(Formula I)

wherein

A and B are each independently an SPM molecule;

A and B may be the same or different;

either A or B, but not both, may be absent, $R^1$ and $R^2$ are each independently a $C_1$-$C_{10}$ alkyl comprising at least one basic function;

X is H or CO—Z and Z is a single amino acid residue or a peptide comprising 2 to 18 amino acid residues;

when either A or B is absent:

one of $R^1$, $R^2$ and CO—Z is protonated; or

H is positively charged; and the one of $R^1$, $R^2$ and the CO—Z that is protonated or the positively charged H forms an ionic bond with either A or B; and when A and B are both present:

two of $R^1$, $R^2$ and CO—Z are protonated; or one of $R^1$, $R^2$ and CO—Z is protonated, and H is positively charged; and the two of $R^1$, $R^2$ and the CO—Z that are protonated or the one of $R^1$, $R^2$ and the CO—Z that is protonated and the positively charged H each respectively form an ionic bond with A and B.

Compounds of Formula I comprise a peptide component consisting of at least 2 amino acid moieties, and one or two SPM molecules (A, B) as the SPM component. The SPM component is described in more detail below. In embodiments, the SPM component comprises or consists of an SPM selected from an E series resolvin; in embodiments, the E series resolvin is selected from RvE1, RvE2, RvE3, AT-RvE1, AT-RvE2, and AT-RvE3. In embodiments, the SPM component comprises or consists of an SPM selected from the group consisting of RvD1, RvD2, RvE1, PDX, and LXA4. In embodiments, the SPM component comprises or consists of an SPM selected from an aspirin-triggered (AT) resolvin, lipoxin, or protectin. In embodiments, the AT resolvin, lipoxin, or protectin is selected from the group consisting of AT-RvE1, AT-RvE2, and AT-RvE3. In embodiments, the AT resolvin, lipoxin, or protectin is selected from the group consisting of AT-RvE1, AT-RvD1, AT-RvD2, AT-PD1 and AT-LXA4. In embodiments, the SPM component consists of an E series resolvin; in embodiments, the E series resolvin is selected from RvE1, RvE2, RvE3, AT-RvE1, AT-RvE2, and AT-RvE3. In embodiments, the SPM component consists of RvE1, AT-RvE1, LXA4, or AT-LXA4. In embodiments, the SPM component consists of RvE1 or LXA4.

The peptide component may be from 2 to 10 or 2 to 20 amino acids in length, preferably 2, 3, 4, or 5 amino acids in length. The peptide component consists of 2 amino acid residues when X is H, or is a peptide of from 3 to 5, 3 to 10, or 3 to 20 amino acid residues where X is CO—Z.

Each amino acid moiety of the peptide component may, independently, comprise or consist of a single natural or non-naturally occurring amino acid residue. In embodiments, the amino acid residues are independently selected from a residue of glycine, alanine, valine, leucine, isoleucine, serine, cysteine, threonine, methionine, proline, phenylalanine, tyrosine, tryptophan, histidine, lysine, arginine, aspartic acid, glutamic acid, asparagine, and glutamine.

$R^1$ and $R^2$ are each independently unsubstituted $C_1$-$C_{10}$ alkyl including at least one basic function. In embodiments, the basic function is the side chain of an amino acid moiety. In embodiments, the amino acid moiety is selected from lysine, arginine, and glutamine. In embodiments, the basic function is selected from the group consisting of a positively charged primary amine, a positively charged secondary amine, a positively charged tertiary amine, and a positively charged guanidine.

In embodiments, basic function refers to —$NH_3$, —NHC($NH_2^+$)$NH_2$, —$NHR^6R^7$, or —$NR^6R^7R^8$, wherein $R^6$, $R^7$, $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a positively charged amine. In embodiments, the basic function is a primary amine. In embodiments, the basic function is —$NH_3^+$.

In embodiments, X is H and the peptide component consists of a dipeptide of amino acids independently selected from lysine, arginine, and glutamine, or a derivative of one or more of the foregoing.

In embodiments, X is CO—Z, and Z is either a single amino acid residue or a peptide of from 2 to 10 or 2 to 5 amino acid residues, and the peptide component comprises at least one or two amino acids independently selected from lysine, arginine, and glutamine.

In embodiments, X is H and $R^1$ and $R^2$ are each independently selected from —$(CH_2)_3$—NHC($NH_2^+$)$NH_2$, —$(CH_2)_4$—$NH_3^+$, and —$(CH_2)_2$—C(O)$NH_3^+$. In embodiments, $R^1$ and $R^2$ are the same. In embodiments, $R^1$ and $R^2$ are different.

In embodiments, X is CO—Z, and Z is either a single amino acid residue or a peptide of from 2 to 10 or 2 to 5 amino acid residues, and $R^1$ and $R^2$ are each independently selected from —$(CH_2)_3$—NHC($NH_2^+$)$NH_2$, —$(CH_2)_4$—$NH_3^+$, and —$(CH_2)_2$—C(O)$NH_3^+$. In embodiments, $R^1$ and $R^2$ are the same. In embodiments, $R^1$ and $R^2$ are different.

In embodiments, —NHC($NH_2^+$)$NH_2$ is

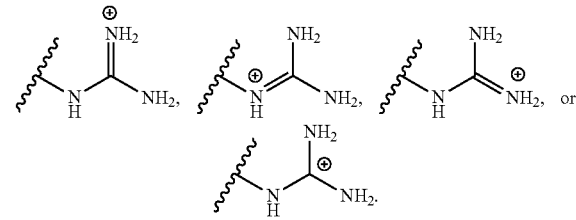

In embodiments, either A or B is absent. Where either A or B is absent, the compound may be referred to as "mono" salt. In embodiments, A and B are both present. Where A and B are both present, the compound may be referred to as a "bis" salt. In one embodiment, A and B are each an SPM, and A and B are the same or different.

In embodiments, A and B are the same or different and each is independently selected from an E series resolvin. In embodiments, the E series resolvin is selected from RvE1, RvE2, RvE3, AT-RvE1, AT-RvE2, and AT-RvE3. In embodiments, A and B are the same and selected from the group consisting of lipoxin A4, protectin DX, resolvin E1, resolvin D2, and aspirin triggered resolvin D1.

In embodiments, the compound of Formula I is a mono or bis SPM lysyl-lysine (lys-lys) compound selected from the group consisting of RvE1 lys-lys, RvE2 lys-lys, RvE3 lys-lys, AT-RvE1 lys-lys, AT-RvE2 lys-lys, and AT-RvE3 lys-lys. In embodiments, the compound of Formula I is a mono or bis SPM lysyl-lysine (lys-lys) compound selected from the group consisting of LXA4 lys-lys, AT-LXA4 lys-lys, RvD1 lys-lys, AT-RvD1 lys-lys, RvE1 lys-lys, AT-RvE1 lys-lys, PDX lys-lys, RvD2 lys-lys and AT-RvD2 lys-lys. In embodiments, the compound of Formula I is a mono or bis SPM lys-lys compound selected from the group consisting of AT-RvD1 lys-lys, AT-RvD2 lys-lys, and AT-LXA4 lys-lys. In embodiments, the compound of Formula I is selected from mono or bis RvE1 lys-lys and mono or bis AT-RvE1 lys-lys. In embodiments, the compound of Formula I selected from mono or bis LXA4 lys-lys and mono or bis AT-LXA4 lys-lys.

Exemplary compounds of the lysyl-lysine embodiment of Formula I are provided in Table 5. In embodiments, the compound of Formula I is selected from the group consisting of Compounds 4, 9, 44, 49, 54, and 59 (E series) of Table 5. In embodiments, a compound of Formula I is selected from the group consisting of Compounds 4, 9, 14, 19, 24, 29, 34, and 39 of Table 5. In embodiments, a compound of Formula I is selected from the group consisting of Compounds 4, 9, 24, 29, 34, and 39 of Table 5. In embodiments, a compound of Formula I is selected from the group consisting of Compounds 4 and 9 (RvE1 and AT-RvE1 embodiments). In embodiments, a compound of Formula I is selected from the group consisting of Compounds 14 and 19 (LXA4 and AT-LXA4 embodiments).

In embodiments, a compound of Formula I is a lysyl-glutamine compound selected from the group consisting of Lysyl-glutamine mono or bis RvE1, Lysyl-glutamine mono or bis RvE2, Lysyl-glutamine mono or bis RvE3, Lysyl-glutamine mono or bis AT-RvE1, Lysyl-glutamine mono or bis AT-RvE2, and Lysyl-glutamine mono or bis AT-RvE3. In embodiments, a compound of Formula I is a lysyl-glutamine compound selected from the group consisting of Lysyl-glutamine mono or bis lipoxin A4 (LXA4), Lysyl-glutamine mono or bis aspirin triggered resolvin D1 (AT-RvD1), Lysyl-glutamine mono or bis resolvin E1 (RvE1), Lysyl-glutamine mono or bis protectin DX (PDX), and Lysyl-glutamine mono or bis resolvin D2 (RvD2).

Formula II Compounds

In embodiments, the disclosure provides compounds of Formula II or an enantiomer, polymorph, solvate, or hydrate thereof:

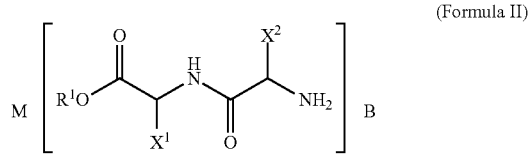

(Formula II)

wherein $R^1$ is H, or absent, $X^1$ and $X^2$ are each independently the side chain of an amino acid residue, M is a positively charged optional molecule, and B is an SPM molecule.

In embodiments, $R^1$ is H and $X^1$ and $X^2$ are the side chain of glycine.

In embodiments, $R^1$ is H and $X^1$ is the side chain of lysine, and $X^2$ is selected from the side chain of valine, the side chain of serine, the side chain of leucine, the side chain of histidine A compound of Formula II consists of at least (i) a dipeptide component and (ii) an SPM component (B), with a positively charged optional molecule (M). The dipeptide component contains $X^1$ and $X^2$ which may be the same or different, and are each the side chain of an amino acid residue. In embodiments, at least one of $X^1$ and $X^2$ is the side chain of an amino acid residue selected from serine, threonine, glycine, alanine, valine, leucine, isoleucine, methionine, and phenylalanine. In embodiments, where one of $X^1$ and $X^2$ is the side chain of an amino acid residue selected from serine, threonine, glycine, alanine, valine, leucine, isoleucine, methionine, and phenylalanine, the remainder of $X^1$ or $X^2$ is the side chain of an amino acid independently selected from lysine, arginine, histidine, aspartate, glutamate, serine, threonine, asparagine, glutamine, cysteine, glycine, proline, alanine, valine, isoleucine, leucine, methionine, phenylalanine, tyrosine, and tryptophan. In embodiments, the remainder is the side chain of lysine. In embodiments, at least one of $X^1$ and $X^2$ is the side chain of glycine, valine, serine, leucine, or histidine, and the remainder is the side chain of lysine.

In embodiments, the SPM component (B) comprises or consists of an E series resolvin. In embodiments of the compound of Formula II, B is selected from the group consisting of RvE1, RvE2, RvE3, AT-RvE1, AT-RvE2, and AT-RvE3. In embodiments, the SPM component (B) comprises or consists of an SPM selected from the group consisting of RvD1, RvD2, RvE1, PDX, and LXA4. In embodiments, the SPM component comprises or consists of an SPM selected from an aspirin-triggered (AT) resolvin, lipoxin, or protectin. In embodiments, the AT resolvin, lipoxin, or protectin is selected from the group consisting of AT-RvE1, AT-RvD1, AT-RvD2, AT-PD1, and AT-LXA4. In embodiments, the SPM component consists of RvE1, AT-RvE1, LXA4, or AT-LXA4. In embodiments, the SPM component consists of RvE1 or LXA4.

The positively charged optional molecule (M) has at least one basic function which forms an ionic bond with the terminal carboxyl of the amino acid component. In embodiments, M is a monovalent metal cation, e.g., $Na^+$, $K^+$, or a molecule having at least one basic function, such as a monovalent amine-based cation, e.g., tri-ethanolamine, or tri-ethylamine, or a basic pharmaceutical compound such as metformin or gabapentin.

As described in more detail below, the compounds of Formula II encompass simple salts of dipeptides and an SPM (Formula IIa), simple metal salts of the dipeptides and an SPM with a monovalent metal (Formula IIb), and simple non-metal salts of the dipeptides and an SPM with a non-metal molecule having at least one basic function (Formula IIc).

The following non-limiting examples of compounds of Formula IIa, IIb, and IIc is provided to illustrate the nature of the compounds described and is not intended to limit the disclosure to the particular compounds depicted below. For any of the following embodiments, A and B are as described above and infra.

Formula IIa Examples

Gly-Gly-SPM which is a compound of Formula II wherein
$R^1$ is H,
$X^1$ and $X^2$ are each H, and
M is absent:

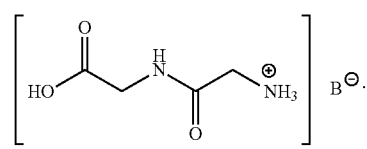

Lys-Lys-SPM which is a compound of Formula II wherein
R¹ is H,
X¹ and X² are each side chain of lysine (butylamine), and
M is absent.

Lys-Val-SPM which is a compound of Formula II wherein
R¹ is each H,
X¹ is the side chain of lysine (butylamine),
X² is the side chain of valine (isopropyl), and
M is absent:

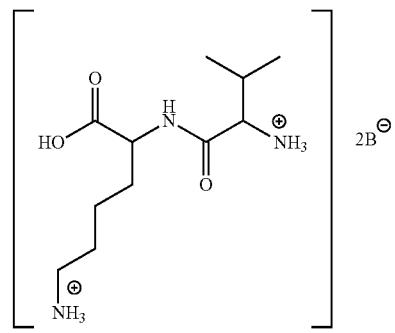

Lys-Ser-SPM which is a compound of Formula II wherein
R¹ is H,
X¹ is the side chain of lysine (butylamine),
X² is the side chain of serine, and
M is absent:

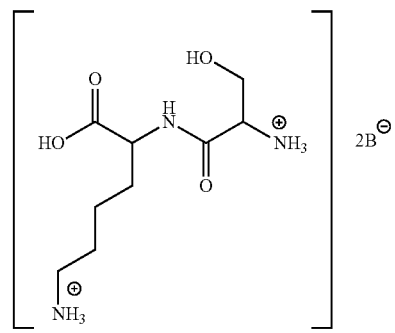

Lys-Gly-SPM which is a compound of Formula II wherein
R¹ is H,
X¹ is the side chain of lysine (butylamine),
X² is the side chain of glycine, and
M is absent:

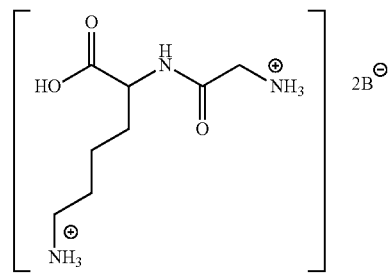

Lys-Leu-SPM which is a compound of Formula II wherein
R¹ is H,
X¹ is the side chain of lysine (butylamine),
X² is the side chain of leucine (isobutyl), and
M is absent:

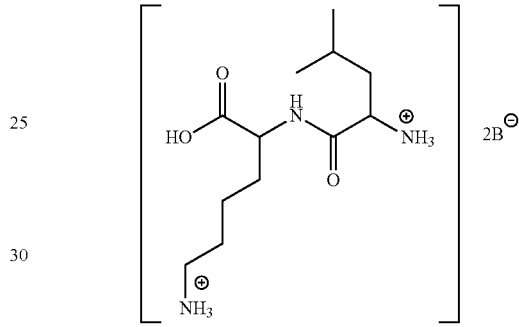

Lys-His-SPM which is a compound of Formula II wherein
R¹ is H,
X¹ is the side chain of lysine (butylamine),
X² is the side chain of histidine (imidazole);
M is absent:

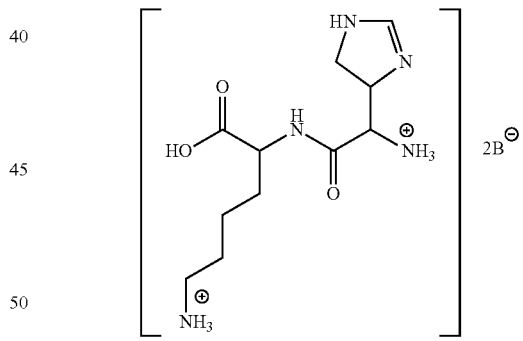

Illustrative structures for three embodiments of Formula IIa, where the dipeptide is Gly-Gly and the SPM is either LXA4, PDX, or AT-RvD1, are shown below:

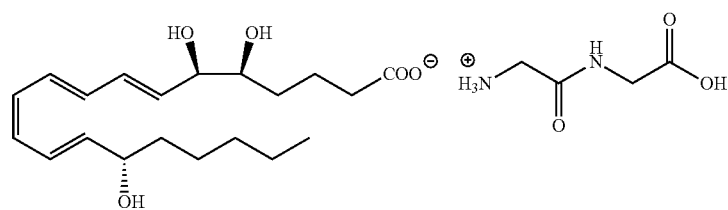

(SPM = LXA4)

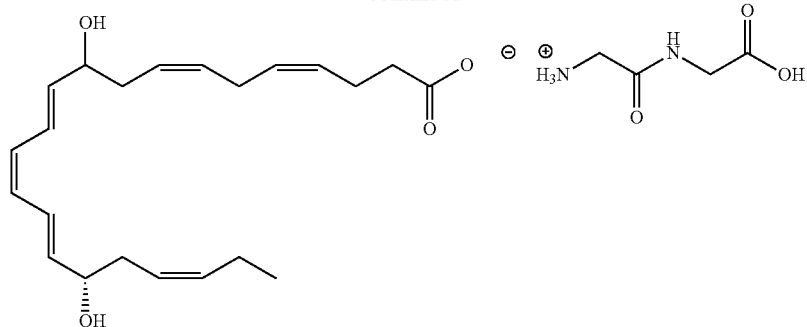

(SPM = PDX)

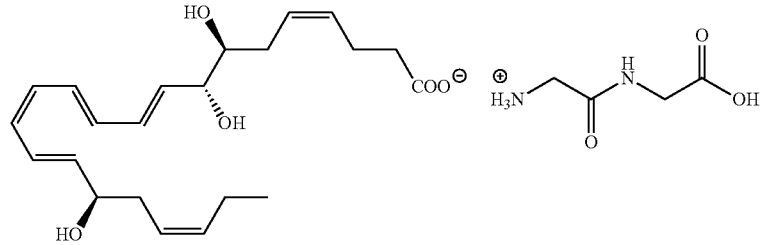

(SPM = AT-RvD1)

Formula IIb Examples

In embodiments, M is a monovalent metal cation such as Na⁺ or K⁺ (Formula IIb). Non-limiting examples of Formula IIb compounds include the following:

Na⁺-Gly-Gly-SPM which is a compound of Formula IIb wherein

R¹ is absent,

X¹ and X² are each H, and;

M is Na:

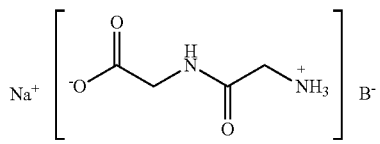

Illustrative structures for three embodiments of Formula IIb, where the SPM is either AT-RvD1, LXA4, or PDX, and M is a sodium cation, are shown below:

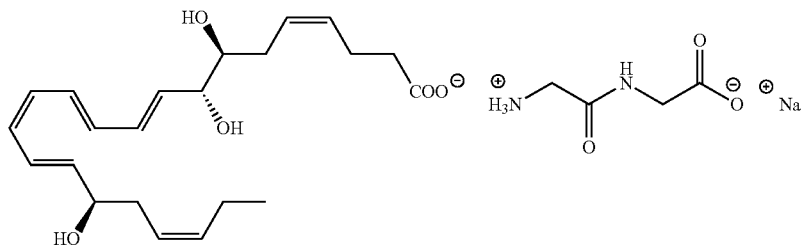

(SPM = AT-RvD1)

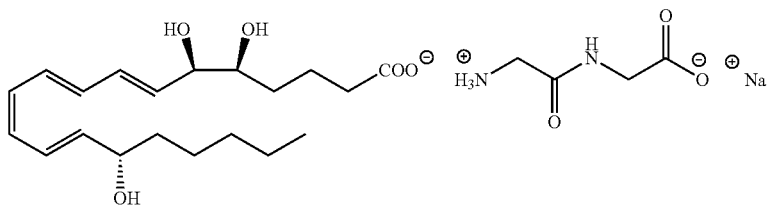

(SPM = LXA4)

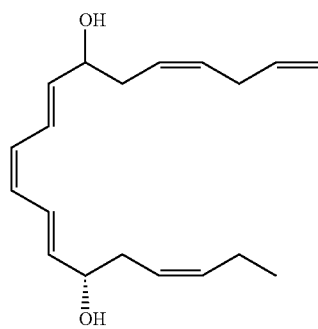
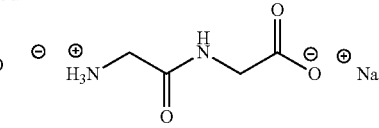

(SPM = PDX)

Formula IIc Examples

In embodiments, M is a non-metal molecule having at least one basic function, such as a monovalent amine-based cation, e.g., tri-ethanolamine, or tri-ethylamine or a basic pharmaceutical compound such as metformin or gabapentin. Non-limiting examples of Formula IIc compounds include the following:

Triethanolamine-Gly-Gly-SPM, which is a compound of Formula II wherein $R_1$ is absent, $X^1$ and $X^2$ are each H, and M is trienthanolamine:

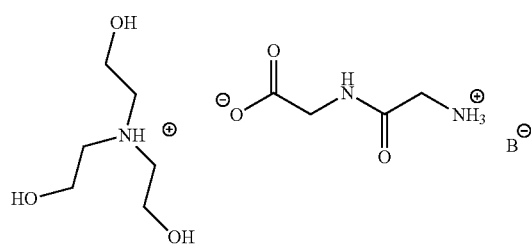

Metformin-Gly-Gly-SPM, which is a compound of Formula II wherein $R^1$ is absent, $X^1$ and $X^2$ are each H, and M is metformin:

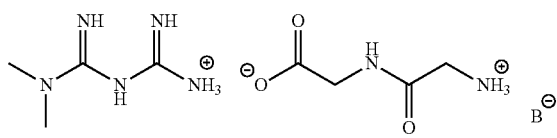

Formula III Compounds

In embodiments, the disclosure provides compounds of Formula III or an enantiomer, polymorph, solvate, or hydrate thereof:

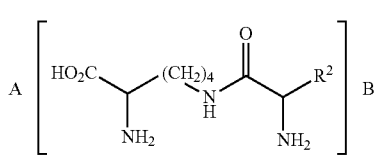

(Formula III)

wherein $R^2$ is a $C_1$-$C_{10}$ alkyl comprising at least one basic function;

A and B are each independently an SPM molecule;

A and B may be the same or different; and either A or B, but not both, may be absent.

In embodiments, $R^2$ is the side chain of an amino acid residue selected from lysine, arginine, and glutamine. In embodiments, $R^2$ is the side chain of lysine. In embodiments, $R^2$ is selected from the group consisting of —$(CH_2)_3$—$NHC(NH_2^+)NH_2$, —$(CH_2)_4$—$NH_3^+$, and —$(CH_2)_2$—$C(O)NH_3^+$. In embodiments, $R^2$ is —$(CH_2)_4$—$NH_3^+$.

In embodiments, the basic function of $R^2$ is selected from the group consisting of a positively charged primary amine, a positively charged secondary amine, a positively charged tertiary amine, and a positively charged guanidine.

In embodiments, the basic function of $R^2$ refers to —$NH_3$, —$NHC(NH_2^+)NH_2$, —$NHR^6R^7$, or —$NR^6R^7R^8$, wherein $R^6$, $R^7$, $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a positively charged amine. In embodiments, the basic function is a primary amine. In embodiments, the basic function is —$NH_3^+$.

In embodiments, $R^2$ is the side chain of lysine, A and B are the same molecule and are selected from an E series resolvin; in embodiments, the E series resolvin is selected from the group consisting of RvE1, RvE2, RvE3, AT-RvE1, AT-RvE2, and AT-RvE3. In embodiments, $R^2$ is the side chain of lysine, A and B are the same molecule and are selected from the group consisting of RvD1, RvD2, RvE1, PDX, LXA4, AT-RvD1, AT-RvD2, AT-PD1, AT-RvE1, and AT-LXA4.

In embodiments, the SPM component (A, B) comprises or consists of an SPM selected from an E series resolvin; in embodiments, the E series resolvin is selected from the group consisting of RvE1, RvE2, RvE3, AT-RvE1, AT- RvE2, and AT-RvE3. In embodiments, the SPM component (A, B) comprises or consists of an SPM selected from the group consisting of RvD1, AT-RvD1, RvD2, AT-RvD2, RvE1, AT-RvE1, PDX, AT-PD1, LXA4 and AT-LXA4. In embodiments, the SPM component consists of RvE1, AT-RvE1, LXA4, or AT-LXA4. In embodiments, the SPM component consists of RvE1 or LXA4.

In embodiments, a compound of Formula III is a mono or bis SPM linear lysyl-lysine (linear lys-lys) compound selected from the group consisting of RvE1 linear lys-lys, RvE2 linear lys-lys, RvE3 linear lys-lys, AT-RvE1 linear lys-lys, AT-RvE2 linear lys-lys, and AT-RvE3 linear lys-lys.

In embodiments, a compound of Formula III is a mono or bis SPM linear lysyl-lysine compound selected from the group consisting of RvE1 linear lys-lys, AT-RvE1 linear lys-lys, LXA4 linear lys-lys, AT-LXA4 linear lys-lys, RvD1 linear lys-lys, AT-RvD1 linear lys-lys, PDX linear lys-lys, and RvD2 linear lys-lys. In embodiments, a compound of Formula III is a mono or bis SPM lysyl-lysine compound selected from the group consisting of AT-RvD1 linear lys-lys, AT-RvD2 linear lys-lys, and AT-LXA4 linear lys-lys. In embodiments, a compound of Formula III is a mono or bis SPM lysyl-lysine compound selected from the group consisting of RvE1 linear lys-lys, AT-RvE1 linear lys-lys, LXA4 linear lys-lys and AT-LXA4 linear lys-lys.

Exemplary compounds of Formula III are provided in Table 5. In embodiments, the compound of Formula III is selected from the group consisting of Compounds 5, 10, 45, 50, 55, and 60 (E series) of Table 5. In embodiments, a compound of Formula III is selected from the group consisting of Compounds 5, 10, 15, 20, 25, 30, 35, and 40 of Table 5. In embodiments, a compound of Formula III is selected from the group consisting of Compounds 5 and 10 (RvE1 and AT-RvE1 embodiments) of Table 5. In embodiments, a compound of Formula III is selected from the group consisting of Compounds 15 and 20 (LXA4 and AT-LXA4 embodiments) of Table 5.

Formula IV Compounds

In embodiments, the disclosure provides compounds of Formula IV or an enantiomer, polymorph, solvate, or hydrate thereof:

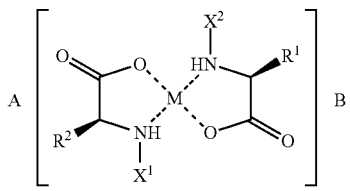

(Formula IV)

wherein

M is a divalent metal;

A and B are each independently an SPM molecule;

A and B may be the same or different;

either A or B, but not both, may be absent;

$R^1$ and $R^2$ are each independently a $C_1$-$C_{10}$ alkyl comprising at least one basic function;

$X^1$ and $X^2$ are each independently H or CO—Z and Z is a peptide comprising 1 to 5 amino acids or a pharmaceutically acceptable salt thereof;

when either A or B is absent:
one of $R^1$, $R^2$ and the two CO—Z's is protonated; or
one of the two H's is positively charged; and the one of $R^1$, $R^2$ and the two CO—Z's that is protonated or the one of the positively charged H's forms an ionic bond with either A or B; and when A and B are both present:
two of $R^1$, $R^2$ and the two CO—Z's are protonated; or
one of $R^1$, $R^2$ and the two CO—Z's is protonated, and one of the two H's is positively charged; and
the two of $R^1$, $R^2$ and the two CO—Z's that are protonated or the one of $R^1$, $R^2$ and the two CO—Z's that is protonated and the positively charged H each respectively form an ionic bond with A and B.

Compounds of Formula IV have two amino acid moieties coordinated around a divalent metal cation as the amino acid component and one or two SPM molecules as the SPM component. In embodiments, the divalent metal cation is $Mg^{2+}$, $Ca^{2+}$, $Mn^{2+}$, $Fe^{2+}$, $Cu^{2+}$, $Co^{2+}$, $Ni^{2+}$, $Mo^{2+}$ or $Zn^{2+}$. In embodiments, the divalent metal cation is $Mg^{2+}$. In embodiments, the divalent metal cation is $Ca^{2+}$. In embodiments, the divalent metal cation is $Zn^{2+}$.

In embodiments, the amino acid component includes or consists of lysine or arginine. In embodiments, the amino acid component includes lysine or arginine. In embodiments, the basic function of $R^1$ and $R^2$ is selected from a primary amine, a secondary amine, a tertiary amine, and a guanidine. In embodiments, basic function refers to —$NH_3$, —$NHC(NH_2^+)NH_2$, —$NHR^6R^7$, or —$NR^6R^7R^8$, wherein $R^6$, $R^7$, $R^8$ are each independently hydrogen, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl; $R^6$ and $R^7$ substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a hydrogen bond donor. In embodiments, the basic function is a positively charged amine.

In embodiments, $R^1$ and $R^2$ are each the side chain of an amino acid residue having a basic function. In embodiments, $R^1$ and $R^2$ are the same and the amino acid residue is lysine or arginine.

In embodiments, $R^1$ and $R^2$ are independently selected from —$(CH_2)_3$—$Y^1$, and —$(CH_2)_4$—$Y^2$, where $Y^1$ and $Y^2$ are each a basic function which may be the same or different.

In embodiments, $R^1$ and $R^2$ are both —$(CH_2)_4$—$Y^2$, and $Y^2$ is —$NH_3^+$.

In embodiments, $R^1$ and $R^2$ are both —$(CH_2)_3$—$Y^1$, and $Y^1$ is —$NHC(NH_2^+)NH_2$.

In embodiments, $R^1$ is —$(CH_2)_3$—$Y^1$, $Y^1$ is —$NHC(NH_2^+)NH_2$, $Y^2$ is —$(CH_2)_4$—$Y^2$, and $Y^2$ is —$NH_3^+$. In embodiments, $R^1$ is —$(CH_2)_4$—$Y^2$, $Y^2$ is —$NH_3$, $R^2$ is —$(CH_2)_3$—$Y^1$, and $Y^1$ is $NHC(NH_2^+)NH_2$.

In embodiments, $X^1$ and $X^2$ are the same and are hydrogen (H). In embodiments, $X^1$ is hydrogen. In embodiments, $X^2$ is hydrogen.

In embodiments, the SPM component (A,B) comprises or consists of an E series resolvin; in embodiments, the E series resolvin is selected from RvE1, RvE2, RvE3, AT-RvE1, AT-RvE2, and AT-RvE3.

In embodiments, the SPM component (A,B) comprises or consists of an SPM selected from the group consisting of RvD1, AT-RvD1, RvD2, AT-RvD2, RvE1, AT-RvE1, PDX, AT-PD1, LXA4 and AT-LXA4. In embodiments, the SPM component consists of RvE1, AT-RvE1, LXA4, or AT-LXA4. In embodiments, the SPM component consists of RvE1 or LXA4.

In embodiments, the compound of Formula IV is a mono or bis SPM magnesium, calcium, or zinc di-lysinate (M-lyslys, or M-di-lysinate) compound selected from the group consisting of RvE1 M-lys-lys, RvE2 M-lys-lys, RvE3 M-lys-lys, AT-RvE1 M-lys-lys, AT-RvE2 M-lys-lys, and AT-RvE3 M-lys-lys.

In embodiments, the compound of Formula IV is a mono or bis SPM magnesium, calcium, or zinc di-lysinate (M-lys-lys, or M-di-lysinate) compound selected from the group consisting of RvD1 M-lys-lys, AT-RvD1 M-lys-lys, RvD2 M-lys-lys, AT-RvD2 M-lys-lys, RvE1 M-lys-lys, AT-RvE1 M-lys-lys, PDX M-lys-lys, LXA4 M-lys-lys, and AT-LXA4 M-lys-lys.

In embodiments, the compound of Formula IV is a mono or bis SPM Mg-di-lysinate compound selected from the group consisting of RvE1 Mg-lys-lys, RvE2 Mg-lys-lys, RvE3 Mg-lys-lys, AT-RvE1 Mg-lys-lys, AT-RvE2 Mg-lys-lys, and AT-RvE3 Mg-lys-lys.

In embodiments, the compound of Formula IV is a mono or bis SPM Ca-di-lysinate compound selected from the group consisting of RvE1 Ca-lys-lys, RvE2 Ca-lys-lys, RvE3 Ca-lys-lys, AT-RvE1 Ca-lys-lys, AT-RvE2 Ca-lys-lys, and AT-RvE3 Ca-lys-lys.

In embodiments, the compound of Formula IV is a mono or bis SPM Zn-di-lysinate compound selected from the group consisting of RvE1 Zn-lys-lys, RvE2 Zn-lys-lys, RvE3 Zn-lys-lys, AT-RvE1 Zn-lys-lys, AT-RvE2 Zn-lys-lys, and AT-RvE3 Zn-lys-lys.

In embodiments, the compound of Formula IV is a mono or bis SPM Mg-di-lysinate compound selected from the group consisting of RvE1 Mg-lys-lys, AT-RvD1 Mg-lys-lys, RvD2 Mg-lys-lys, PDX Mg-lys-lys, and LXA4 Mg-lys-lys.

In embodiments, the compound of Formula IV is a mono or bis RvE1 Mg-lys-lys or a mono or bis AT-RvE1 Mg-lys-lys.

In embodiments, the compound of Formula IV is a mono or bis LXA4 Mg-lys-lys or a mono or bis AT-LXA4 Mg-lys-lys.

In embodiments, the compound of Formula IV is a mono or bis SPM Ca-di-lysinate compound selected from the group consisting of RvE1 Ca-lys-lys, AT-RvE1 Ca-lys-lys, LXA4 Ca-lys-lys and AT-LXA4 Ca-lys-lys.

In embodiments, the compound of Formula IV is a mono or bis RvE1 Ca lys-lys or a mono or bis AT-RvE1 Ca lys-lys.

In embodiments, the compound of Formula IV is a mono or bis LXA4 Ca-lys-lys or a mono or bis AT-LXA4 Ca-lys-lys.

In embodiments, the compound of Formula IV is a mono or bis SPM Zn-di-lysinate compound selected from the group consisting of RvE1 Zn-lys-lys, AT-RvE1 Zn-lys-lys, LXA4 Zn-lys-lys and AT-LXA4 Zn-lys-lys.

In embodiments, the compound of Formula IV is a mono or bis RvE1 Zn lys-lys or a mono or bis AT-RvE1 Zn lys-lys.

In embodiments, the compound of Formula IV is a mono or bis LXA4 Zn-lys-lys or a mono or bis AT-LXA4 Zn-lys-lys.

Exemplary compounds of Formula IV are provided in Table 5. In embodiments, the compound of Formula IV is selected from the group consisting of Compounds 1-3, 6-8, 41-43, 46-48, 51-53, and 56-58 (E series) of Table 5. In embodiments, a compound of Formula IV is selected from the group consisting of Compounds 1-3, 6-8, 11-13, 16-18, 21-23, 26-28, 31-33, and 36-38 of Table 5. In embodiments, a compound of Formula IV is selected from the group consisting of Compounds 1-3 and 6-8 of Table 5 (RvE1 and AT-RvE1 embodiments). In embodiments, a compound of Formula IV is selected from the group consisting of Compounds 11-13 and 16-18 of Table 5 (LXA4 and AT-LXA4 embodiments). In embodiments, a compound of Formula IV is selected from the group consisting of Compounds 21-23 and 26-28 of Table 5 (RvD1 and AT-RvD1 embodiments).

The SPM Component

As used herein, the term "SPM" is used to refer to SPMs such as protectins and resolvins, as well as lipoxins and aspirin-triggered lipid mediators (e.g., aspirin-triggered lipoxins and protectins). These molecules are described, for example in U.S. Pat. Nos. 5,441,951 and 8,119,691 (lipoxins and aspirin-triggered lipoxins), U.S. Pat. No. 6,670,396 (aspirin-triggered lipid mediators), US 2006-0293288 (resolvins), U.S. Pat. Nos. 7,378,444 and 7,595,341 (analogs of lipid mediators derived from omega-3 fatty acids).

Some specific examples of SPM molecules that may used to form the SPM component of the compounds and compositions described here include mediators derived from arachidonic acid (AA) (Table 1), mediators derived from eicosapentaenoic acid (EPA) (Table 2); mediators derived from docosahexaenoic acid (DHA) (Table 3); and aspirin-triggered mediators (Table 4).

In embodiments, the SPM component of a compound or composition described here is selected from an arachidonic acid (AA) derived lipid mediator. In embodiments, the AA derived lipid mediator is selected from lipoxin A4 or lipoxin B4.

In embodiments, the SPM component of a compound or composition described here is selected from an eicosapentaenoic acid (EPA) derived lipid mediator. In embodiments, the EPA derived lipid mediator is selected from lipoxin A5, lipoxin B5, resolvin E1, resolvin E2, and resolvin E3.

In embodiments, the SPM component of a compound or composition described here is selected from a docosahexaenoic acid (DHA) derived lipid mediator. In embodiments, the DHA derived lipid mediator is selected from resolvin D1, resolvin D2, resolvin D3, resolvin D4, resolvin D5, resolvin D6, protectin D1, and protectin DX.

In embodiments, the SPM component of a compound or composition described here is selected from an aspirin-triggered lipid mediator. In embodiments, the aspirin-triggered lipid mediator is selected from 15-epi-lipoxin A4, 15-epi-lipoxin B4, aspirin-triggered resolvin D1, aspirin-triggered resolvin D2, aspirin-triggered resolvin D3, aspirin-triggered resolvin D4, aspirin-triggered resolvin D5, aspirin-triggered resolvin D6, and aspirin-triggered protectin D1. In embodiments, the aspirin-triggered lipid mediator is selected from AT-RvE1, AT-RvE2, and AT-RvE3.

In embodiments, the SPM component of a compound or composition described here is selected from a compound set forth in Table 1, Table 2, Table 3, or Table 4.

TABLE 1

| Arachidonic Acid (AA) and Mediators Derived from AA | | | |
| --- | --- | --- | --- |
| Name | Abbrev. | Formula | Chemical Name |
| Arachidonic acid | AA | $C_{20}H_{32}O_2$ | 5Z,8Z,11Z,14Z-Eicosatetraenoic acid |
| Lipoxin A4 | LXA4 | $C_{20}H_{32}O_5$ | 5S,6R,15S-trihydroxy-7E,9E,11Z,13E-eicosatetraenoic acid |
| Lipoxin B4 | LXB4 | $C_{20}H_{32}O_5$ | 5S,14R,15S-trihydroxy-6E,8Z,10E,12E-eicosatetraenoic acid |

TABLE 2

EPA and Mediators Derived from EPA

| Name | Abbrev. | Formula | Chemical Name |
|---|---|---|---|
| Eicosapentaenoic acid | EPA | $C_{20}H_{30}O_2$ | 5Z,8Z,11Z,14Z,17Z-eicosapentaenoic acid |
| Lipoxin A5 | LXA5 | $C_{20}H_{30}O_5$ | 5S,6R,15S-trihydroxy-7E,9E,11Z,13E,17Z-eicosapentaenoic acid |
| Lipoxin B5 | LXB5 | $C_{20}H_{30}O_5$ | 5S,14R,15S-trihydroxy-6E,8Z,10E,12E,17Z-eicosapentaenoic acid |
| Resolvin E1 | $RvE_1$ | $C_{20}H_{30}O_5$ | 5S,12R,18R-trihydroxy-6Z,8E,10E,14Z,16E-eicosapentaenoic acid |
| Resolvin E2 | $RvE_2$ | $C_{20}H_{30}O_4$ | 5S,18R-dihydroxy-6E,8Z,11Z,14Z,16E-eicosapentaenoic acid |
| Resolvin E3 | $RvE_3$ | $C_{20}H_{30}O_4$ | 17R,18R-dihydroxy-5Z,8Z,11Z,13E,15E-eicosapentaenoic acid |

TABLE 3

DHA and Mediators Derived from DHA

| Name | Abbrev. | Formula | Chemical Name |
|---|---|---|---|
| Docosahexaenoic acid | DHA | $C_{22}H_{32}O_2$ | 4Z,7Z,10Z,13Z,16Z,19Z-docosahexaenoic acid |
| Resolvin D1 | RvD1 | $C_{22}H_{32}O_5$ | 7S,8R,17S-trihydroxy-4Z,9E,11E,13Z,15E,19Z-docosahexaenoic acid |
| Resolvin D2 | RvD2 | $C_{22}H_{32}O_5$ | 7S,16R,17S-trihydroxy-4Z,8E,10Z,12E,14E,19Z-docosahexaenoic acid |
| Resolvin D3 | RvD3 | $C_{22}H_{32}O_5$ | 4S,11R,17S-trihydroxy-5Z,7E,9E,13Z,15E,19Z-docosahexaenoic acid |
| Resolvin D4 | RvD4 | $C_{22}H_{32}O_5$ | 4S,5,17S-trihydroxy-6E,8E,10Z,13E,15E,19Z-docosahexaenoic acid |
| Resolvin D5 | RvD5 | $C_{22}H_{32}O_4$ | 7S,17S-dihydroxy-4Z,8E,10Z,13Z,15E,19Z-docosahexaenoic acid |
| Resolvin D6 | RvD6 | $C_{22}H_{32}O_4$ | 4S,17S-dihydroxy-5E,7Z,10Z,13Z,15E,19Z-docosahexaenoic acid |
| Protectin D1 | PD1 | $C_{22}H_{32}O_4$ | 10R,17S-dihydroxy-4Z,7Z,11E,13E,15Z,19Z-docosahexaenoic acid |
| Protectin DX | PDX | $C_{22}H_{32}O_4$ | 10S,17S-dihydroxy-(4Z,7Z,11E,13Z,15E,19Z)-docosahexaenoic acid |

TABLE 4

Aspirin-Triggered Mediators

| Name | Abbrev. | Formula | Chemical Name |
|---|---|---|---|
| 15-epi-Lipoxin A4 | AT-LXA4 | $C_{20}H_{32}O_5$ | 5S,6R,15R-trihydroxy-7E,9E,11Z,13E-eicosatetraenoic acid |
| 15-epi-Lipoxin B4 | AT-LXB4 | $C_{20}H_{32}O_5$ | 5S,14R,15R-trihydroxy-6E,8Z,10E,12E-eicosatetraenoic acid |
| Aspirin-triggered Resolvin D1 | AT-RvD1 | $C_{22}H_{32}O_5$ | 7S,8R,17R-trihydroxy-4Z,9E,11E,13Z,15E,19Z-docosahexaenoic acid |
| Aspirin-triggered Resolvin D2 | AT-RvD2 | $C_{22}H_{32}O_5$ | 7S,16R,17R-trihydroxy-4Z,8E,10Z,12E,14E,19Z-docosahexaenoic acid |
| Aspirin-triggered Resolvin D3 | AT-RvD3 | $C_{22}H_{32}O_5$ | 4S,11R,17R-trihydroxy-5Z,7E,9E,13Z,15E,19Z-docosahexaenoic acid |
| Aspirin-triggered Resolvin D4 | AT-RvD4 | $C_{22}H_{32}O_4$ | 4S,5,17R-trihydroxy-6E,8E,10Z,13Z,15E,19Z-docosahexaenoic acid |
| Aspirin-triggered Resolvin D5 | AT-RvD5 | $C_{22}H_{32}O_4$ | 7S,17R-dihydroxy-4Z,8E,10Z,13Z,15E,19Z-docosahexaenoic acid |
| Aspirin-triggered Resolvin D6 | AT-RvD6 | $C_{22}H_{32}O_4$ | 4S,17R-dihydroxy-5E,7Z,10Z,13Z,15E,19Z-docosahexaenoic acid |
| Aspirin-triggered Resolvin E1 | $AT-RvE_1$ | $C_{20}H_{30}O_5$ | 5S,12R,18S-trihydroxy-6Z,8E,10E,14Z,16E-eicosapentaenoic acid |
| Aspirin-triggered Resolvin E2 | $AT-RvE_2$ | $C_{20}H_{30}O_4$ | 5S,18S-dihydroxy-6E,8Z,11Z,14Z,16E-eicosapentaenoic acid |
| Aspirin-triggered Resolvin E3 | $AT-RvE_3$ | $C_{20}H_{30}O_4$ | 17R,18S-dihydroxy-5Z,8Z,11Z,13E,15E-eicosapentaenoic acid |
| Aspirin-triggered Protectin D1 | AT-PD1 | $C_{22}H_{32}O_4$ | 10R,17R-dihydroxy-4Z,7Z,11E,13E,15Z,19Z-docosahexaenoic acid |

In certain embodiments, the invention provides a solvate of a compound described herein. A "solvate" refers to a form of salt bound by a non-covalent bond to another molecule (such as a polar solvent). Such solvates are typically crystalline solids having a substantially fixed molar ratio of solute and solvent. When the solvent is water, the solvate formed is a hydrate. Example hydrates include hemihydrates, mono hydrates, dihydrates, etc.

In embodiments, the invention provides a crystalline form of a compound described herein. In one embodiment, the invention provides a polymorph of an ionic salt described herein.

Physical Properties

The compounds described here and compositions comprising same possess advantageous chemical and physical properties compared to the free SPMs. For example, in embodiments a compound described here may be stabilized against chemical degradation compared to the corresponding free SPM. In embodiments, the compounds are stable against chemical degradation, including oxidative degradation. In embodiments, the compounds are stable to degradation induced by exposure to air, oxygen, and humidity as evidenced by a lack of change in physical properties, such as flow characteristics, or in chemical properties, as measured e.g., by spectroscopic techniques such as nuclear magnetic resonance (NMR) or high pressure liquid chromatography (HPLC). In embodiments, the increased stability is evidenced by a lack of chemical degradation after 2, 4, or 8 weeks. In embodiments, a compound described here is stabilized against chemical degradation as evidenced by the lack of degradation products at 2 or 8 weeks, compared to the free SPM.

In embodiments, the compounds are physically solid, free flowing substances suitable for formulation into solid dosage forms such as powders, tablets, capsules or caplets. In addition, the compounds and compositions of the invention can be readily combined, e.g., by physical admixture, with other biologically active agents in a solid dosage form.

Pharmacokinetic Properties

In embodiments, the compounds described here demonstrate highly favorable pharmacokinetic properties. For example, in embodiments, the compounds provide detectable levels of free SPMs in the blood or serum following oral, or parenteral (including via intravenous, intra-arterial, or intramuscular injection) administration, as discussed in more detail in the examples, infra. In embodiments, the compounds of the invention formulated as oral dosage forms deliver higher amounts of the free SPM component to the blood/serum than is achievable with oral administration of, for example, the free SPM itself.

Compositions

The present disclosure provides compositions including one or more of the compounds described herein, including compositions containing mixtures of two or more different compounds described herein. In embodiments, a compound or mixture of compounds described here may be formulated as a pharmaceutical composition, or as a food additive or supplement, meaning that the compound itself and any additives or excipients in the formulation are suitable for administration to humans or animals. In embodiments, the composition is a pharmaceutical composition. In embodiments, the composition is a non-pharmaceutical composition.

A composition including one or more compounds of the invention may be formulated as a solid or liquid dosage form adapted for oral delivery. The oral dosage form may be in the form of a solid, such as a tablet, a capsule containing particulates, liquids, or powders, a lozenge (including liquid-filled), a gum, or a gel. In one embodiment, the dosage form is a solid oral dosage form. In embodiments, the composition is a powder suitable for reconstitution in an aqueous liquid. Such powders may be used, for example, to prepare a liquid suitable for parenteral administration, e.g., via intravenous, intramuscular, or intraperitoneal injection.

In embodiments, a composition including one or more compounds described here may be formulated as a dosage form adapted for rectal delivery. In embodiments, the dosage form adapted for rectal delivery is an ointment, suppository, or enema. In embodiments, the dosage form is adapted for once a day delivery. In embodiments, the solid dosage form is adapted for delivery twice a day.

In embodiments, a composition comprising a compound of any one of Formulas I-IV may be in the form of a unit dose of the compound. In embodiments, the unit dose is in the form of tablet, capsule, suppository, or enema. In embodiments, the unit dose contains from 1 microgram (ug) to 50 milligrams (mg) of the SPM that forms the SPM component of the compound of Formula I, II, III, or IV. In embodiments, the compound is a compound of Formula I or IV. In embodiments, the unit dose contains 1, 5, 10, 25, 50, 100, 250, or 500 micrograms of the SPM. In embodiments, the unit dose contains 1, 5, 10, or 20 milligrams of the SPM.

In embodiments of Formula I, the SPM component of the compound consists of from 50% to 75% by weight of the SPM. In an embodiment of Formula I, the compound is a mono SPM salt of lysyl lysine, the SPM is an E series resolvin, and the SPM comprises from 50-60% by weight of the compound. In an embodiment of Formula I, the compound is a bis salt and the SPM comprises from 60-75% by weight of the compound. In accordance with any of the foregoing embodiments, the E series resolvin may be selected from RvE1, RvE2, RvE3, AT-RvE1, AT-RvE2, and AT-RvE3.

In embodiments of Formula I, the SPM component of the compound consists of from 50% to 75% by weight of the SPM. In an embodiment of Formula I, the compound is a mono SPM salt of lysyl lysine, the SPM is selected from RvD1, RvD2, RvE1, PDX, LXA4, AT-PD1, AT-RvD1, AT-RvD2, AT-LXA4, and AT-RvE1, and the SPM comprises from 50-60% by weight of the compound. In an embodiment of Formula I, the compound is a bis salt and the SPM comprises from 60-75% by weight of the compound.

In embodiments of Formula IV, the SPM component of the compound consists of from 50% to 75% by weight of the SPM. In an embodiment of Formula IV, the compound is a bis SPM magnesium di-lysinate (Mg-lys-lys) salt of an E series SPM and the SPM comprises from 60-75% by weight of the compound. In embodiments where the SPM is a mono salt, the SPM comprises from about 50-60% by weight of the compound. In embodiments, the SPM is selected from RvE1, RvE2, RvE3, AT-RvE1, AT-RvE2, and AT-RvE3 and the SPM comprises about 65% by weight of the compound. In embodiments, the SPM is selected from RvE1, RvE2, RvE3, AT-RvE1, AT-RvE2, and AT-RvE3 and the SPM comprises about 70% by weight of the compound.

In embodiments of Formula IV, the SPM component of the compound consists of from 50% to 75% by weight of the SPM. In an embodiment of Formula IV, the compound is a bis SPM magnesium di-lysinate (Mg-lys-lys) salt of an SPM selected from RvD1, RvD2, RvE1, PDX, LXA4, AT-PD1, AT-RvD1, AT-RvD2, AT-LXA4, and AT-RvE1 and the SPM comprises from 60-75% by weight of the compound. In embodiments where the SPM is a mono salt, the SPM comprises from about 50-60% by weight of the compound.

In embodiments, the SPM is RvE1 or AT-RvE1 and the SPM comprises about 65% by weight of the compound. In embodiments, the SPM is RvD1, RvD2, AT-RvD1, or AT-RVD2 and the SPM comprises about 70% by weight of the compound.

The compounds described here may be formulated alone or in combination with one or more additional active pharmaceutical ingredients (API) or biologically active agents. Also provided are compositions including one or more of the compounds described herein, or mixtures of same, along with a second active agent. In embodiments the second active agent is a biologically active agent or an active pharmaceutical ingredient (API). In embodiments, a compound described here is formulated with one or more additional APIs or biologically active agents in a single dosage form. In embodiments, the dosage form is a solid or liquid dosage form. In embodiments, the solid dosage form is a powder suitable for reconstitution in aqueous media. In embodiments, the solid dosage form is an ointment, suppository, or enema.

Depending on the nature of the compounds and excipients making up the compositions described here, the composition may be suitable for pharmaceutical or veterinary use, or for use a dietary additive or supplement, or any combination of these uses. To the extent the various compositions are discussed in the following sections as "pharmaceutical compositions" or "additives and supplements" these terms are not meant to be limiting, only descriptive.

The compositions described here may be formulated using one or more suitable excipients or carriers. A suitable excipient or carrier is one suitable for human or animal use. The term "excipient" refers to an additive that serves some purpose in the composition other than a carrier, for example as a stabilizer, taste masking agent (e.g., a sweetener), solubilizing agent, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures thereof.

A suitable excipient or carrier is typically a pharmaceutically acceptable carrier or excipient for use in animals or humans (or both). The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the ionic salt of the invention is formulated for delivery. Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

The compounds described here may be formulated in any suitable form and for any suitable intended route of administration. Typically, the dosage form is at least in part determined by the intended route of administration. In embodiments, a compound described here is formulation for administration by an oral, rectal, or parenteral route.

In one embodiment, the dosage form is a liquid suitable for administration to the eye. The formulation may be a solution, suspension, or gel suitable for ocular administration, e.g., suitable for topical administration to the eye, also referred to as an ophthalmic formulation.

In one embodiment, the ophthalmic formulation is an aqueous formulation. In one embodiment, the ophthalmic formulation comprises one or more of glycerin, hypromellose, propylene glycol or polyethylene glycol. In one embodiment, the ophthalmic formulation further comprises one or more of polysorbate 80, carbomer copolymer type A, purified water, sodium hydroxide, ascorbic acid, benzalkonium chloride, boric acid, dextrose, disodium phosphate, glycine, magnesium chloride, potassium chloride, sodium borate, sodium chloride, sodium citrate, sodium lactate, edetate disodium, hydrochloric acid, sodium hydroxide, aminornethylpropanol, hydroxypropyl guar, polyquaternium-I, or sorbitol.

In one embodiment, the ophthalmic formulation comprises one or more of surfactants, tonicity agents, buffers, preservatives, co-solvents and viscosity building agents. Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Preferably, the tonicity agent is present in an amount sufficient to cause the final composition to have an ophthalmically acceptable osmolality (generally about 150-450 mOsm, preferably 250-350 mOsm). An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers.

In embodiments, the composition is a pharmaceutical composition including a compound described herein, or any mixture thereof, and optionally a pharmaceutically acceptable carrier and/or excipient. In embodiments, the composition further comprises an additional active agent, such as an API, as described below.

In one embodiment is provided a solid dosage form including a compound of the invention in physical admixture with one or more additional active pharmaceutical ingredients (APIs). In embodiments, the one or more additional APIs is an antihyperlipidemic agent, an anti-diabetic agent, an anti-epileptic agent, or an anti-inflammatory agent. In one embodiment the API is an antihyperlipidemic agent or an anti-diabetic agent. In one embodiment, the antihyperlipidemic agent is selected from the group consisting of an HMG CoA enzyme inhibitor (e.g., a statin), a cholesterol absorption inhibitor, and a cholesterol esterase transfer protein (CETP) inhibitor. In one embodiment, the antihyperlipidemic agent is a statin. In one embodiment, the statin is selected from the group consisting of atorvastatin, risuvostatin, simvastatin, pravastatin, and pharmaceutically acceptable salts or prodrugs thereof. In one embodiment, the statin is present in an amount ranging from 5 mg to 100 mg. In one embodiment, the statin is pravastatin. In one embodiment, the antihyperlipidemic agent is a cholesterol absorption inhibitor. In one embodiment, the cholesterol absorption inhibitor is ezetimibe, also known as Zetia. In one embodiment, the antihyperlipidemic agent is a CETP inhibitor. In one embodiment, the CETP inhibitor is anacetrapib, or a hydrate, or solvate thereof.

The pharmaceutical compositions including a compound described here, and mixtures thereof, are useful in methods of treating various diseases and disorders that are responsive to treatment with SPMs, their derivatives, and analogs. These uses are described in more detail infra.

Enteral Formulations

In embodiments, a pharmaceutical composition including a compound described here, and mixtures thereof, is formulated as an enteral dosage form. In embodiments, the enteral dosage form is selected from an oral or rectal formulation. The oral formulation may be in the form of e.g., a tablet, solution, suspension, or emulsion. The rectal formulation may be in the form of e.g., an ointment, suppository, or enema.

Parenteral Formulations

In embodiments, a pharmaceutical composition including a compound described here, and mixtures thereof, is formulated as a parenteral dosage form. In embodiments, the parenteral dosage form is selected from an intravenous dosage form, an intra-arterial dosage form, or an intramuscular dosage form. In accordance with any of these embodiments, the dosage form may be in the form of a clear aqueous solution or in the form of a lyophilized solid, e.g., contained in container, such as a vial or an ampule which is suitable for reconstitution with a specified amount of sterile water or aqueous buffer for administration by a parenteral route, e.g., intravenous, intra-arterial, or an intramuscular.

Ophthalmic Formulations

In embodiments, the compounds described herein are useful for treating or ameliorating one or more symptoms of an ocular disease or disorder, as described in more detail below. Accordingly, the invention provides compounds of any one of Formulas I-VI in a pharmaceutical composition suitable for topical administration to the eye, also referred to as an ophthalmic formulation. The formulation may be a solution, suspension, or gel suitable for ocular administration.

In one embodiment, the ophthalmic formulation is an aqueous formulation. In one embodiment, the ophthalmic formulation comprises one or more of glycerin, hypromellose, propylene glycol or polyethylene glycol. In one embodiment, the ophthalmic formulation further comprises one or more of polysorbate 80, carbomer copolymer type A, purified water, sodium hydroxide, ascorbic acid, benzalkonium chloride, boric acid, dextrose, disodium phosphate, glycine, magnesium chloride, potassium chloride, sodium borate, sodium chloride, sodium citrate, sodium lactate, edetate disodium, hydrochloric acid, sodium hydroxide, aminomethylpropanol, hydroxypropyl guar, polyquaternium-I, or sorbitol.

In one embodiment, the ophthalmic formulation comprises one or more of surfactants, tonicity agents, buffers, preservatives, co-solvents and viscosity building agents. Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Preferably, the tonicity agent is present in an amount sufficient to cause the final composition to have an ophthalmically acceptable osmolality (generally about 150-450 mOsm, preferably 250-350 mOsm). An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the fatty acid salts of the invention.

Examples or artificial tears compositions useful as artificial tears carriers include, but are not limited to, commercial products, such as Tears Naturale™, Tears Naturale™, Tears Naturale Free™, and Bion Tears™. (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Gionek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as polyvinyl alcohol, polyvinylpyrrolidone, povidone and carbomers, such as carbomer 934P, carbomer 941, carbomer 940, carbomer 974P.

Examples of viscosity enhancing agents include, but are not limited to polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears will exhibit a viscosity of 1 to 400 centipoises ("cps"). Topical ophthalmic products are typically packaged in multidose form. Preservatives may be required to prevent microbial contamination during use. Suitable preservatives include benzalkonium chloride, chlorobutanol, benzododecinium bromide, methyl paraben, propyl paraben, phenyl-ethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Other wetting agents, emulsifiers and lubricants, such as sodium lauryl sulfate and magnesium stearate, as well as coloring agents, release agents, coating agents, and perfumingagents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

A contact lens may optionally be used to allow for extravasation of vasoactive substance over a more prolonged time period. Vasoactive substances such as Thrombin and Thromboxane A may further induce increase in tear volume via venular vasoconstriction and increased perfusion through lacrimal, accessory lacrimal and surface microvessels; where increased paracellular endothelial openings that increase capillary permeability can further enhance this benefit.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers.

Pharmaceutical Uses

The compounds and compositions described here are useful in methods of treating diseases and disorders characterized by excessive inflammation. For example, the compounds and compositions described here are useful in treating chronic diseases characterized by excessive inflammation including gastrointestinal diseases and disorders, infectious diseases, pulmonary and vascular diseases and disorders, metabolic diseases and disorders, and neurological diseases and disorders. Accordingly, the disclosure provides a method of treating a disease or disorder characterized by excessive inflammation, the method comprising administering to a subject in need thereof, preferably a human subject, an amount of a compound of Formula I, II, III, IV effective to treat the disease or disorder. In accordance with any of the embodiments of the methods described here, the compound may be administered in the form of a pharmaceutical composition, or a veterinary composition, or a nutritional additive or supplement.

In embodiments, the disclosure provides a method of treating a gastrointestinal disease or disorder selected from the group consisting of inflammatory bowel disease (IBD), ulcerative colitis, Crohn's disease, proctitis, pouchitis, Crohn's disease of the pouch, eosinophilic colitis, lymphocytic colitis, collagenous colitis, diversion colitis, chemical colitis, ischemic colitis, infectious colitis, pseudomembranous colitis and indeterminate colitis, the method comprising administering an amount of a Compound of Formulas I-IV, effective to treat the disease or disorder. In embodiments, the disease or disorder is an IBD-related disease or disorder selected from ulcerative colitis, Crohn's disease, proctitis, pouchitis, Crohn's disease of the pouch, eosinophilic colitis, lymphocytic colitis, collagenous colitis, diversion colitis, chemical colitis, and ischemic colitis. In embodiments, the IBD-related disease or disorder is ulcerative colitis or Crohn's disease. In embodiments, the IBD-related disease or disorder is pouchitis.

In embodiments, the disclosure provides a method of treating a gastrointestinal disease or disorder selected from the group consisting of bowel obstruction, chronic pancreatitis, colitis, colon cancer, congenital gastrointestinal anomalies, gastroschisis, high-output fistula, parenteral nutrition associated liver disease, postoperative ileus (POI), postoperative intestinal inflammation, short bowel syndrome, and sporadic polyposis.

In embodiments, the gastrointestinal disease or disorder is an IBD related disease or disorder as described above. In embodiments, the disclosure provides a method of treating the IBD related disease or disorder by administering to a human patient in need thereof a compound of Formulas I-IV. In embodiments, the compound is a compound of Formula I or IV.

In embodiments of the methods described here, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3. In embodiments, the compound is selected from the group consisting of mono or bis RvE1 lysyl lysine, mono or bis AT-RvE1 lysyl lysine, mono or bis RvE2 lysyl lysine, mono or bis AT-RvE2 lysyl lysine, mono or bis RvE3 lysyl lysine, and mono or bis AT-RvE3 lysyl lysine.

In embodiments, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a lysyl-lysine dipeptide of Formula I where A and B are the same and are selected from an E series resolvin; in embodiments, the E series resolvin is selected from RvE1, RvE2, RvE3, AT-RvE1, AT-RvE2, and AT-RvE3, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments of the methods described here, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3. In embodiments, the compound is selected from the group consisting of mono or bis RvE1 linear lysyl lysine, mono or bis AT-RvE1 linear lysyl lysine, mono or bis RvE2 linear lysyl lysine, mono or bis AT-RvE2 linear lysyl lysine, mono or bis RvE3 linear lysyl lysine, and mono or bis AT-RvE3 linear lysyl lysine.

In embodiments, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a linear lysyl-lysine dipeptide of Formula III where A and B are the same and are selected from an E series resolvin; in embodiments, the E series resolvin is selected from RvE1, RvE2, RvE3, AT-RvE1, AT-RvE2, and AT-RvE3, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments of the methods described here, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3. In embodiments, the compound is selected from the group consisting of mono or bis RvE1 Mg-di-lysinate, mono or bis AT-RvE1 Mg-di-lysinate, mono or bis RvE2 Mg-di-lysinate, mono or bis AT-RvE2 Mg-di-lysinate, mono or bis RvE3 Mg-di-lysinate, and mono or bis AT-RvE3 Mg-di-lysinate.

In embodiments, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a magnesium, calcium, or zinc di-lysinate of Formula IV where A and B are the same and are selected from an E series resolvin; in embodiments, the E series resolvin is selected from RvE1, RvE2, RvE3, AT-RvE1, AT-RvE2, and AT-RvE3, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments of the methods described here, the compound administered is selected from a lysyl-lysine dipeptide of Formula I where A and B are the same and are selected from the group consisting of RvD1, RvD2, RvE1, PDX, LXA4, AT-RvD1, AT-RvD2, AT-LXA4, and AT-RvE1. In embodiments, the compound is selected from the group consisting of mono or bis RvE1 lysyl lysine, mono or bis AT-RvE1 lysyl lysine, mono or bis LXA4 lysyl lysine, mono or bis AT-LXA4 lysyl lysine, mono or bis RvD1 lysyl lysine, mono or bis AT-RvD1 lysyl lysine, mono or bis RvD2 lysyl lysine, mono or bis AT-RvD2 lysyl lysine, mono or bis PDX lysyl lysine. In embodiments, the compound is selected from the group consisting of mono or bis RvE1 lysyl lysine, mono or bis AT-RvE1 lysyl lysine, mono or bis LXA4 lysyl lysine, and mono or bis AT-LXA4 lysyl lysine.

In embodiments, the compound administered is selected from a lysyl-lysine dipeptide of Formula I where A and B are the same and are selected from the group consisting of RvE1, LXA4, AT-LXA4, and AT-RvE1, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a lysyl-lysine dipeptide of Formula I where A and B are the same and are selected from the group consisting of RvE1, LXA4, AT-LXA4, and AT-RvE1, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a lysyl-lysine dipeptide of Formula I where A and B are the same and are selected from the group consisting of RvE1, LXA4, AT-LXA4, and AT-RvE1, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a lysyl-lysine dipeptide of Formula I where A and B are the same and are selected from the group consisting of RvE1, LXA4, AT-LXA4, and AT-RvE1, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a lysyl-lysine dipeptide of Formula I where A and B are the same and are selected from the group consisting of RvE1, LXA4, AT-LXA4, and AT-RvE1, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments of the methods described here, the compound administered is selected from a linear lysyl-lysine dipeptide of Formula III where A and B are the same and are selected from the group consisting of RvD1, RvD2, RvE1, PDX, LXA4, AT-RvD1, AT-RvD2, AT-LXA4, and AT-RvE1. In embodiments, the compound is selected from the group consisting of mono or bis RvE1 linear lysyl lysine, mono or bis AT-RvE1 linear lysyl lysine, mono or bis LXA4 linear lysyl lysine, mono or bis AT-LXA4 linear lysyl lysine, mono or bis RvD1 linear lysyl lysine, mono or bis AT-RvD1 linear lysyl lysine, mono or bis RvD2 linear lysyl lysine, mono or bis AT-RvD2 linear lysyl lysine, mono or bis PDX linear lysyl lysine. In embodiments, the compound is selected from the group consisting of mono or bis RvE1 linear lysyl lysine, mono or bis AT-RvE1 linear lysyl lysine, mono or bis LXA4 linear lysyl lysine, and mono or bis AT-LXA4 linear lysyl lysine.

In embodiments, the compound administered is selected from a linear lysyl-lysine dipeptide of Formula III where A and B are the same and are selected from the group consisting of RvE1, LXA4, AT-LXA4, and AT-RvE1, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a linear lysyl-lysine dipeptide of Formula III where A and B are the same and are selected from the group consisting of RvE1, LXA4, AT-LXA4, and AT-RvE1, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a linear lysyl-lysine dipeptide of Formula III where A and B are the same and are selected from the group consisting of RvE1, LXA4, AT-LXA4, and AT-RvE1, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a linear lysyl-lysine dipeptide of Formula III where A and B are the same and are selected from the group consisting of RvE1, LXA4, AT-LXA4, and AT-RvE1, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a linear lysyl-lysine dipeptide of Formula III where A and B are the same and are selected from the group consisting of RvE1, LXA4, AT-LXA4, and AT-RvE1, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments of the methods described here, the compound administered is selected from a magnesium, calcium, or zinc di-lysinate of Formula IV where A and B are the same and are selected from the group consisting of RvD1, RvD2, RvE1, PDX, LXA4, AT-RvD1, AT-RvD2, AT-LXA4, and AT-RvE1. In embodiments, the compound is selected from the group consisting of mono or bis RvE1 Mg-di-lysinate, mono or bis AT-RvE1 Mg-di-lysinate, mono or bis LXA4 Mg-di-lysinate, mono or bis AT-LXA4 Mg-di-lysinate, mono or bis RvD1 Mg-di-lysinate, mono or bis AT-RvD1 Mg-di-lysinate, mono or bis RvD2 Mg-di-lysinate, mono or bis AT-RvD2 Mg-di-lysinate and mono or bis PDX Mg-di-lysinate. In embodiments, the compound is selected from the group consisting of mono or bis RvE1 Mg-di-lysinate, mono or bis AT-RvE1 Mg-di-lysinate, mono or bis LXA4 Mg-di-lysinate, and mono or bis AT-LXA4 Mg-di-lysinate.

In embodiments, the compound administered is selected from a magnesium, calcium, or zinc di-lysinate of Formula IV where A and B are the same and are selected from the group consisting of RvE1, LXA4, AT-LXA4, and AT-RvE1, and the disease or disorder is an IBD related disease or disorder as described above. In embodiments, the IBD-related disease or disorder is ulcerative colitis or Crohn's disease. In embodiments, the IBD-related disease or disorder is pouchitis.

In embodiments, the compound administered is selected from a magnesium, calcium, or zinc di-lysinate of Formula IV where A and B are the same and are selected from the group consisting of RvE1, LXA4, AT-LXA4, and AT-RvE1, and the disease or disorder is a gastrointestinal disease or disorder selected from eosinophilic esophagitis, Behcet's disease, irritable bowel syndrome, Celiac disease, intestinal mucositis, diverticulitis, and short bowel syndrome. In embodiments, the gastrointestinal disease or disorder is intestinal mucositis.

In embodiments, the compound administered is selected from a magnesium, calcium, or zinc di-lysinate of Formula IV where A and B are the same and are selected from the group consisting of RvE1, LXA4, AT-LXA4, and AT-RvE1, and the disease or disorder is a dermatological disease or disorder selected from dermatitis, diabetic wound, eczema, pruritus, healing wound, acne, and steroid-induced rosacea. In embodiments, the dermatological disease or disorder is selected from dermatitis, eczema, pruritus, acne, and steroid-induced rosacea.

In embodiments, the compound administered is selected from a magnesium, calcium, or zinc di-lysinate of Formula IV where A and B are the same and are selected from the group consisting of RvE1, LXA4, AT-LXA4, and AT-RvE1, and the disease or disorder is an inflammatory disease or disorder selected from asthma, ischemia reperfusion injury, lyme arthritis, periodontitis, peritonitis, psoriasis, rheumatoid arthritis, scleroderma, oral mucositis, stomatitis, chelitis, glossitis, Sjogren's syndrome and systemic inflammatory response syndrome. In embodiments, the inflammatory disease or disorder selected from asthma, psoriasis, scleroderma, and oral mucositis.

In embodiments, the compound administered is selected from a magnesium, calcium, or zinc di-lysinate of Formula IV where A and B are the same and are selected from the group consisting of RvE1, LXA4, AT-LXA4, and AT-RvE1, and the disease or disorder is a neurological disease or disorder selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

Additional uses are described infra.

In the context of the methods described here, the term "treating" or "effective to treat" may refer to the amelioration or stabilization of one or more symptoms associated with the disease or disorder being treated. The term "treating" may also encompass the management of a disease or disorder, referring to the beneficial effects that a subject derives from a therapy which does not result in a cure of the underlying disease or disorder. The compositions of the invention can also be used in the prevention of certain diseases, disorders, and conditions. In this context, the term "prevention" refers to preventing the recurrence, development, progression or onset of one or more symptoms of the disease, disorder, or condition.

In accordance with the methods described here, a therapeutically effective amount of a compound described herein is administered to a subject, the therapeutically effective amount being an amount of the compound (or mixture of two or more compounds) sufficient to treat the disease or disorder, or sufficient to achieve a desired therapeutic outcome, for example the amelioration or stabilization of one or more symptoms of the disease or disorder being treated, or in the context of prevention, the amount sufficient to achieve prevention of the recurrence, development, progression or onset of one or more symptoms of the disease, disorder, or condition.

In the context of any of the methods of the present invention, the subject may be a human or a non-human mammal. The non-human mammal may be, for example, a non-human primate, a dog, cat, a rodent (e.g., a mouse, a rat, a rabbit), a horse, a cow, a sheep, a goat, a bird, a chicken, or any other non-human mammal. Preferably, the subject is a human.

In embodiments, the subject is a human subject. In one embodiment, the human is an adult human, a pediatric human, or a geriatric human, as those terms are understood by the medical practitioner, for example as defined by the U.S. Food and Drug Administration.

The compounds or compositions described here can be used as monotherapy or adjunctive therapy. The compositions of the invention can be administered alone or in combination with one or more additional therapeutic agents (i.e., additional APIs) or therapies, for example as part of a therapeutic regimen that includes, e.g., aspects of diet and exercise. In certain embodiments, the methods of the invention include administration of a composition of the invention as the primary therapy. In other embodiments, the administration of a composition of the invention is an adjuvant therapy. In either case, the methods of the invention contemplate the administration of a composition of the invention in combination with one or more additional therapeutic agents and/or therapies for the treatment or prevention of a disease or disorder. The terms "therapy" and "therapies" refer to any method, protocol and/or agent that can be used in the prevention, treatment, management or amelioration of a disease or disorder, or one or more symptoms thereof.

The compounds or compositions described here can also be used in combination therapy. As used herein, "combination therapy" or "co-therapy" includes the administration of a therapeutically effective amount of one or more of the compounds described here as part of a specific treatment regimen intended to provide the beneficial effect from the co-action of the one or more compounds and an additional active agent, for example an additional API or active biological agent as described above. The beneficial effect of the combination includes, but is not limited to, pharmacokinetic or pharmacodynamic co-action resulting from the combination. The beneficial effect of the combination may also relate to the mitigation of toxicity, side effect, or adverse event associated with another agent in the combination. "Combination therapy" is not intended to encompass the administration of two or more compounds as part of separate monotherapy regimens that incidentally and arbitrarily result in a beneficial effect that was not intended or predicted.

Dermatological Conditions and Disorders

In embodiments, the present disclosure provides a method for treating a dermatological condition or disorder in a subject in need thereof by administering to the subject an effective amount of a compound of any one of Formulas I-VI, or mixtures thereof, or a composition comprising same.

In embodiments, the dermatological disorder is dermatitis.

In embodiments, the dermatological condition is a diabetic wound.

In embodiments, the dermatological disorder is eczema.

In embodiments, the dermatological disorder is pruritus.

In embodiments, the dermatological condition is a healing wound.

In embodiments, the dermatological condition is acne.

In embodiments, the dermatological condition is steroid-induced rosacea.

Gastrointestinal Diseases and Disorders

In embodiments, the present disclosure provides a method for treating a gastrointestinal disease or disorder in a subject in need thereof by administering to the subject an effective amount of a compound of any one of Formulas I-VI, or mixtures thereof, or a composition comprising same.

In embodiments, gastrointestinal disease or disorder is selected from IBD, ulcerative colitis, Crohn's disease, proctitis, pouchitis, Crohn's disease of the pouch, eosinophilic colitis, lymphocytic colitis, collagenous colitis, diversion colitis, chemical colitis, ischemic colitis, infectious colitis, pseudomembranous colitis and indeterminate colitis. In embodiments, the gastrointestinal disease or disorder is selected from IBD, ulcerative colitis, and Crohn's disease.

In embodiments, the gastrointestinal disease or disorder is selected from bowel obstruction, chronic pancreatitis, colitis, colon cancer, congenital gastrointestinal anomalies, gastroschisis, high-output fistula, parenteral nutrition associated liver disease, postoperative ileus, postoperative intestinal inflammation, short bowel syndrome, and sporadic polyposis. In embodiments, the gastrointestinal disease or disorder is selected from eosinophilic esophagitis, Behcet's disease, irritable bowel syndrome, celiac disease, Intestinal mucositis, NSAID enteropathies, enteric infections, diverticulosis, diverticulitis, gastritis, pancreatitis, viral gastroenteritis, and Whipple's disease.

In embodiments, the gastrointestinal disease or disorder is postoperative intestinal inflammation, postoperative ileus, or a combination thereof. In embodiments, the gastrointestinal inflammatory disease or disorder is postoperative ileus (POI).

Infectious Diseases and Disorders Caused by an Infectious Agent

In embodiments, the present disclosure provides a method for treating a disease or disorder caused by an infectious agent, such as a bacterium, a fungus, or a virus, in a subject in need thereof by administering to the subject an effective amount of a compound of any one of Formulas I-V, or mixtures thereof, or a composition comprising same.

In embodiments, the disease or disorder is a bacterial infection. In embodiments, the bacterial infection is bacterial pneumonia. In embodiments, the bacterial infection is an *E. coli* infection. In embodiments, the bacterial infection is a *Mycobacterium tuberculosis* infection.

In embodiments, the disease or disorder is a yeast infection. In embodiments, the yeast infection is a *Candida* yeast infection.

In embodiments, the disease or disorder is sepsis. In embodiments, the sepsis is burn wound sepsis.

Inflammatory Disorders

The compounds described here may be particularly useful in the treatment of diseases and disorders having a significant inflammatory component, due to the ability of the SPMs to mediate resolution of inflammation, and the ability of the compounds described here to deliver therapeutically effective amounts of SPMs to the tissue of a subject in need of treatment for inflammation. In addition, the compounds and compositions described here are useful in treating conditions which would benefit from rapid resolution of inflammation. Thus, the compounds and compositions described here are useful in promoting wound healing, including the healing of burn wounds and diabetic wounds. Other conditions which may be treated according to the methods described here include, chronic pancreatitis, dermatitis, peritonitis, dry eye, bacterial infection, adipose tissue inflammation, localized aggressive periodontitis, temporomandibular joint inflammation, arthritis, postoperative pain, postsurgical cognitive decline, endotoxin shock, HSV-keratitis, allograft rejection, and heart ischemia.

In embodiments, the present disclosure provides a method for treating an inflammatory disease or disorder in a subject in need thereof by administering to the subject an effective amount of a compound of any one of Formulas I-VI, or mixtures thereof, or a composition comprising same. In embodiments, the effective amount is effective to treat one or more symptoms of the inflammatory disease or disorder.

In embodiments, the inflammatory disease or disorder is selected from the group consisting of asthma, ischemia reperfusion injury, lyme arthritis, periodontitis, peritonitis, psoriasis, rheumatoid arthritis, scleroderma, and systemic inflammatory response syndrome.

In embodiments, the inflammatory disease or disorder is selected from the group consisting of oral mucositis, stomatitis, chelitis, glossitis, and Sjogren's syndrome.

In embodiments, the inflammatory disease or disorder is osteoarthritis or rheumatoid arthritis.

In embodiments, the inflammatory disease or disorder is adipose tissue inflammation.

In embodiments, the inflammatory disease or disorder is vascular inflammation.

In embodiments, the inflammatory disease or disorder is heart ischemia.

In embodiments, the inflammatory disease or disorder is endometriosis.

In embodiments, the inflammatory disease or disorder is oral mucositis.

In embodiments, the inflammatory disease or disorder is a disease or disorder of the ocular system. In embodiments, the disease or disorder of the ocular system is selected from the group consisting of inflammatory diseases of the eye, dry eye syndrome, macular edema and retinopathy. In embodiments, the method is a method for promoting corneal wound healing.

In embodiments, the method is a method for treating dry eye. Dry eye disease or syndrome is a multifactorial disorder of the tears and ocular surface characterized by symptoms of dryness and irritation. Inflammation is an important component in the development and propagation of dry eye (Stevenson et al., Arch. Ophthalmol., 2012, 130(1), 90-100; Rashid et al., Arch. Ophthalmol, 2008, 126(2), 219-225).

The term "dry eye" refers to inadequate tear production and/or abnormal tear composition. Causes of dry eye disease as defined herein include but are not limited to the following: idiopathic, congenital alacrima, xerophthalmia, lacrimal gland ablation, and sensory denervation; collagen vascular diseases, including rheumatoid arthritis, Wegener's granulomatosis, and systemic lupus erythematosus; Sjogren's syndrome and autoimmune diseases associated with Sjogren's syndrome; abnormalities of the lipid tear layer caused by blepharitis or rosacea; abnormalities of the mucin tear layer caused by vitamin A deficiency; trachoma, diphtheric keratoconjunctivitis; mucocutaneous disorders; aging; menopause; and diabetes. Further, the term "dry eye" includes dry eye after anterior ophthalmic operation such as cataract operation and refractive surgery and that accompanied with allergic conjunctivitis Dry eye symptoms as defined herein may also be provoked by other circumstances, including, but not limited to, the following: prolonged visual tasking; working on a computer; being in a dry environment; ocular irritation; contact lenses, LASIK and other refractive surgeries; fatigue; and medications such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine.

In embodiments, the method further comprises administering a compound described herein with an anti-inflammatory agent. In embodiments, the compound and the anti-inflammatory agent are contained in the same dosage form.

Metabolic Diseases and Disorders

In embodiments, the present disclosure provides a method for treating a metabolic disease or disorder in a subject in need thereof by administering to the subject an effective amount of a compound of any one of Formulas I-V, or mixtures thereof, or a composition comprising same. In embodiments, the subject is a human and the compound is a compound of Formula I or IV.

In embodiments, the metabolic disease or disorder is abnormal glucose metabolism manifesting in diabetes, including type 2 diabetes, or pre-diabetes, insulin resistance, abnormal lipid metabolism manifesting as hypertriglyceridemia, i.e., elevated triglycerides, mixed dyslipidemia, hypercholesterolemia, fatty liver, and combined abnormal glucose and lipid metabolism manifesting in obesity; or a dyslipidemic disorder selected from hypertriglyceridemia, hypercholesterolemia and mixed dyslipidemias.

In embodiments, the metabolic disease or disorder is insulin resistance, mixed dyslipidemia, nonalcoholic steatohepatitis (NASH), type 2 diabetes, primary biliary syndrome, and primary schlerosing cholangitis.

In embodiments, a compound described here is formulated in a single solid dosage form with at least one additional API. In embodiments, the at least one additional API is an antihyperlipidemic agent or an anti-diabetic agent. Antihyperlipidemic agents that may be used include HMG CoA enzyme inhibitors (e.g., statins), cholesterol absorption inhibitors, and cholesterol esterase transfer protein (CETP) inhibitors. In embodiments, the antihyperlipidemic agent is selected from a statin, a cholesterol absorption inhibitor, a CETP inhibitor, and pharmaceutically-acceptable salts and prodrugs of any of the foregoing. The pharmaceutically acceptable salt may be selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, and lactobionate salt.

In embodiments, the antihyperlipidemic agent is a statin. In embodiments, the statin is selected from the group consisting of atorvastatin, risuvostatin, simvastatin, pravastatin, and pharmaceutically acceptable salts and prodrugs of any of the foregoing. In embodiments, the statin is present in an amount ranging from 5 mg to 100 mg. In one embodiment, the statin is pravastatin.

In embodiments, the antihyperlipidemic agent is a cholesterol absorption inhibitor. In one embodiment, the cholesterol absorption inhibitor is ezetimibe, also known as Zetia.

In embodiments, the antihyperlipidemic agent is a CETP inhibitor. In one embodiment, the CETP inhibitor is anacetrapib, or a hydrate, or solvate thereof.

Neurological Disorders

In embodiments, the present disclosure provides a method for treating a neurological disorder in a subject in need thereof by administering to the subject an effective amount of a compound of any one of Formulas I-VI, or mixtures thereof, or a composition comprising same. In embodiments, the compound is a compound of Formula I or IV. In embodiments, the neurological diseases and disorders that may be treated include, without limitation, Alzheimer's disease, peripheral nerve injury, amyotrophic lateral sclerosis, pain, and fibromyalgia. In embodiments, the neurological disease or disorder is selected from postoperative delirium, acute postsurgical pain, fibromyalgia, endometriosis, vulvodynia, chronic lower back pain, treatment or management of pain associated with osteoarthritis, diabetic peripheral neuropathy and musculoskeletal injury or trauma.

In embodiments, the amount is effective to treat one or more symptoms of the neurological disorder.

In embodiments, the neurological disorder is a psychiatric disorder. In embodiments, the psychiatric disorder is selected from attention deficit hyperactivity disorder (ADHD) and depression. In embodiments, the neurological disease or disorder is postoperative cognitive dysfunction (POCD) or postoperative delirium.

The disclosure also provides methods for treating or managing pain. In embodiments, the pain is nociceptive pain and the method comprises administering to a subject in need of treatment for nociceptive pain a pharmaceutical composition comprising an effective amount a compound described here, or mixtures thereof. In embodiments, the methods further comprise administering at least one additional API. In embodiments, the additional API is gabapentin, or a pharmaceutically acceptable salt or prodrug thereof.

In embodiments, the disclosure also provides methods for treating or managing pain associated with inflammation.

In embodiments, the disclosure also provides methods for treating or managing pain associated with fibromyalgia.

In embodiments, the disclosure also provides methods for treating or managing pain associated with endometriosis.

In embodiments, the disclosure also provides methods for treating or managing pain associated with vulvodynia.

In embodiments, the disclosure also provides methods for treating or managing acute postsurgical pain.

In embodiments, the disclosure also provides methods for treating or managing chronic lower back pain.

In embodiments, the disclosure also provides methods for treating or managing pain associated with osteoarthritis.

In embodiments, the disclosure also provides methods for treating or managing pain associated with diabetic peripheral neuropathy.

In embodiments, the disclosure also provides methods for treating or managing pain associated with musculoskeletal injury or trauma.

Pulmonary and Vascular Diseases and Disorders

In embodiments, the present disclosure provides a method for treating a pulmonary disorder in a subject in need thereof by administering to the subject an effective amount of a compound of any one of Formulas I-VI, or mixtures thereof, or a composition comprising same. In embodiments, the subject is human and the compound is a compound of Formula I or IV.

In embodiments, the pulmonary and vascular diseases and disorders that may be treated include, without limitation, pulmonary inflammation, bronchopulmonary dysplasia, also referred to as chronic lung disease of infancy, cystic fibrosis, allergic airway response, acute lung injury, lung injury, idiopathic pulmonary fibrosis, bacterial pneumonia, cigarette smoke-induced lung inflammation, and vascular inflammation.

In embodiments, the pulmonary disorder is selected from acute lung injury, bronchopulmonary dysplasia, also referred to as chronic lung disease of infancy, cystic fibrosis, idiopathic pulmonary fibrosis, lung injury, and pulmonary inflammation.

In embodiments, the pulmonary disorder is bronchopulmonary dysplasia, also referred to as chronic lung disease of infancy.

In embodiments, the pulmonary disorder is cystic fibrosis.

In embodiments, the pulmonary disorder is idiopathic pulmonary fibrosis.

Non-Pharmaceutical Uses

In one embodiment, the invention provides compositions comprising a compound described herein, and mixtures of the same, for a non-pharmaceutical use. e.g., for use as a dietary supplement.

In embodiments, the non-pharmaceutical use may comprise administering to the subject an effective amount of a composition comprising a compound described here, or a mixture of two or more of the compounds described here. In embodiments, the effective amount is an amount effective to maintain, promote, or improve the general health of the subject.

In one embodiment, the composition may be used in a method to counter a dietary deficiency or nutritional disorder in a subject. In one embodiment, the composition may be used in a method for maintaining, promoting, or improving the general health of a subject.

In one embodiment, the method is a method for improving heart health.

In one embodiment, the method is a method for improving joint health.

In one embodiment, the method is a method for improving eye health.

In one embodiment, the method is a method for improving cognitive health.

Combination Therapies

In the context of the methods described above, the method may further comprise administering a compound described herein as a combination therapy, with one or more additional APIs or non-pharmaceutical agents intended to treat or ameliorate one or more symptoms of the disease or disorder, or to provide additional non-pharmaceutical benefits as described above. In embodiments, a compound described herein may be administered together with the at least one additional API or non-pharmaceutical agent, or separately from the additional API or non-pharmaceutical agent. Where delivery is together, a composition of the invention may be delivered in the same dosage form as the additional API or non-pharmaceutical agent, or in a different dosage form. One of the advantages of the present invention, as discussed above, is the ease of formulating the compositions described herein with additional APIs or non-pharmaceutical agents and excipients in a single solid dosage form due to their form as a free flowing powder that is chemically and physically stable (as opposed to the relatively unstable oily liquid form of free SPMs and their esters).

The invention is further described in the following examples, which do not limit the scope of the invention described in the claims.

The structures of exemplary compounds of Formulas I and IV are shown in Table 5 below.

TABLE 5

Structures of Representative Compounds of Formulas I and IV

| Cmpd # | Name | Structure |
|---|---|---|
| 1 | RvE1-MgLys | |

TABLE 5-continued

Structures of Representative Compounds of Formulas I and IV

| # | Name | |
|---|---|---|
| 2 | RvE1-CaLys | |
| 3 | RvE1-ZnLys | |
| 4 | RvE1-LysLys | |
| 5 | RvE1-LysLys (linear) | |
| 6 | AT(18S)-RvE1-MgLys | |
| 7 | AT(18S)-RvE1-CaLys | |
| 8 | AT(18S)-RvE1-ZnLys | |
| 9 | AT(18S)-RvE1-LysLys | |
| 10 | AT(18S)-RvE1-LysLys (linear) | |

TABLE 5-continued

Structures of Representative Compounds of Formulas I and IV

| 11 | LxA4-MgLys | | |
| 12 | LxA4-CaLys | | |
| 13 | LxA4-ZnLys | | |
| 14 | LxA4-LysLys | | |
| 15 | LxA4-LysLys (linear) | | |
| 16 | AT(15e)-LxA4-MgLys | | |
| 17 | AT(15e)-LxA4-CaLys | | |
| 18 | AT(15e)-LxA4-ZnLys | | |

TABLE 5-continued

Structures of Representative Compounds of Formulas I and IV

| | | | |
|---|---|---|---|
| 19 | AT(15e)-LxA4-LysLys | | |
| 20 | AT(15e)-LxA4-LysLys (linear) | | |
| 21 | RvD1-MgLys | | |
| 22 | RvD1-CaLys | | |
| 23 | RvD1-ZnLys | | |
| 24 | RvD1-LysLys | | |
| 25 | RvD1-LysLys (linear) | | |

TABLE 5-continued

Structures of Representative Compounds of Formulas I and IV

| 26 | AT(17e)-RvD1-MgLys | | |
| 27 | AT(17e)-RvD1-CaLys | | |
| 28 | AT(17e)-RvD1-ZnLys | | |
| 29 | AT(17e)-RvD1-LysLys | | |
| 30 | AT(17e)-RvD1-LysLys (linear) | | |
| 31 | RvD2-MgLys | | |
| 32 | RvD2-CaLys | | |

TABLE 5-continued

Structures of Representative Compounds of Formulas I and IV

| 33 | RvD2-ZnLys | | |
| 34 | RvD2-LysLys | | |
| 35 | RvD2-LysLys (linear) | | |
| 36 | PDX-MgLys | | |
| 37 | PDX-CaLys | | |
| 38 | PDX-ZnLys | | |
| 39 | PDX-LysLys | | |
| 40 | PDX-LysLys (linear) | | |
| 41 | RvE2-MgLys | | |

TABLE 5-continued

Structures of Representative Compounds of Formulas I and IV

| 42 | RvE2-CaLys |
| 43 | RvE2-ZnLys |
| 44 | RvE2-LysLys |
| 45 | RvE2-LysLys (linear) |
| 46 | AT-RvE2-MgLys |
| 47 | AT-RvE2-CaLys |
| 48 | AT-RvE2-ZnLys |
| 49 | AT-RvE2-LysLys |

TABLE 5-continued

Structures of Representative Compounds of Formulas I and IV

| 50 | AT-RvE2-LysLys (linear) |
| 51 | RvE3-MgLys |
| 52 | RvE3-CaLys |
| 53 | RvE3-ZnLys |
| 54 | RvE3-LysLys |
| 55 | RvE3-LysLys (linear) |
| 56 | AT-RvE3-MgLys |
| 57 | AT-RvE3-CaLys |

TABLE 5-continued

Structures of Representative Compounds of Formulas I and IV

| | | |
|---|---|---|
| 58 | AT-RvE3-ZnLys | |
| 59 | AT-RvE3-LysLys | |
| 60 | AT-RvE3-LysLys (linear) | |

| Cmpd # | Structure |
|---|---|
| 1 | 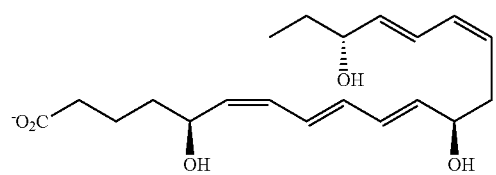 |
| 2 | 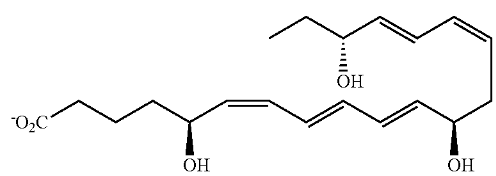 |
| 3 | 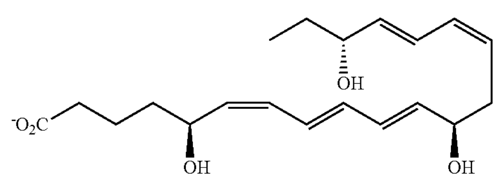 |
| 4 | 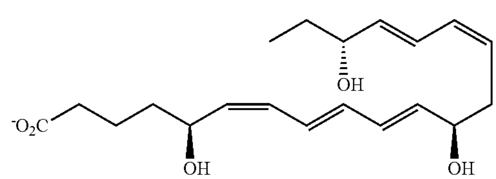 |
| 5 | 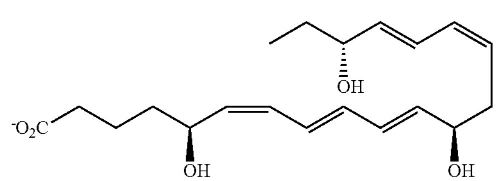 |

TABLE 5-continued
Structures of Representative Compounds of Formulas I and IV
6 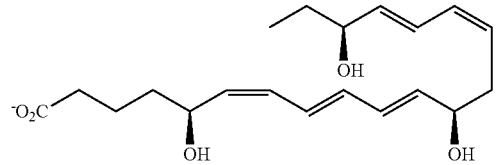
7 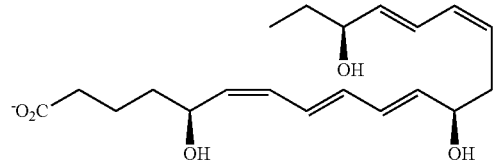
8 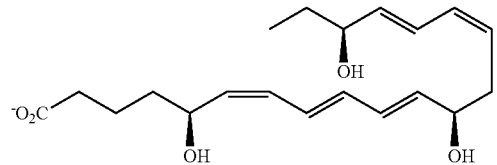
9 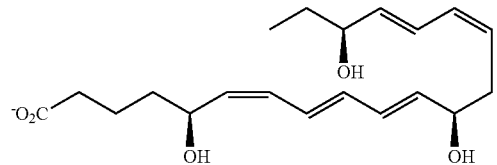
10 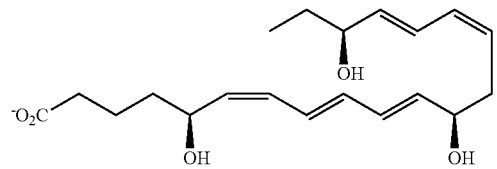
11 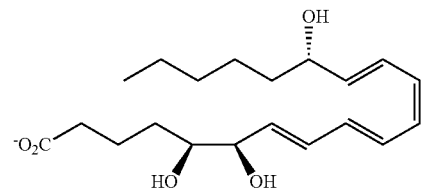
12 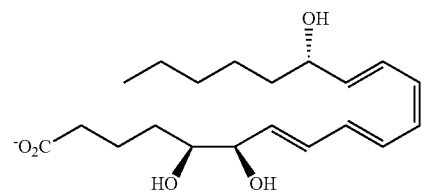
13 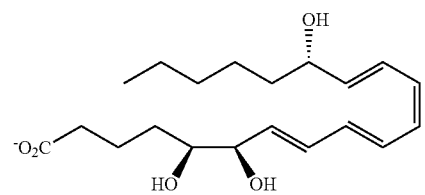

TABLE 5-continued
Structures of Representative Compounds of Formulas I and IV
14 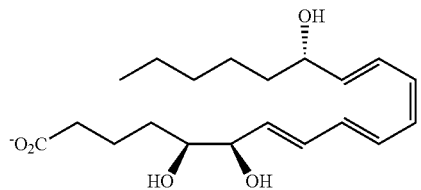
15 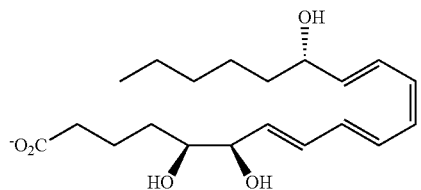
16 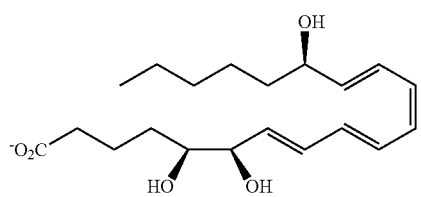
17 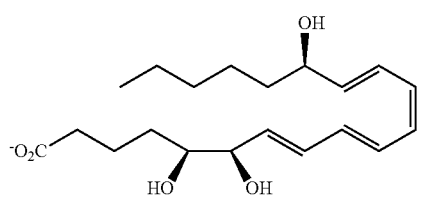
18 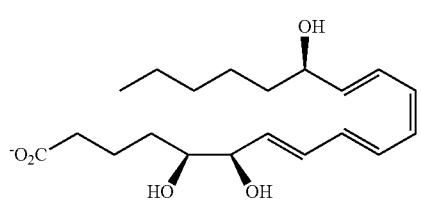
19 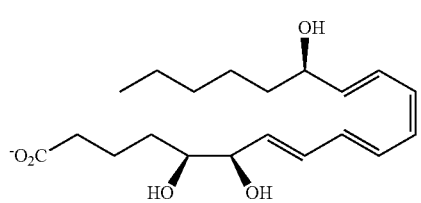
20 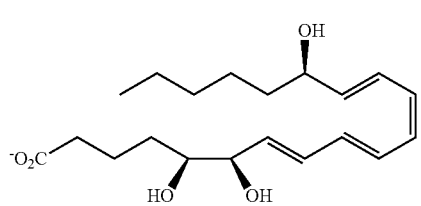
21 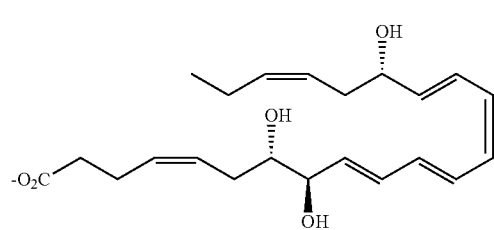

TABLE 5-continued
Structures of Representative Compounds of Formulas I and IV
22 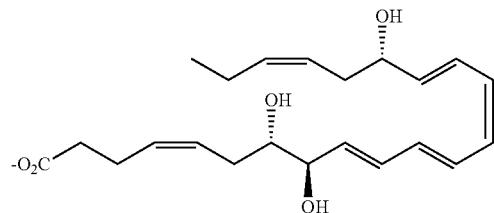
23 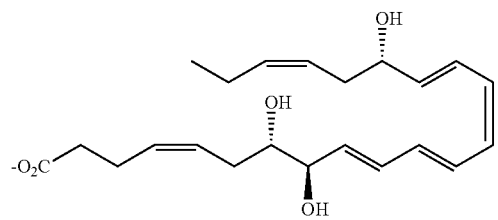
24 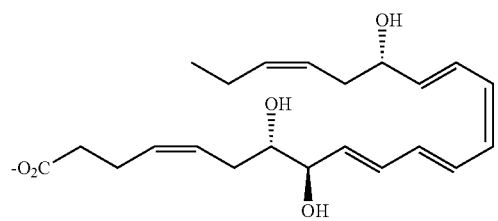
25 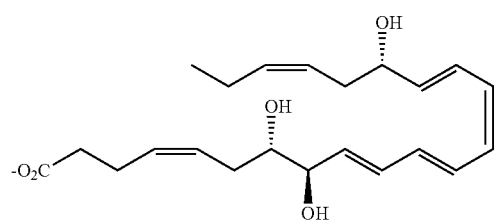
26 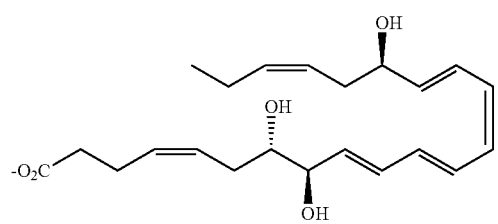
27 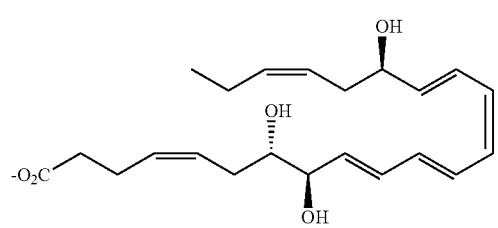
28 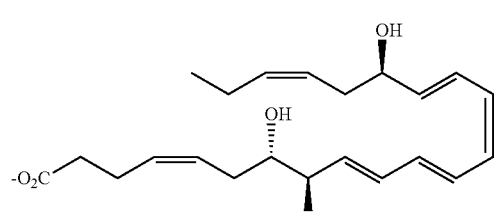

TABLE 5-continued
Structures of Representative Compounds of Formulas I and IV
29 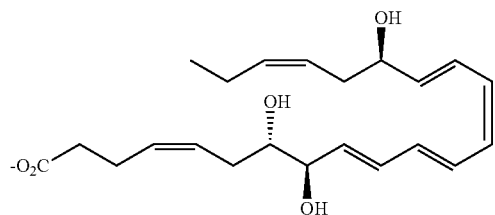
30 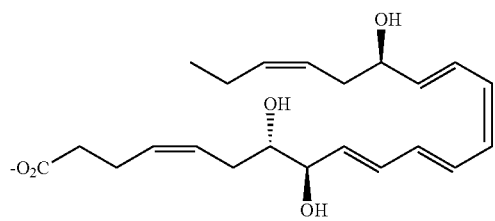
31 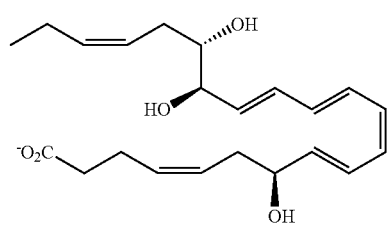
32 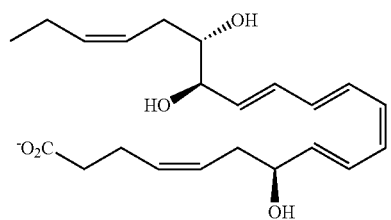
33 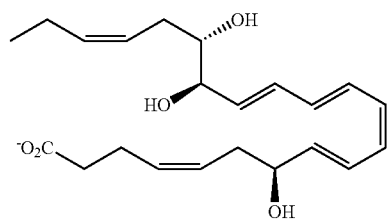
34 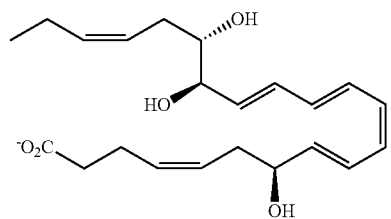
35 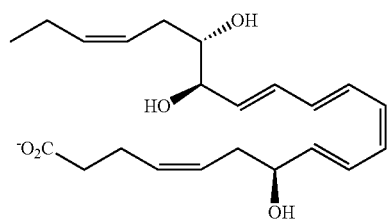

TABLE 5-continued
Structures of Representative Compounds of Formulas I and IV
36 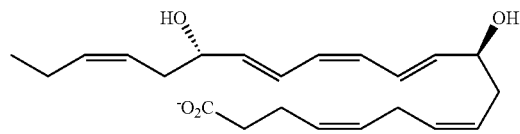
37 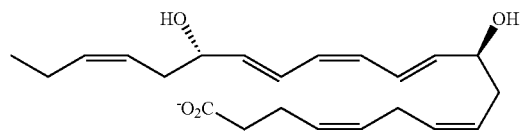
38 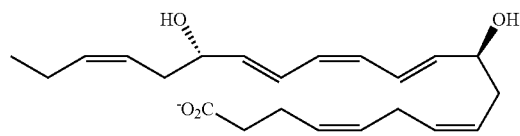
39 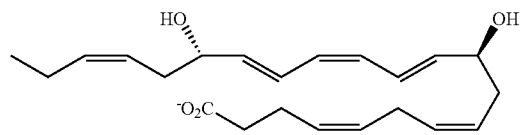
40 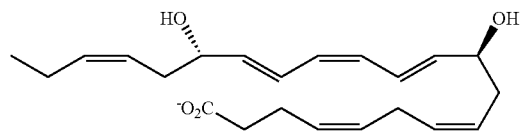
41 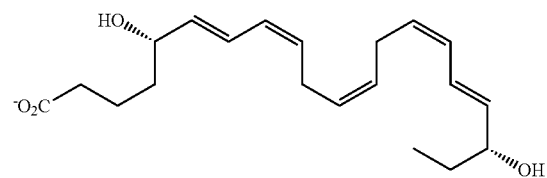
42 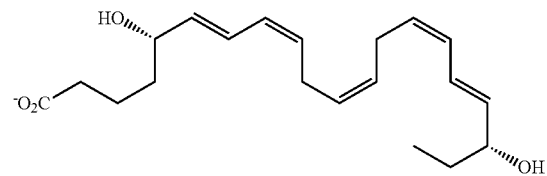
43 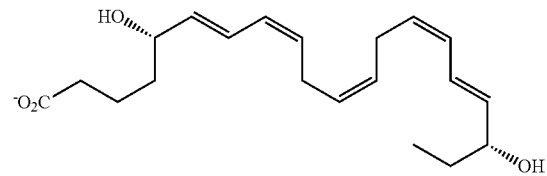
44 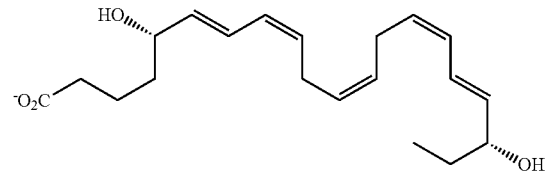

TABLE 5-continued
Structures of Representative Compounds of Formulas I and IV
45 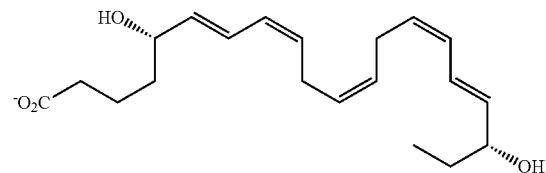
46 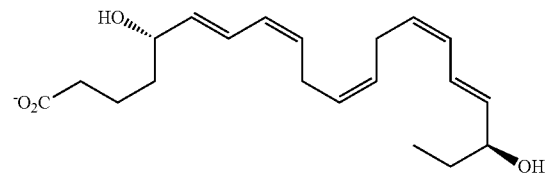
47 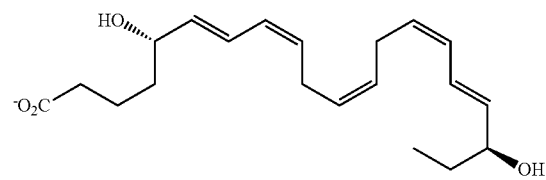
48 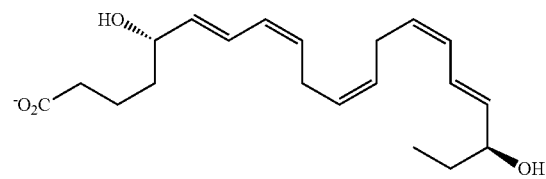
49 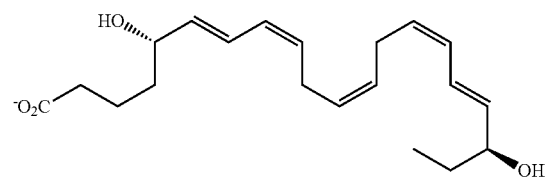
50 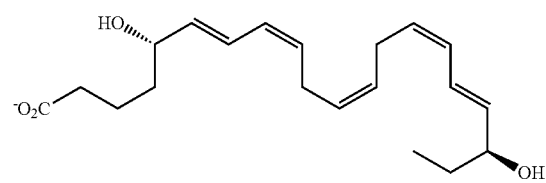
51 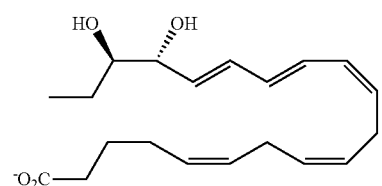
52 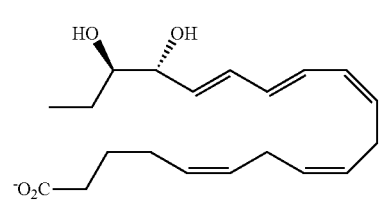

TABLE 5-continued
Structures of Representative Compounds of Formulas I and IV
53 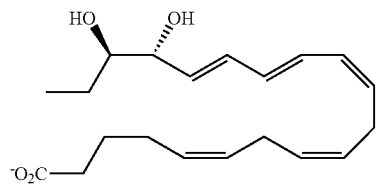
54 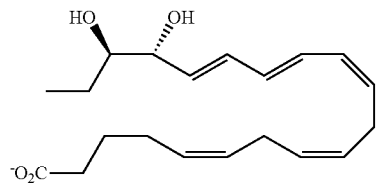
55 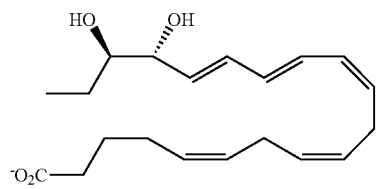
56 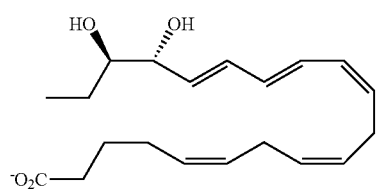
57 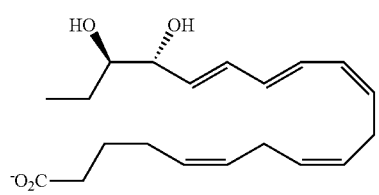
58 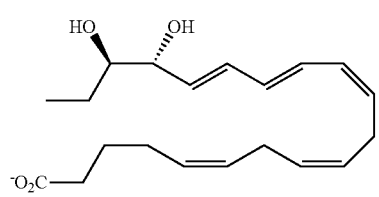
59 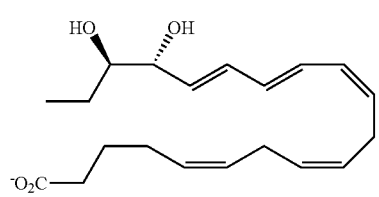
60 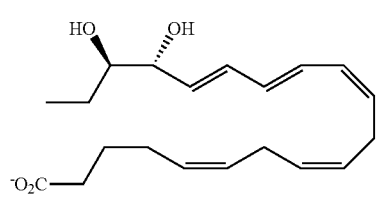

EXAMPLES

Chemical synthesis of the peptide-metal salt component of the compounds described here using other divalent metal cations than those exemplified below can be accomplished by adapting the methods described here using techniques known in the art. For example, as described in U.S. Pat. No. 5,061,815, which is incorporated herein by reference in its entirety. In addition, the skilled person would appreciate that different SPM molecules from those exemplified below may be combined with the metal-dipeptide and dipeptide scaffolds described below in the same manner.

Provided here are exemplary methods of synthesizing representative SPM molecules, for example RvE1, AT-RvD1, RvD2, PDX, and LXA4. These are intended to be non-limiting, as the skilled person may employ an alternate method for obtaining the SPM component of a compound described here. For example, methods of synthesis are described in Li et al., Beilstein *J. Org. Chem.* 2013, 9, 2762-2766 and Vik et al., *Bioorganic and Med. Chem. Let* 2017. In addition, one or more SPMs may be available for purchase from a vendor such as Caymen Chemical Co. (Ann Arbor, Mich.).

Example 1: Synthesis of RvE1

(5S,6Z,8E,10E,12R,14Z,16E,18R)-5,12,18-trihydroxyicosa-6,8,10,14,16-pentaenoic Acid)

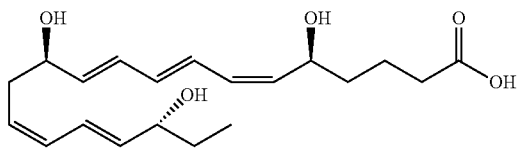 [SMILES: CC[C@@H](O)/C=C/C=C\C[C@@H](O)/C=C/C=C/C=C\[C@@H](O)CCCC(=O)O]

Step 1: Isopropyl (5S,8E,10E,12R,16E,18R)-5,12,18-trihydroxyicosa-8,10,16-trien-6,14-diynoate

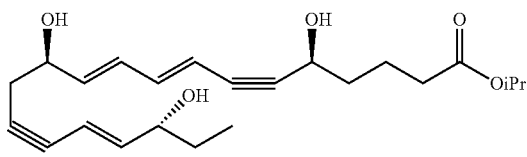 [SMILES: CC[C@@H](O)/C=C/C#CC[C@@H](O)/C=C/C=C/C#C[C@@H](O)CCCC(=O)OC(C)C]

A degassed solution of isopropyl (5S,8E,10E,12R)-5,12-dihydroxypentadeca-8,10-dien-6,14-diynoate (3.972 g, 13.05 mmol) in benzene (50 mL) was added to a degassed solution of (R,E)-1-iodopent-1-en-3-ol (3.62 g, 17.07 mmol), dichlorobis(triphenylphosphine)palladium(II) (0.464 g, 0.661 mmol), tetrakis(triphenylphosphine)palladium(0) (0.482 g, 0.417 mmol), and copper(I) iodide (0.255 g, 1.34 mmol) in benzene (25 mL). The mixture was degassed and purged with nitrogen (2×), piperidine (6.5 mL, 65.8 mmol) was added, the solution was degassed and purged with nitrogen, and the mixture stirred at room temperature under nitrogen atmosphere. After 2 hr, TLC (50% EtOAc/hexane, permanganate stain) showed consumption of the limiting reagent. The reaction was diluted with EtOAc (240 mL) and washed with saturated aqueous ammonium chloride (2×100 mL) and brine (100 mL). The organic solution was dried ($Na_2SO_4$) and concentrated in vacuo. The crude viscous dark amber oil/red solid was purified by flash chromatography (0.75 L silica gel, 40% EtOAc/hexane then 50% once product started to elute) to afford 4.22 g (83%) of isopropyl (5S,8E,10E,12R,16E,18R)-5,12,18-trihydroxyicosa-8,10,16-trien-6,14-diynoate as a viscous amber oil. 1H NMR (400 MHz, Chloroform-d) δ 6.56 (dd, J=15.5, 10.9 Hz, 1H), 6.33 (dd, J=14.9, 11.1 Hz, 1H), 6.08 (dd, J=15.9, 6.1 Hz, 1H), 5.85 (dd, J=15.2, 5.9 Hz, 1H), 5.73-5.59 (m, 2H), 5.00 (hept, J=6.2 Hz, 1H), 4.51 (q, J=4.8, 3.7 Hz, 1H), 4.35 (q, J=6.1 Hz, 1H), 4.13-4.01 (m, 1H), 2.68-2.50 (m, 2H), 2.39-2.28 (m, 2H), 1.86-1.68 (m, 4H), 1.56 (p, J=7.4 Hz, 2H), 1.22 (d, J=6.3 Hz, 6H), 0.92 (t, J=7.4 Hz, 3H).

Step 2: Isopropyl (5S,6Z,8E,10E,12R,14Z,16E,18R)-5,12,18-trihydroxyicosa-6,8,10,14,16-pentaenoate

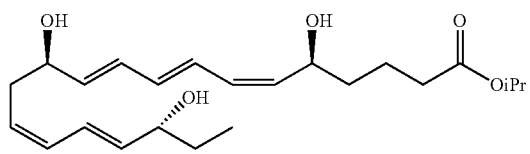 [SMILES: CC[C@@H](O)/C=C/C=C\C[C@@H](O)/C=C/C=C/C=C\[C@@H](O)CCCC(=O)OC(C)C]

Zinc dust (208 g, 3.2 mol) and water (1.2 L) were added to a flask and degassed by passing a stream of nitrogen through the solution for 15 min. Copper(II) acetate monohydrate (20.9 g, 105 mmol) was added and the degassing continued for 15 min. Silver nitrate (21 g, 123 mmol) was added and the mixture stirred for 30 min under continued nitrogen degassing. The mixture was filtered (#2 filter paper, 18.5 cm Buchner funnel) and the remaining solid was washed with water (2×200 mL), methanol (2×200 mL), acetone (2×200 mL) and diethyl ether (2×200 mL). The activated zinc was quickly transferred to a flask containing 1:1 methanol/water (1.2 L) and was treated with a solution of isopropyl (5S,8E,10E,12R,16E,18R)-5,12,18-trihydroxyicosa-8,10,16-trien-6,14-diynoate (2.1 g, 5.4 mmol) in methanol (56 mL) and trimethylsilyl chloride (9.3 mL, 73 mmol), warmed to 40° C., and stirred overnight under nitrogen. The reaction was monitored by GC-MS and showed 99% conversion after 22 hours. The mixture was filtered (250 mL Celite in between two 185 mm #2 filter papers in a Buchner funnel) and the filter cake was rinsed with methanol until no product remained on the cake. The filtrate was concentrated in vacuo (water bath temperature <40° C.) until ~99% of the initial volume was removed. To the remaining solution was added brine (50 mL), a small amount of sodium chloride, and EtOAc (50 mL). The organic layer was collected and the aqueous layer was extracted with EtOAc (2×20 mL). The combined organic solution was dried ($Na_2SO_4$) and concentrated in vacuo (water bath temperature <30° C.). The crude yellow oil was purified by flash chromatography using a Biotage Isolera (120 g silica gel, 10-60% EtOAc/hexane, product elutes in 60% EtOAc/hexane) to afford 1.27 g (60%) of isopropyl (5S,6Z,8E,10E,12R,14Z,16E,18R)-5,12,18-trihydroxyicosa-6,8,10,14,16-pentaenoate as a transparent yellow oil. 1H NMR (400 MHz, Chloroform-d) δ 6.49 (ddd, J=15.8, 11.2, 4.5 Hz, 2H), 6.35-6.04 (m, 4H), 5.78 (dd, J=15.2, 6.9 Hz, 1H), 5.72 (dd, J=15.2, 6.9 Hz, 1H), 5.44 (ddd, J=16.0, 10.5, 8.1 Hz, 2H), 5.00 (hept, J=6.1 Hz, 1H), 4.58 (q, J=6.8, 6.3 Hz, 1H), 4.26 (q, J=6.4 Hz, 1H), 4.15-4.05 (m, 1H), 2.48

(hept, J=7.6 Hz, 2H), 2.30 (t, J=7.0 Hz, 2H), 1.87-1.45 (m, 9H), 1.23 (s, 3H), 1.21 (s, 3H), 0.92 (t, J=7.4 Hz, 3H).

Step 3: (5S,6Z,8E,10E,12R,14Z,16E,18R)-5,12,18-trihydroxyicosa-6,8,10,14,16-pentaenoic Acid (RvE1)

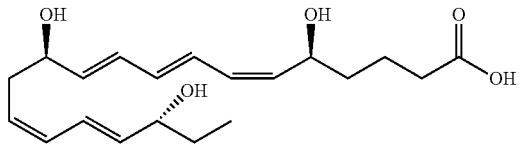 [SMILES: CC[C@@H](O)/C=C/C=C\C[C@@H](O)/C=C/C=C/C=C\[C@@H](O)CCCC(=O)O]

A solution of isopropyl (5S,6Z,8E,10E,12R,14Z,16E,18R)-5,12,18-trihydroxyicosa-6,8,10,14,16-pentaenoate (2.51 g, 6.08 mmol) in THF (37 mL) was treated with 1M LiOH solution (26 mL, 26 mmol). After stirring for 2 hr at room temperature TLC (EtOAc) showed completion. The reaction mixture was diluted with EtOAc (250 mL) and acidified to pH 7-8 with pH 7 0.2M sodium phosphate buffer (28 mL). The layers were separated and sodium chloride was added to the aqueous layer until it was saturated. The aqueous layer was washed with EtOAc until no product remained. The combined organic solution was washed with brine, dried ($Na_2SO_4$), tocopherol (1 drop) was added, and concentrated in vacuo. The crude viscous amber oil was dissolved in 15% MeOH/DCM and purified by flash chromatography (125 mL silica gel, 0-20% MeOH/DCM) to afford 1.38 g (65%) of (5S,6Z,8E,10E,12R,14Z,16E,18R)-5,12,18-trihydroxyicosa-6,8,10,14,16-pentaenoic acid as an amber oil. 1H NMR (400 MHz, Methanol-d4) δ 6.52 (ddd, J=19.6, 14.7, 11.3 Hz, 2H), 6.36-6.18 (m, 2H), 6.07 (t, J=11.0 Hz, 2H), 5.75 (dd, J=14.6, 6.5 Hz, 1H), 5.65 (dd, J=15.2, 6.7 Hz, 1H), 5.44 (dt, J=10.3, 7.5 Hz, 1H), 5.41-5.31 (m, 1H), 4.56 (q, J=7.0 Hz, 1H), 4.16 (q, J=6.5 Hz, 1H), 4.00 (q, J=6.5 Hz, 1H), 2.44 (hept, J=7.3 Hz, 2H), 2.30 (t, J=6.9 Hz, 2H), 1.73-1.40 (m, 6H), 0.90 (t, J=7.4 Hz, 3H).

Example 2: Synthesis of RvE1 (L,L)-Lysyllysine Salt

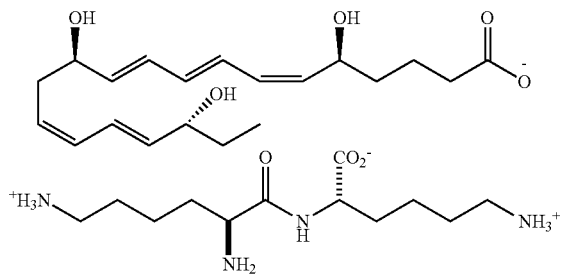

A solution of RvE1 (38.1 mg, 0.109 mmol) in methanol (0.75 mL) and tocopherol (1.7 mg pre-dissolved in 0.2 mL of ethyl acetate) was treated with L-lysyl-L-lysine (30 mg, 0.109 mmol) and the mixture stirred for 20 min at 50° C. The solution cooled slightly, was concentrated in vacuo, and then placed in a vacuum oven at room temperature for 3 hr to afford 63 mg (93%) of RvE1 (L,L)-lysyllysine salt as a very pale orange crisp foam. 1H NMR (400 MHz, Methanol-d4) δ 6.62-6.44 (m, 2H), 6.37-6.16 (m, 2H), 6.07 (q, J=10.7 Hz, 2H), 5.74 (dd, J=14.8, 6.6 Hz, 1H), 5.65 (dd, J=15.2, 6.7 Hz, 1H), 5.45 (dt, J=10.8, 7.7 Hz, 1H), 5.42-5.30 (m, 1H), 4.57 (q, J=7.1 Hz, 1H), 4.26 (dd, J=7.9, 5.2 Hz, 1H), 4.16 (q, J=6.5 Hz, 1H), 4.01 (q, J=6.6 Hz, 1H), 2.90 (t, J=7.2 Hz, 4H), 2.43 (tt, J=14.5, 7.8 Hz, 2H), 2.18 (t, J=6.8 Hz, 2H), 1.87 (td, J=13.4, 7.9 Hz, 2H), 1.75-1.40 (m, 16H), 0.91 (t, J=7.4 Hz, 3H).

Example 3: Synthesis of Bis RvE1 Mg di-(L)-lysinate Salt

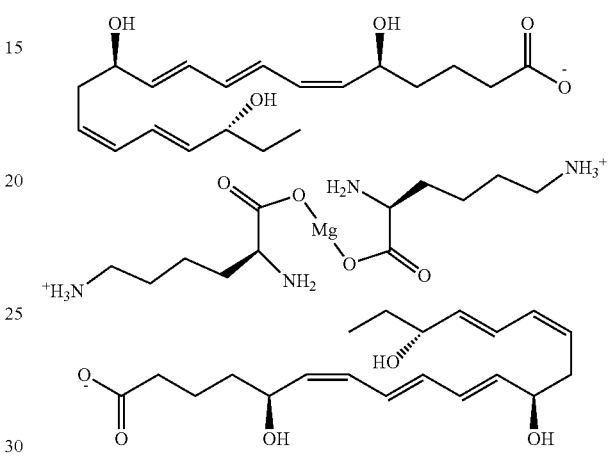

A solution of RvE1 (60.3 mg, 0.172 mmol) in methanol (1 mL) and tocopherol (2.1 mg pre-dissolved in 0.2 mL of ethyl acetate) was treated with magnesium lysinate (27.1 mg, 0.086 mmol) and the mixture stirred for 20 min at 50° C. The solution cooled slightly, was concentrated in vacuo, and then placed in a vacuum oven at room temperature for 3 hr to afford 85 mg (97%) of bis(RvE1) magnesium L-lysinate salt as a very pale orange crisp foam. 1H NMR (400 MHz, Acetic Acid-d4) δ 6.61-6.46 (m, 4H), 6.33 (dd, J=14.8, 10.6 Hz, 2H), 6.24 (dd, J=14.6, 10.5 Hz, 2H), 6.10 (td, J=11.1, 4.1 Hz, 4H), 5.79 (dd, J=14.9, 6.7 Hz, 2H), 5.69 (dd, J=15.2, 6.8 Hz, 2H), 5.45 (dt, J=14.6, 8.9 Hz, 4H), 4.71 (q, J=7.5, 6.9 Hz, 2H), 4.30 (q, J=6.5 Hz, 2H), 4.15 (q, J=6.6 Hz, 2H), 4.04 (t, J=6.2 Hz, 2H), 3.07 (t, J=7.4 Hz, 4H), 2.50 (ddq, J=28.8, 14.7, 7.0 Hz, 4H), 2.39 (t, J=7.1 Hz, 4H), 2.02-1.90 (m, 4H), 1.81-1.46 (m, 20H), 0.89 (t, J=7.4 Hz, 6H).

Example 4: Synthesis of Bis RvE1 Ca di-(L)-lysinate Salt

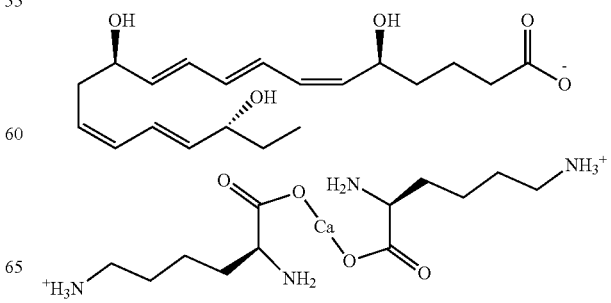

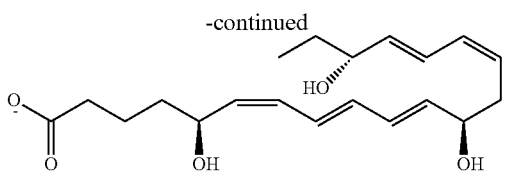

A solution of RvE1 (74.2 mg, 0.212 mmol) in methanol (0.7 mL) and tocopherol (2.6 mg pre-dissolved in 0.2 mL of ethyl acetate) was treated with a solution of calcium lysinate (35 mg, 0.106 mmol) in MeOH (0.6 mL) and the mixture stirred for 20 min at 50° C. The solution cooled slightly, was concentrated in vacuo, and then placed in a vacuum oven at room temperature for 3 hr to afford 104 mg (96%) of bis(RvE1) calcium L-lysinate salt as a pale orange solid. 1H NMR (400 MHz, Deuterium Oxide) δ 6.64 (td, J=11.5, 2.9 Hz, 2H), 6.54 (dd, J=15.3, 11.1 Hz, 2H), 6.42-6.29 (m, 4H), 6.20 (t, J=11.0 Hz, 4H), 5.89-5.79 (m, 2H), 5.76 (dd, J=15.3, 7.0 Hz, 2H), 5.57-5.46 (m, 2H), 5.44 (t, J=10.0 Hz, 2H), 4.67 (q, J=6.8 Hz, 2H), 4.32 (q, J=6.5 Hz, 2H), 4.13 (q, J=6.7 Hz, 2H), 3.59 (t, J=6.1 Hz, 2H), 3.06-2.95 (m, 4H), 2.51 (t, J=7.2 Hz, 4H), 2.20 (t, J=7.0 Hz, 4H), 1.81 (dtd, J=9.1, 6.4, 2.7 Hz, 4H), 1.75-1.37 (m, 24H), 0.88 (t, J=7.4 Hz, 6H).

Example 5: Synthesis of AT-RvD1

(4Z,7S,8R,9E,11E,13Z,15E,17R,19Z)-7,8,17-trihydroxydocosa-4,9,11,13,15,19-hexaenoic Acid (17-epi-RvD1)

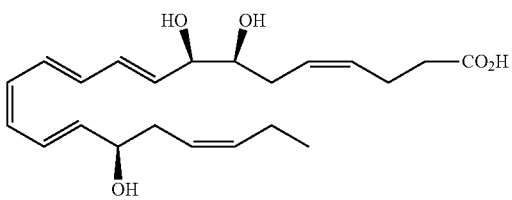 [SMILES: CC/C=C\C[C@@H](O)/C=C/C=C\C=C\C=C\[C@@H](O)[C@@H](O)C/C=C\CCC(=O)O]

Step 1: Methyl (Z)-6-((4S,5R)-5-((R,1E,3E,7E,11Z)-9-hydroxytetradeca-1,3,7,11-tetraen-5-yn-1-yl)-2,2-dimethyl-1,3-dioxolan-4-yl)hex-4-enoate

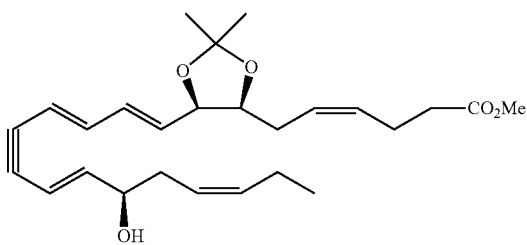 [SMILES: CC/C=C\C[C@@H](O)/C=C/C#C/C=C/C=C/[C@H]1OC(C)(C)O[C@H]1C/C=C\CCC(=O)OC]

A mixture of (R,1E,5Z)-1-iodoocta-1,5-dien-3-ol (1.18 g, 4.03 mmol) and methyl (Z)-6-((4S,5R)-5-((1E,3E)-hexa-1,3-dien-5-yn-1-yl)-2,2-dimethyl-1,3-dioxolan-4-yl)hex-4-enoate (1.13 g, 3.71 mmol) was azeotropically dried with anhydrous acetonitrile (25 mL). The mixture was dissolved in anhydrous acetonitrile (43 mL), degassed and purged with nitrogen (2×), treated with bis(triphenylphosphine)palladium(II)chloride (388.3 mg, 0.553 mmol) and copper iodide (516.9 mg, 2.71 mol), degassed, cooled to 0° C., treated with triethylamine (2.7 mL, 19.4 mmol), stirred for 2 hr at 0° C., warmed to room temperature, and stirred overnight. After 18.5 hr, TLC (30% EtOAc/hexane) showed the limiting reagent was consumed, and pH 7 0.2M sodium phosphate buffer (20 mL) and EtOAc (80 mL) were added to the flask. The layers were separated and the combined organic solution was washed with water (until Cu was gone), brine (50 mL), dried (Na₂SO₄), and concentrated in vacuo. The crude oil was purified by flash chromatography (140 mL silica gel, 20-30% EtOAc/hexane) to afford 0.46 g (29%) of methyl (Z)-6-((4S,5R)-5-((R,1E,3E,7E,11Z)-9-hydroxytetradeca-1,3,7,11-tetraen-5-yn-1-yl)-2,2-dimethyl-1,3-dioxolan-4-yl)hex-4-enoate. 1H NMR (400 M Hz, Chloroform-d) δ 6.59 (dd, J=15.4, 11.0 Hz, 1H), 6.42 (dd, J=14.6, 14.1 Hz, 1H), 6.33 (m, 1H), 6.16 (dd, J=15.9, 5.6 Hz, 1H), 5.88 (m, 1H), 5.75 (m, 1H), 5.67-5.54 (m, 1H), 5.44 (p, J=6.5, 5.9 Hz, 2H), 5.41-5.28 (m, 1H), 4.59 (t, J=7.0 Hz, 1H), 4.34-4.14 (m, 2H), 3.67 (s, 3H), 2.40-2.30 (m, 6H), 2.30-2.21 (m, 1H), 2.21-2.12 (m, 1H), 2.12-2.01 (m, 2H), 1.70 (d, J=4.0 Hz, 1H), 1.49 (s, 3H), 1.36 (s, 3H), 0.97 (t, J=7.6 Hz, 3H).

Step 2: Methyl (4Z,7S,8R,9E,11E,15E,17R,19Z)-7,8,17-trihydroxydocosa-4,9,11,15,19-pentaen-13-ynoate

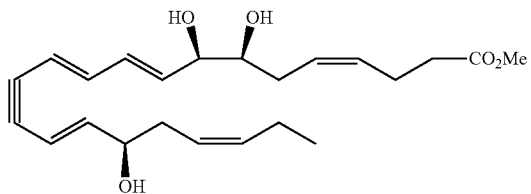 [SMILES: CC/C=C\C[C@@H](O)/C=C/C#C/C=C/C=C/[C@@H](O)[C@@H](O)C/C=C\CCC(=O)OC]

A solution of methyl (Z)-6-((4S,5R)-5-((R,1E,3E,7E,11Z)-9-hydroxytetradeca-1,3,7,11-tetraen-5-yn-1-yl)-2,2-dimethyl-1,3-dioxolan-4-yl)hex-4-enoate (0.38 g, 0.883 mmol) in methanol (31 mL) was treated with 1M HCl (8 mL, 8 mmol) and stirred at room temperature. After 4 hr TLC (50% EtOAc/hexane, permanganate stain) showed completion. The reaction was quenched with saturated aqueous sodium bicarbonate (40 mL) and then extracted with EtOAc (100 mL). The combined organic solution was washed with water (60 mL), brine (30 mL), dried (Na₂SO₄), and concentrated in vacuo. The crude product was purified by flash chromatography using the Biotage Isolera (25 g silica, 45-90% EtOAc/hexane) to afford 0.34 g (99%) of methyl (4Z,7S,8R,9E,11E, 15E,17R,19Z)-7,8,17-trihydroxydocosa-4,9,11,15,19-pentaen-13-ynoate as a yellow oil. 1H NMR (400 MHz, Chloroform-d) δ 6.60 (dd, J=15.4, 10.9 Hz, 1H), 6.38 (dd, J=15.4, 10.8 Hz, 1H), 6.16 (dd, J=15.8, 5.6 Hz, 1H), 5.93-5.82 (m, 2H), 5.75 (dd, J=15.4, 2.0 Hz, 1H), 5.66-5.54 (m, 1H), 5.48 (td, J=4.8, 2.3 Hz, 2H), 5.40-5.28 (m, 1H), 4.23 (m, 2H), 3.72 (dq, J=8.2, 4.0 Hz, 1H), 3.67 (s, 3H), 2.53 (d, J=4.0 Hz, 1H), 2.48-2.15 (m, 9H), 2.05 (d, J=10.0 Hz, 2H), 1.71 (d, J=4.3 Hz, 1H), 0.97 (t, J=7.5 Hz, 3H).

Step 3: Methyl (4Z,7S,8R,9E,11E,13Z,15E,17R,19Z)-7,8,17-trihydroxydocosa-4,9,11,13,15,19-hexaenoate

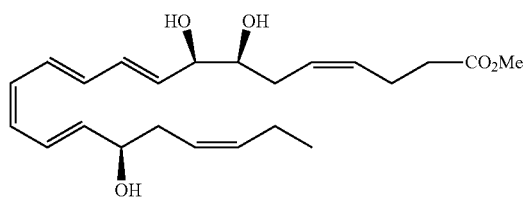 [SMILES: CC/C=C\C[C@@H](O)/C=C/C=C\C=C\C=C\[C@@H](O)[C@@H](O)C/C=C\CCC(=O)OC]

Zinc dust (22.3 g, 341 mmol) and water (250 mL) were added to a flask and degassed by passing a stream of nitrogen through the solution for 15 min. Copper(II) acetate monohydrate (2.24 g, 11.2 mmol) was added and the degassing continued for 15 min. Silver nitrate (2.24 g, 13.2 mmol) was added and the mixture stirred for 30 min under continued nitrogen degassing. The mixture was filtered through a medium fritted Buchner funnel and the remaining solid was washed with water (2×50 mL), methanol (2×50 mL), acetone (2×50 mL) and diethyl ether (2×50 mL). The zinc mixture was quickly transferred to a flask containing 1:1 methanol/water (220 mL) and was treated with a solution of methyl (4Z,7S,8R,9E,11E,15E, 17R,19Z)-7,8,17-trihydroxydocosa-4,9,11,15,19-pentaen-13-ynoate (350 mg, 0.901 mmol) in methanol (325 mL), trimethylsilyl chloride (1.56 mL, 12.2 mmol), and stirred overnight. The reaction was monitored by GCMS and showed 100% conversion after 22 hours. The mixture was filtered through a pad of Celite (100 mL, filter cake was rinsed with methanol until all product had passed through the Celite), and the filtrate was concentrated in vacuo (water bath temperature <30° C.) until ~80% of the initial volume was removed. To the remaining solution was added brine (50 mL) and EtOAc (80 mL). The organic layer was collected and the aqueous layer was extracted with EtOAc (30 mL). The combined organic solution was washed with brine (20 mL), dried ($Na_2SO_4$), and concentrated in vacuo (water bath temperature <30° C.). The crude product was purified by flash chromatography (40 mL silica gel, 50% EtOAc/hexane) to afford 288 mg (82%) of methyl (4Z,7S,8R,9E,11E,13Z,15E,17R,19Z)-7,8,17-trihydroxydocosa-4,9,11,13,15,19-hexaenoate as a glassy, pale yellow solid. Note: One drop of (+)-α-tocopherol was added to the purified product before the solvent was removed. 1H NMR (400 MHz, Chloroform-d) δ 6.79-6.65 (m, 2H), 6.40 (dd, J=15.1, 10.8 Hz, 1H), 6.27 (dd, J=14.6, 10.8 Hz, 1H), 6.08-5.96 (m, 2H), 5.80 (ddd, J=15.1, 12.6, 6.5 Hz, 2H), 5.64-5.54 (m, 1H), 5.49 (t, J=5.0 Hz, 2H), 5.41-5.31 (m, 1H), 4.30-4.19 (m, 2H), 3.71 (dt, J=7.9, 4.0 Hz, 1H), 3.66 (s, 3H), 2.51-2.15 (m, 10H), 2.14-2.01 (m, 2H), 1.75 (s, 1H), 0.97 (t, J=7.5 Hz, 3H).

Step 4: (4Z,7S,8R,9E,11E,13Z,15E,17R,19Z)-7,8,17-trihydroxydocosa-4,9,11,13,15,19-hexaenoic Acid (17-epi-RvD1)

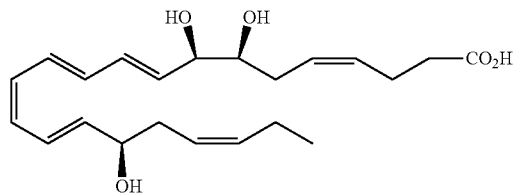 [SMILES: CC/C=C\C[C@@H](O)/C=C/C=C\C=C\C=C\[C@@H](O)[C@@H](O)C/C=C\CCC(=O)O]

A cooled (3° C.) solution of methyl (4Z,7S,8R,9E,11E,13Z,15E,17R,19Z)-7,8,17-trihydroxydocosa-4,9,11,13,15,19-hexaenoate (246 mg, 0.630 mmol) in THF (13 mL) was treated with 1M aqueous LiOH solution (3.8 mL, 3.8 mmol). After stirring for 22 hr at 3° C. TLC (EtOAc, CAM stain) showed completion. The reaction mixture was diluted with EtOAc (60 mL) and acidified to pH 7-8 with pH 7 0.2M sodium phosphate buffer (~17 mL). The layers were separated and the aqueous layer was washed with EtOAc until product was no longer in aqueous layer (6×10 mL). The combined organic solution was washed with water (25 mL), brine (15 mL), dried ($Na_2SO_4$), tocopherol (4.2 mg) was added, and concentrated in vacuo to afford 207 mg (87%) of (4Z,7S,8R,9E,11E,13Z,15E,17R,19Z)-7,8,17-trihydroxydocosa-4,9,11,13,15,19-hexaenoic acid (17-epi-RvD1) as a translucent yellow oil. 1H NMR (400 MHz, Chloroform-d) δ 6.69 (m, 1H), 6.42-6.27 (m, 1H), 6.29-6.16 (m, 1H), 6.04-5.92 (m, 2H), 5.77 (m, 2H), 5.59-5.40 (m, 3H), 5.38-5.27 (m, 1H), 4.28-4.07 (m, 2H), 3.74-3.61 (m, 1H), 2.47-2.12 (m, 8H), 2.05 (m, 2H), 1.44-1.36 (m, 1H), 1.34-1.15 (m, 2H), 1.01-0.88 (m, 3H), 0.88-0.76 (m, 1H).

Example 6: Synthesis of AT-RvD1 (L,L)-Lysyllysine Salt

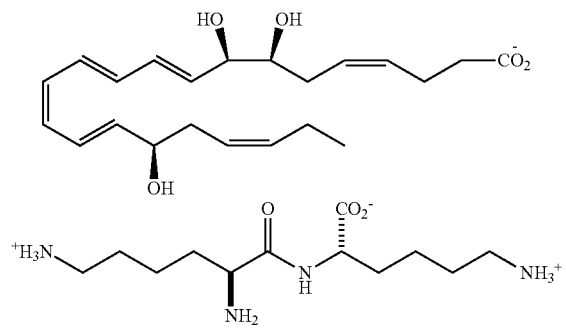

A solution of 17-epi-RvD1 (27.4 mg, 72.8 μmol) in methanol (0.5 mL) and tocopherol (0.9 mg pre-dissolved in 0.2 mL of ethyl acetate) was treated with L-lysyl-L-lysine (19.9 mg, 72.5 μmol) and the mixture stirred for 20 min at 50 degrees C. The solution cooled slightly, was concentrated in vacuo, and then placed in a vacuum oven at room temperature for 3 hr to afford 47 mg (100%) of 17-epi-RvD1 (L,L)-Lysyllysine salt as a pale orange crisp foam. 1H NMR (400 MHz, Methanol-d4) δ 6.80-6.68 (m, 2H), 6.40 (dd, J=14.8, 11.0 Hz, 1H), 6.29 (dd, J=14.5, 10.8 Hz, 1H), 6.00 (p, J=10.8 Hz, 2H), 5.87 (dd, J=15.0, 6.8 Hz, 1H), 5.73 (dd, J=15.1, 6.5 Hz, 1H), 5.57-5.42 (m, 3H), 5.43-5.32 (m, 1H), 4.26 (dd, J=7.8, 5.3 Hz, 1H), 4.17 (q, J=6.8 Hz, 1H), 4.02 (t, J=6.1 Hz, 1H), 3.58-3.49 (m, 1H), 3.43-3.35 (m, 1H), 2.91 (t, J=7.4 Hz, 4H), 2.40-2.15 (m, 8H), 2.06 (p, J=8.1, 7.7 Hz, 2H), 1.86 (dt, J=13.2, 6.5 Hz, 2H), 1.75-1.58 (m, 6H), 1.45 (dq, J=16.5, 9.0, 8.0 Hz, 4H), 0.96 (t, J=7.5 Hz, 3H).

Example 7: Synthesis of Bis AT-RvD1 Mg di-(L)-lysinate Salt

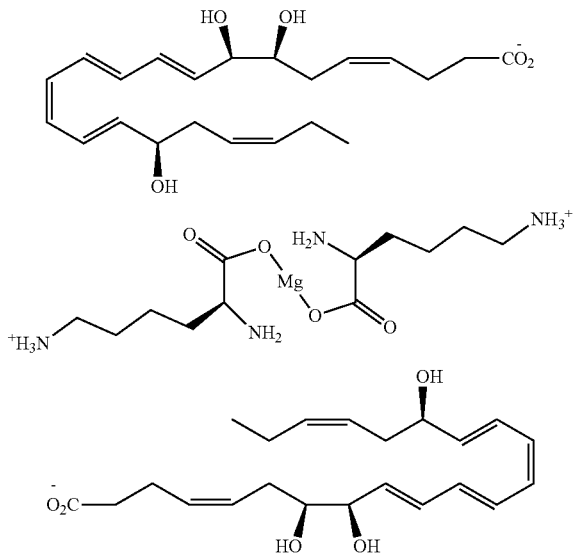

A solution of 17-epi-RvD1 (35.9 mg, 95.4 μmol) in methanol (0.5 mL) and tocopherol (1.3 mg pre-dissolved in 0.2 mL of ethyl acetate) was treated with magnesium L-lysinate (15 mg, 47.7 μmol) and the mixture stirred for 20 min at 50° C. The solution cooled slightly, was concentrated in vacuo, and then placed in a vacuum oven at room temperature for 3 hr to afford 51 mg (100%) of bis(17-epi-RvD1) magnesium L-lysinate salt as a glassy orange solid. 1H NMR (400 MHz, Acetic Acid-d4) δ 6.81-6.69 (m, 4H), 6.41 (dd, J=15.2, 10.8 Hz, 2H), 6.28 (dd, J=14.6, 10.7 Hz, 2H), 6.09-5.94 (m, 4H), 5.86 (dd, J=15.1, 7.2 Hz, 2H), 5.77 (dd, J=15.1, 6.6 Hz, 2H), 5.49 (m, 6H), 5.36 (dt, J=11.7, 7.5 Hz, 2H), 4.35-4.23 (m, 4H), 4.08-4.00 (m, 2H), 3.86-3.77 (m, 2H), 3.13-3.02 (m, 4H), 2.45-2.25 (m, 16H), 2.09-1.91 (m, 8H), 1.75 (dt, J=14.4, 7.4 Hz, 4H), 1.58 (m, 4H), 0.94 (t, J=7.5 Hz, 6H).

Example 8: Synthesis of RvD2

(4Z,7S,8E,10Z,12E,14E,16R,17S,19Z)-7,16,17-trihydroxydocosa-4,8,10,12,14,19-hexaenoic Acid)

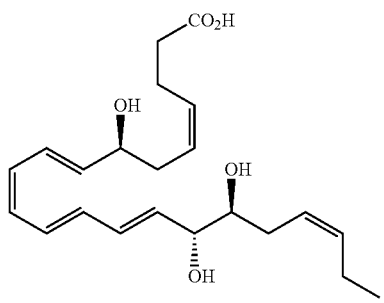 [SMILES: CC/C=C\C[C@H](O)[C@H](O)/C=C/C=C/C=C\C=C\[C@@H](O)C/C=C\CCC(=O)O]

Step 1: (S,4Z,8E,12E,14E)-methyl 15-((4R,5S,)-2,2-dimethyl-5-((Z)-pent-2-en-1-yl)-1,3-dioxolan-4-yl)-7-hydroxypentadeca-4,8,12,14-tetraen-10-ynotae

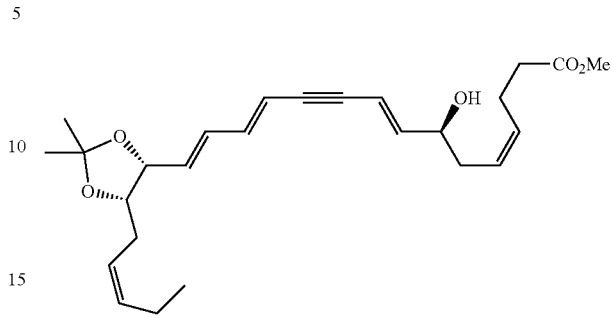

A mixture of (4R,5S)-4-((1E,3E)-4-iodobuta-1,3-dien-1-yl)-2,2-dimethyl-5-((Z)-pent-2-en-1-yl)-1,3-dioxolane (1.68 g, 4.83 mmol) and methyl-(S,4Z,8E)-7-hydroxyundeca-4,8-dien-10-ynoate (0.919 g, 4.41 mmol) was azeotropically dried with anhydrous acetonitrile (3×5 mL). The mixture was dissolved in anhydrous acetonitrile (50 mL), degassed under vacuum and purged with nitrogen (2×), treated with bis(triphenylphosphine)palladium(II)chloride (0.318 g, 0.453 mmol) and copper iodide (0.315 g, 1.65 mmol), degassed, cooled to 0° C., treated with triethylamine (3.05 mL, 21.9 mmol), stirred for 2 hr at 0° C., and warmed to room temperature overnight. After 18 hr, TLC (20% EtOAc/hexane) showed the reaction was complete and pH 7 0.2M sodium phosphate buffer (75 mL) was added to the flask. The layers were separated and the aqueous layer washed with EtOAc (150 mL). The combined organic solution was washed with water (2×75 mL), brine (50 mL), dried (Na2SO4), and concentrated in vacuo. The crude oil was purified by flash chromatography (30% EtOAc/hexane) to afford 1.48 g (79%) of (S,4Z,8E,12E,14E)-methyl 15-((4R, 5S,)-2,2-dimethyl-5-((Z)-pent-2-en-1-yl)-1,3-dioxolan-4-yl)-7-hydroxypentadeca-4,8,12,14-tetraen-10-ynotae as a brown oil. 1H NMR (400 MHz, Chloroform-d) δ 6.59 (dd, J=15.4, 10.9 Hz, 1H), 6.32 (dd, J=15.0, 10.9 Hz, 1H), 6.17 (dd, J=15.8, 5.5 Hz, 1H), 5.90 (d, J=15.8 Hz, 1H), 5.81-5.70 (m, 2H), 5.48 (m, 3H), 5.31 (m, 1H), 4.63-4.54 (m, 1H), 4.26 (m, 1H), 4.23-4.13 (m, 1H), 3.67 (s, 3H), 2.43-2.33 (m, 6H), 2.27 (dt, J=14.1, 7.2 Hz, 1H), 2.20-2.09 (m, 1H), 2.03 (m, 2H), 1.50 (s, 3H), 1.37 (s, 3H), 0.96 (t, J=7.5 Hz, 3H).

Step 2: (4Z,7S,8E,12E,14E,16R,17S,19Z)-methyl 7,16,17-trihydroxydocosa-4,8,12,14,19-pentaen-10-ynoate

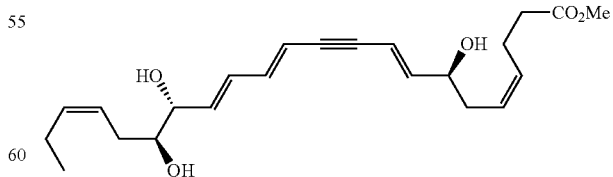

A solution of (S,4Z,8E,12E,14E)-methyl 15-((4R,5S,)-2,2-dimethyl-5-((Z)-pent-2-en-1-yl)-1,3-dioxolan-4-yl)-7-hydroxypentadeca-4,8,12,14-tetraen-10-ynotae (1.48 g, 3.45 mmol) in methanol (75 mL) was treated with 1M HCl (19 mL, 18.9 mmol). After stirring for 2 hr TLC (50% EtOAc/ hexane, permanganate stain) showed the reaction was complete. The reaction was quenched with sat. aq. NaHCO₃ (60 mL) and extracted with EtOAc (2×150 mL). The organic solution was washed with water (100 mL), dried (Na₂SO₄), treated with one drop of (+)-α-tocopherol, and concentrated in vacuo. The crude product was purified by flash chromatography (50% EtOAc/hexane) to afford 1.03 g (77%) of (4Z,7S,8E,12E,14E,16R,17S,19Z)-methyl 7,16,17-trihydroxydocosa-4,8,12,14,19-pentaen-10-ynoate. 1H NMR (400 MHz, Chloroform-d) δ 6.60 (dd, J=15.4, 10.9 Hz, 1H), 6.37 (dd, J=15.2, 11.0 Hz, 1H), 6.17 (dd, J=15.8, 5.5 Hz, 1H), 5.95-5.81 (m, 2H), 5.75 (d, J=14.1 Hz, 1H), 5.64-5.48 (m, 2H), 5.51-5.40 (m, 1H), 5.37 (m, 1H), 4.31-4.20 (m, 2H), 3.73 (dt, J=8.6, 4.3 Hz, 1H), 3.67 (s, 3H), 2.44-2.34 (m, 6H), 2.29 (dt, J=16.1, 8.2 Hz, 1H), 2.21-2.12 (m, 1H), 2.10-1.98 (m, 2H), 0.97 (t, J=7.5 Hz, 3H).

Step 3: (4Z,7S,8E,10Z,12E,14E,16R,17S,19Z)-methyl 7,16,17-trihydroxydocosa-4,8,10,12,14,19-hexaenoate

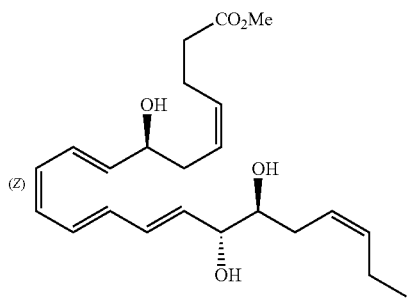 [SMILES: CC/C=C\C[C@H](O)[C@H](O)/C=C/C=C/C=C\C=C\[C@@H](O)C/C=C\CCC(=O)OC]

Zinc dust (63.68 g, 973.6 mmol) and water (750 mL) were added to a flask and degassed by passing a stream of nitrogen through the solution for 15 min. Copper(II) acetate monohydrate (6.35 g, 31.81 mmol) was added and the degassing continued for another 15 min. Silver nitrate (6.35 g, 37.38 mmol) was added and the mixture stirred for 30 min under continued nitrogen degassing. The mixture was filtered through a medium fritted Buchner funnel and the remaining solid was washed with water (2×160 mL), methanol (2×160 mL), acetone (2×160 mL) and ether (2×160 mL). The activated zinc was quickly transferred to a flask containing 1:1 methanol/water (320 mL) and was treated with a solution of (4Z,7S,8E,12E,14E,16R,17S,19Z)-methyl 7,16,17-trihydroxydocosa-4,8,12,14,19-pentaen-10-ynoate (1.03 g, 2.65 mmol) in methanol (1 L), trimethylsilyl chloride (4.4 mL, 34.4 mmol), and stirred overnight. The reaction was monitored by GCMS and showed 100% conversion after 22 hours. The mixture was filtered through a pad of Celite (filter cake was rinsed with methanol), and the filtrate was concentrated in vacuo (water bath temperature was kept below 27° C.) until ~70% of the initial volume was removed. To the remaining solution was added water and EtOAc until two layers formed. The organic layer was collected and the aqueous layer was extracted with EtOAc (2×100 mL). The combined organic solution was dried (Na₂SO₄), treated with one drop of (+)-α-tocopherol, and concentrated in vacuo (water bath temperature was kept below 27° C.) to afford 1.27 g (82%) of crude product as a light yellow oil. 1H NMR (600 MHz, Chloroform-d) δ 6.78-6.67 (m, 1H), 6.37 (m, 1H), 6.32-6.22 (m, 1H), 6.03 (m, 1H), 5.84-5.73 (m, 1H), 5.60-5.42 (m, 3H), 5.40-5.32 (m, 1H), 4.25 (d, J=26.6 Hz, 2H), 3.73 (dq, J=9.1, 4.6 Hz, 1H), 3.67 (s, 3H), 2.45-2.32 (m, 6H), 2.32-2.23 (m, 1H), 2.22-2.13 (m, 1H), 2.05 (m, 2H), 0.96 (t, J=7.6 Hz, 3H).

Step 4: (4Z,7S,8E,10Z,12E,14E,16R,17S,19Z)-7,16,17-trihydroxydocosa-4,8,10,12,14,19-hexaenoic Acid (RvD2)

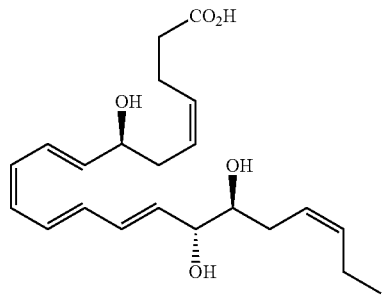 [SMILES: CC/C=C\C[C@H](O)[C@H](O)/C=C/C=C/C=C\C=C\[C@@H](O)C/C=C\CCC(=O)O]

A cooled (0° C.) solution of (4Z,7S,8E,10Z,12E,14E,16R,17S,19Z)-methyl 7,16,17-trihydroxydocosa-4,8,10,12,14,19-hexaenoate (1.03 g, 2.64 mmol) in THF (54 mL) under nitrogen was treated with 1M LiOH solution (16.5 mL, 16.5 mmol) and stirred for 1 d at 4° C. The reaction mixture was diluted with EtOAc (150 mL) and acidified (pH 7-8) with pH 7 0.2M sodium phosphate buffer (175 mL). The layers were separated and the aqueous solution was extracted well with EtOAc (6×75 mL). The combined organic solution was washed with water, brine, dried (Na₂SO₄), and concentrated in vacuo to afford 0.94 g (75%) of (4Z,7S,8E,10Z,12E,14E,16R,17S,19Z)-7,16,17-trihydroxydocosa-4,8,10,12,14,19-hexaenoic acid (RvD2) as an opaque, yellow oil. 1H NMR (600 MHz, Chloroform-d) δ 6.76-6.67 (m, 2H), 6.40 (dd, J=15.2, 10.8 Hz, 1H), 6.26 (dd, J=14.7, 10.8 Hz, 1H), 6.06-5.97 (m, 2H), 5.79 (m, 2H), 5.59-5.44 (m, 3H), 5.40-5.33 (m, 1H), 4.28 (q, J=5.9 Hz, 1H), 4.24 (dd, J=6.9, 3.6 Hz, 1H), 3.73 (dt, J=8.2, 4.2 Hz, 1H), 2.50-2.32 (m, 6H), 2.31-2.23 (m, 1H), 2.18 (dt, J=14.8, 5.8 Hz, 1H), 2.05 (m, J=7.1 Hz, 2H), 0.96 (t, J=7.5 Hz, 3H).

Example 9: Synthesis of RvD2 (L,L)-Lysyllysine Salt

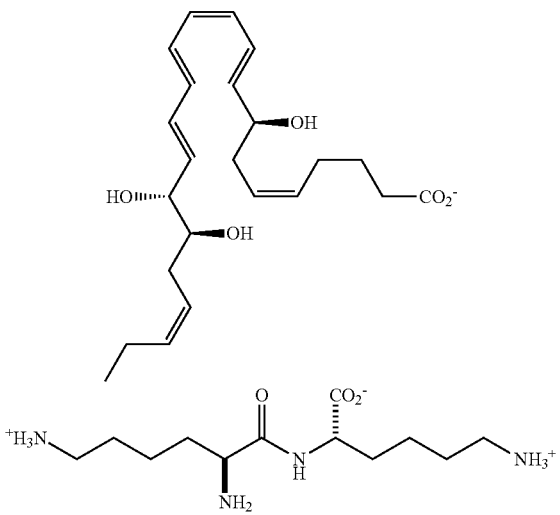

A 50° C. solution of L,L-lysyllysine (58.9 mg, 0.215 mmol) in methanol (0.5 mL) was treated with a solution of tocopherol (2.8 mg in 0.2 mL of EtOAc) and a solution of RvD2 (84.5 mg, 0.224 mmol) in methanol (0.5 mL). The solution stirred for 20 minutes, cooled slightly, and was concentrated in vacuo. The oil was re-suspended in HPLC grade acetonitrile (~3 mL), cooled to 0° C., and stirred for 3 hours to triturate the solid. Only a small amount of filterable solid formed and the suspension was stored at −20° C. overnight. The material was filtered and dried overnight in a vacuum oven (ambient temperature) to afford 46 mg (33%) of RvD2 L,L-lysyllysine salt as a light orange solid. 1H NMR (400 MHz, Methanol-d4) δ 6.81-6.70 (m, 2H), 6.39 (dd, J=14.7, 10.9 Hz, 1H), 6.29 (dd, J=14.4, 10.9 Hz, 1H), 6.08-5.95 (m, 2H), 5.85 (dd, J=15.0, 7.1 Hz, 1H), 5.76 (dd, J=15.1, 6.3 Hz, 1H), 5.58-5.36 (m, 4H), 4.27 (dd, J=7.8, 5.3 Hz, 1H), 4.18 (q, J=6.3 Hz, 1H), 4.05-3.97 (m, 1H), 3.54 (dt, J=8.2, 4.8 Hz, 1H), 3.41 (t, J=6.6 Hz, 1H), 2.92 (t, J=7.4 Hz, 4H), 2.34 (m, 5H), 2.26-2.14 (m, 3H), 2.10-2.05 (m, 2H), 1.87 (m, 2H), 1.68 (m, 6H), 1.47 (m, 4H), 0.97 (t, J=7.5 Hz, 3H).

Example 10: Synthesis of Bis RvD2 Mg di-(L)-lysinate Salt

A 50° C. solution of magnesium L-lysinate (40 mg, 0.127 mmol) in methanol (0.5 mL) was treated with a solution of tocopherol (3.1 mg in 0.2 mL of EtOAc) and a solution of RvD2 (104.6 mg, 0.278 mmol) in methanol (0.5 mL). The mixture stirred for 20 minutes, cooled slightly, and was concentrated in vacuo. The foam was re-suspended in HPLC grade acetonitrile (~3 mL), stirred for 1.5 hours to triturate the solid, filtered, and dried overnight in a vacuum oven (ambient temperature) to afford 107 mg (79%) of bis(RvD2) magnesium L-lysinate salt as a light orange solid. 1H NMR (400 MHz, Acetic Acid-d4) δ 6.83-6.69 (m, 4H), 6.41 (dd, J=15.1, 10.8 Hz, 2H), 6.29 (dd, J=14.5, 10.8 Hz, 2H), 6.10-5.96 (m, 4H), 5.87 (dd, J=15.1, 7.3 Hz, 2H), 5.79 (dd, J=15.1, 6.6 Hz, 2H), 5.54-5.34 (m, 8H), 4.33 (q, J=6.3 Hz, 2H), 4.27 (dd, J=7.1, 3.6 Hz, 2H), 4.05 (t, J=6.1 Hz, 2H), 3.82 (m, 2H), 3.08 (t, J=7.3 Hz, 4H), 2.39-2.27 (m, 16H), 2.10-1.93 (m, 8H), 1.76 (m, 4H), 1.60 (m, 4H), 0.94 (t, J=7.5 Hz, 6H).

Example 11: Synthesis of PDX (L,L)-Lysyllysine Salt

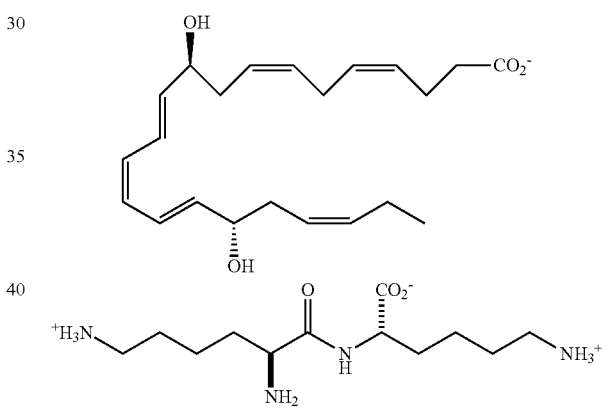

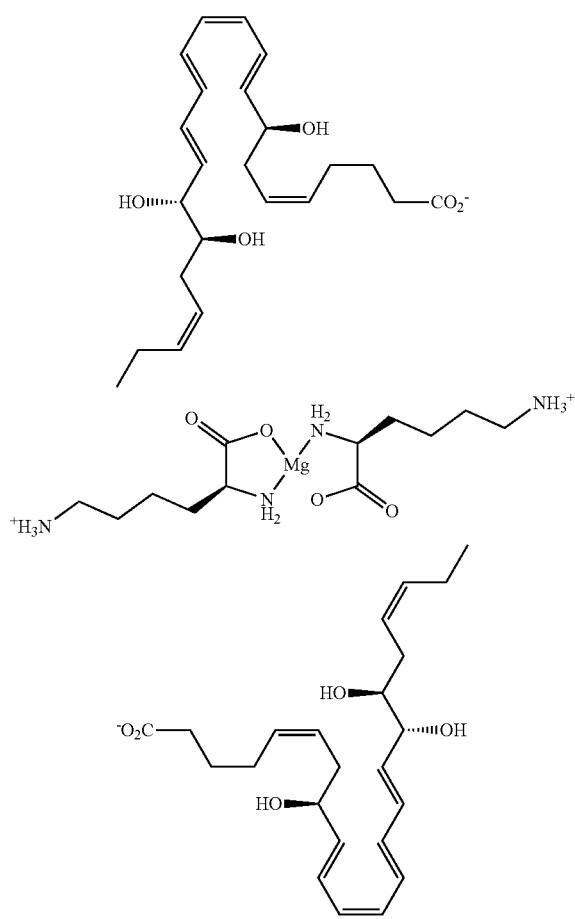

A 50° C. solution of L,L-lysyllysine (55.7 mg, 0.203 mmol) in methanol (0.5 mL) was treated with a solution of tocopherol (1.8 mg in 0.2 mL of EtOAc) and a solution of PDX (80.0 mg, 0.222 mmol) in methanol (0.5 mL). The solution stirred for 20 minutes, cooled slightly, and was concentrated in vacuo. The foam was re-suspended in HPLC grade acetonitrile (~3 mL), stirred for 3 hours to triturate the solid, filtered, and dried overnight in the vacuum oven (ambient temperature) to afford 52 mg (39%) of PDX L,L-lysyllysine salt as a very sticky, orange solid. 1H NMR (400 MHz, Methanol-d4) δ 6.70 (dd, J=14.6, 9.3 Hz, 2H), 6.01-5.89 (m, 2H), 5.71 (ddd, J=14.8, 8.0, 6.4 Hz, 2H), 5.51-5.25 (m, 6H), 4.24 (dd, J=7.7, 5.3 Hz, 1H), 4.14 (m, 2H), 3.38 (t, J=6.5 Hz, 1H), 2.89 (t, J=7.3 Hz, 4H), 2.82 (t, J=6.4 Hz, 2H), 2.40-2.21 (m, 6H), 2.21-2.13 (m, 2H), 2.04 (m, 2H), 1.91-1.78 (m, 2H), 1.66 (m, 6H), 1.45 (m, 4H), 0.94 (t, J=7.5 Hz, 3H).

Example 12: Synthesis of Bis PDX Mg di-(L)-lysinate Salt

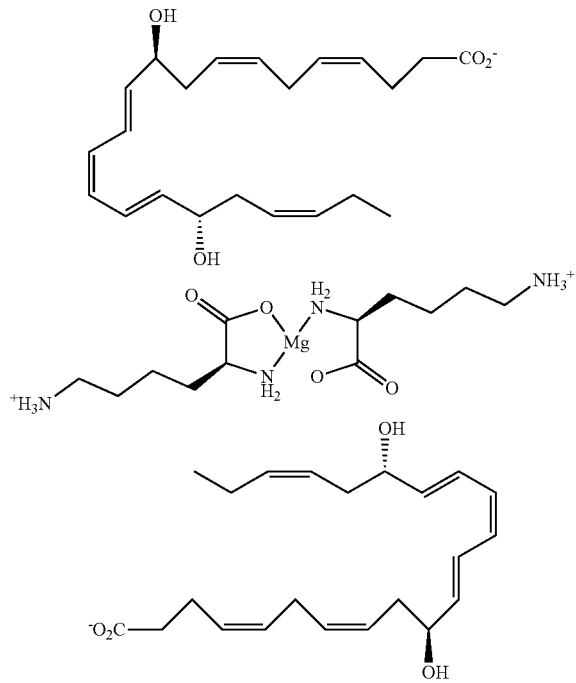

A 50° C. solution of magnesium L-lysinate (40.1 mg, 0.127 mmol) in methanol (0.5 mL) was treated with a solution of tocopherol (2.2 mg in 0.2 mL of EtOAc) and a solution of PDX (103.0 mg, 0.286 mmol) in methanol (0.5 mL). The solution stirred for 20 minutes, cooled slightly and was concentrated in vacuo. The oil was re-suspended in HPLC grade acetonitrile (~3 mL), stirred for 1.5 hr to triturate the solid, filtered, and dried overnight in a vacuum oven (ambient temperature) to afford 68 mg (50%) of bis(PDX) magnesium L-lysinate salt as a slightly tacky orange solid. 1H NMR (400 MHz, Acetic Acid-d4) δ 6.74 (dd, J=15.2, 7.8 Hz, 4H), 6.04-5.92 (m, 4H), 5.76 (ddd, J=15.0, 6.4, 3.6 Hz, 4H), 5.53-5.29 (m, 12H), 4.30 (dq, J=13.0, 6.4 Hz, 4H), 4.04 (t, J=5.3 Hz, 2H), 3.07 (t, J=7.3 Hz, 4H), 2.83 (t, J=5.4 Hz, 4H), 2.53-2.24 (m, 16H), 2.10-1.92 (m, 8H), 1.75 (m, 4H), 1.59 (dt, J=15.1, 6.4 Hz, 4H), 0.93 (t, J=7.5 Hz, 6H).

Example 13: Synthesis of LXA4

(5S,6R,7E,9E,11Z,13E,15S)-5,6,15-trihydroxyicosa-7,9,11,13-tetraenoic Acid)

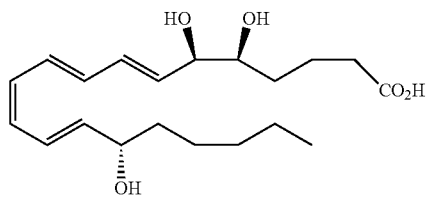 [SMILES: CCCCC[C@H](O)/C=C/C=C\C=C\C=C\[C@@H](O)[C@@H](O)CCCC(=O)O]

Step 1: Ethyl 4-((4S,5R)-5-((S,1E,3E,7E)-9-hydroxytetradeca-1,3,7-trien-5-yn-1-yl)-2,2-dimethyl-1,3-dioxolan-4-yl)butanoate

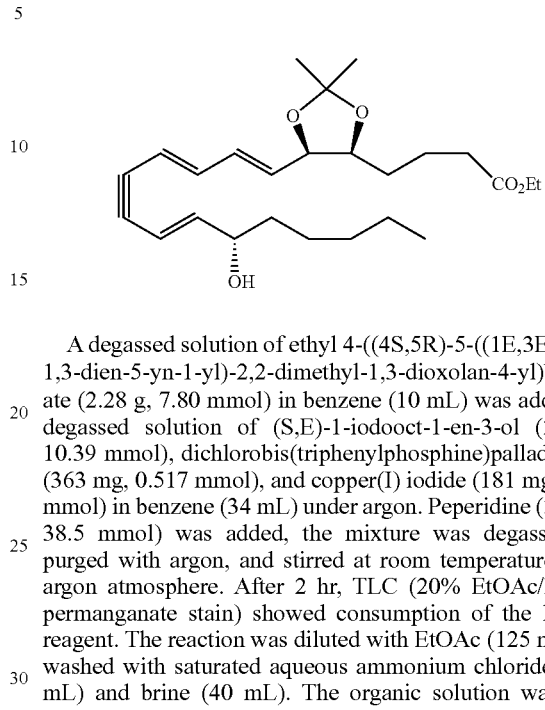

A degassed solution of ethyl 4-((4S,5R)-5-((1E,3E)-hexa-1,3-dien-5-yn-1-yl)-2,2-dimethyl-1,3-dioxolan-4-yl)butanoate (2.28 g, 7.80 mmol) in benzene (10 mL) was added to a degassed solution of (S,E)-1-iodooct-1-en-3-ol (2.64 g, 10.39 mmol), dichlorobis(triphenylphosphine)palladium(II) (363 mg, 0.517 mmol), and copper(I) iodide (181 mg, 0.950 mmol) in benzene (34 mL) under argon. Peperidine (3.8 mL, 38.5 mmol) was added, the mixture was degassed and purged with argon, and stirred at room temperature under argon atmosphere. After 2 hr, TLC (20% EtOAc/hexane, permanganate stain) showed consumption of the limiting reagent. The reaction was diluted with EtOAc (125 mL) and washed with saturated aqueous ammonium chloride (2×40 mL) and brine (40 mL). The organic solution was dried (Na₂SO₄) and concentrated in vacuo. The crude oil was dissolved in 50% EtOAc/hexane and purified by flash chromatography (700 mL silica gel, 40-50% EtOAc/hexane) to afford 2.84 g (86%) of ethyl 4-((4S,5R)-5-((S,1E,3E,7E)-9-hydroxytetradeca-1,3,7-trien-5-yn-1-yl)-2,2-dimethyl-1,3-dioxolan-4-yl)butanoate as a light amber oil. 1H NMR (400 MHz, Chloroform-d) δ 6.58 (dd, J=15.5, 10.9 Hz, 1H), 6.29 (dd, J=15.2, 10.9 Hz, 1H), 6.14 (dd, J=15.9, 6.2 Hz, 1H), 5.84 (dt, J=15.9, 1.8 Hz, 1H), 5.78-5.65 (m, 2H), 4.55 (t, J=7.0 Hz, 1H), 4.22-4.06 (m, 4H), 2.32 (td, J=7.4, 2.4 Hz, 2H), 1.79 (ddtd, J=12.6, 10.1, 7.4, 5.4 Hz, 1H), 1.72-1.48 (m, 5H), 1.48 (s, 3H), 1.47-1.36 (m, 2H), 1.35 (s, 3H), 1.30 (q, J=3.7, 2.8 Hz, 4H), 1.25 (t, J=7.1 Hz, 3H), 0.94-0.79 (m, 3H).

Step 2: Ethyl (5S,6R,7E,9E,13E,15S)-5,6,15-trihydroxyicosa-7,9,13-trien-11-ynoate

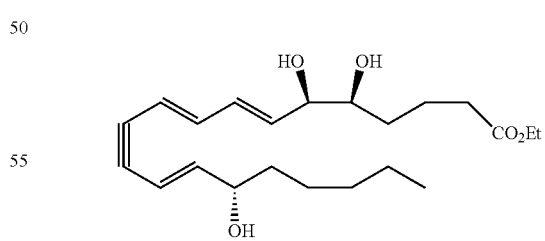

A solution of ethyl 4-((4S,5R)-5-((S,1E,3E,7E)-9-hydroxytetradeca-1,3,7-trien-5-yn-1-yl)-2,2-dimethyl-1,3-dioxolan-4-yl)butanoate (2.84 g, 6.79 mmol) in EtOH (110 mL) was treated with 1M HCl (34 mL, 34 mmol) and stirred at room temperature. After 16 hr, TLC (EtOAc, permanganate stain) showed completion. The reaction was quenched with saturated aqueous sodium bicarbonate (50 mL) and extracted with EtOAc (3×40 mL). The combined organic solution was washed with water (100 mL), brine (150 mL), dried (Na₂SO₄), and concentrated in vacuo. The amber oil was purified by flash chromatography (400 mL silica gel, 50% then 80% EtOAc/hexane) to afford 1.57 g (61%) of ethyl (5S,6R,7E,9E,13E,15S)-5,6,15-trihydroxyicosa-7,9,13-trien-11-ynoate as a yellow oil. 1H NMR (400 MHz, Chloroform-d) δ 6.58 (dd, J=15.4, 10.9 Hz, 1H), 6.35 (dd, J=15.3, 10.9 Hz, 1H), 6.15 (dd, J=15.8, 6.1 Hz, 1H), 5.83 (dd, J=15.3, 6.9 Hz, 2H), 5.75 (dd, J=15.4, 2.2 Hz, 1H), 4.14 (dtd, J=17.6, 6.9, 3.3 Hz, 4H), 3.70 (dq, J=8.3, 3.7 Hz, 1H), 2.34 (td, J=7.3, 2.2 Hz, 2H), 1.83 (ddq, J=13.2, 9.2, 7.0, 6.5 Hz, 1H), 1.75-1.61 (m, 1H), 1.59-1.28 (m, 10H), 1.25 (td, J=7.1, 2.3 Hz, 3H), 0.89 (t, J=6.7 Hz, 3H).

Step 3: Ethyl (5S,6R,7E,9E,11Z,13E,15S)-5,6,15-trihydroxyicosa-7,9,11,13-tetraenoate

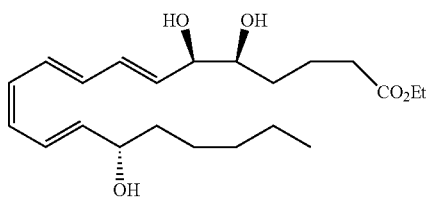 [SMILES: CCCCC[C@H](O)/C=C/C=C\C=C\C=C\[C@@H](O)[C@@H](O)CCCC(=O)OCC]

Zinc dust (104.6 g, 1.6 mol) and water (1.2 L) were added to a flask and degassed by passing a stream of nitrogen through the solution for 15 min. Copper(II) acetate monohydrate (10.4 g, 52 mmol) was added and the degassing continued for 15 min. Silver nitrate (10.3 g, 61 mmol) was added and the mixture stirred for 30 min under continued nitrogen degassing. The mixture was filtered (#2 filter paper, Buchner funnel) and the remaining solid was washed with water (2×100 mL), methanol (2×100 mL), acetone (2×100 mL) and diethyl ether (2×100 mL). The zinc was quickly transferred to a flask containing 1:1 methanol/water (840 mL) and was treated with a solution of ethyl (5S,6R,7E,9E,13E,15S)-5,6,15-trihydroxyicosa-7,9,13-trien-11-ynoate (1.57 g, 4.15 mmol) in methanol (400 mL) and trimethylsilyl chloride (7 mL, 55 mmol). The suspension stirred overnight at room temperature under nitrogen. The reaction was monitored by GC-MS and showed >99% conversion after 23 hours. The mixture was filtered (100 mL Celite between two 185 mm #2 filter papers in a Buchner funnel) and the filter cake was rinsed with methanol until no product remained on the cake. The filtrate was concentrated in vacuo (water bath temperature <35° C.) until ~99% of the initial volume was removed. The remaining solution was diluted with EtOAc (50 mL) and brine (30 mL) and a small amount of sodium chloride was added. The organic layer was collected and the aqueous layer was extracted with EtOAc (2×20 mL). The combined organic solution was dried (Na₂SO₄) and concentrated in vacuo (water bath temperature <30° C.). The crude yellow wax was dissolved in 1:1 DCM/hexane and purified by flash chromatography (300 mL silica gel, 50% EtOAc/hexane then 75% once the product started eluting) to afford 1.26 g (80%) of ethyl (5S,6R,7E,9E,11Z,13E,15S)-5,6,15-trihydroxyicosa-7,9,11,13-tetraenoate as a sticky, translucent, yellow wax. 1H NMR (400 MHz, Chloroform-d) δ 6.76-6.63 (m, 1H), 6.44-6.19 (m, 4H), 6.10-5.96 (m, 1H), 5.77 (ddd, J=15.6, 9.1, 6.9 Hz, 2H), 4.24-4.17 (m, 1H), 4.12 (qd, J=7.2, 2.7 Hz, 3H), 3.70 (s, 1H), 2.40-2.31 (m, 2H), 1.89-1.77 (m, 2H), 1.75-1.64 (m, 2H), 1.53-1.19 (m, 14H), 0.94-0.82 (m, 3H).

Step 4: (5S,6R,7E,9E,11Z,13E,15S)-5,6,15-trihydroxyicosa-7,9,11,13-tetraenoic Acid (LxA4)

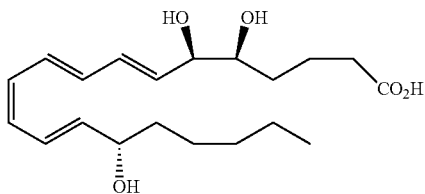 [SMILES: CCCCC[C@H](O)/C=C/C=C\C=C\C=C\[C@@H](O)[C@@H](O)CCCC(=O)O]

A cooled (4° C.) solution of ethyl (5S,6R,7E,9E,11Z,13E,15S)-5,6,15-trihydroxyicosa-7,9,11,13-tetraenoate (1.26 g, 3.31 mmol) in THF (70 mL) was treated with 1M LiOH solution (20 mL, 20 mmol). After stirring for 15 hr at 4° C., TLC (EtOAc, permanganate stain) showed completion. The reaction mixture was diluted with EtOAc (250 mL) and acidified to pH 7-8 with pH 7 0.2M sodium phosphate buffer (~30 mL). The layers were separated and the aqueous layer was washed with EtOAc until product was no longer in the aqueous layer. The combined organic solution was washed with water (30 mL), brine (30 mL), dried (Na₂SO₄), tocopherol (5 mg) was added, and concentrated in vacuo to afford 0.77 g (66%) of (5S,6R,7E,9E,11Z,13E,15S)-5,6,15-trihydroxyicosa-7,9,11,13-tetraenoic acid as an opaque, light yellow powder. 1H NMR (400 MHz, Methanol-d4) δ 6.82-6.64 (m, 2H), 6.38 (dd, J=14.7, 10.6 Hz, 1H), 6.27 (dd, J=14.5, 10.8 Hz, 1H), 6.07-5.93 (m, 2H), 5.83 (dd, J=15.0, 6.9 Hz, 1H), 5.71 (dd, J=15.0, 6.6 Hz, 1H), 4.12 (q, J=5.9 Hz, 1H), 3.98 (ddd, J=6.6, 5.1, 1.1 Hz, 1H), 3.50 (ddd, J=9.3, 5.0, 3.0 Hz, 1H), 2.31 (t, J=7.3 Hz, 2H), 1.90-1.76 (m, 1H), 1.70-1.26 (m, 11H), 0.97-0.84 (m, 3H).

Example 14: Synthesis of Bis LXA4 Mg di-(L)-lysinate Salt

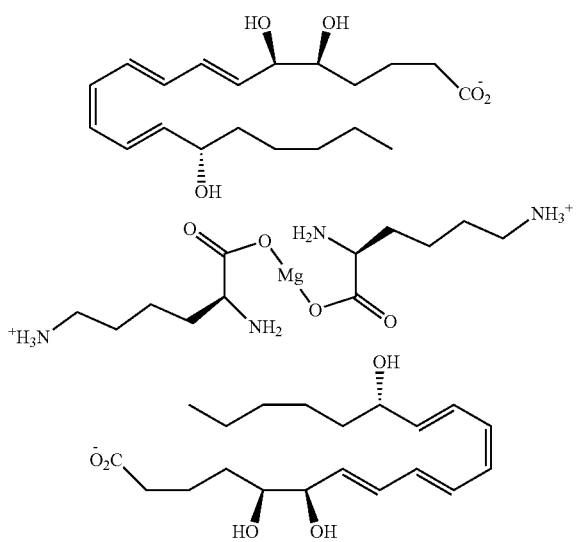

A solution of LxA4 (84.4.3 mg, 0.240 mmol) in methanol (1.6 mL) and tocopherol (3.3 mg pre-dissolved in 0.2 mL of ethyl acetate) was treated with magnesium L-lysinate (37.7 mg, 0.120 mmol) and the mixture stirred for 20 min at 50° C. The solution cooled slightly, was concentrated in vacuo, and then placed in a vacuum oven at room temperature overnight to afford 122 mg (100%) of bis(LxA4) magnesium L-lysinate salt as a very pale orange solid. 1H NMR (400 MHz, Methanol-d4) δ 6.80-6.64 (m, 4H), 6.37 (ddd, J=15.1, 10.8, 1.1 Hz, 2H), 6.27 (dd, J=14.5, 10.8 Hz, 2H), 6.06-5.92 (m, 4H), 5.83 (dd, J=15.0, 6.9 Hz, 2H), 5.70 (dd, J=15.0, 6.7 Hz, 2H), 4.12 (q, J=5.9 Hz, 2H), 3.99 (ddd, J=6.5, 5.0, 1.1 Hz, 2H), 3.57-3.47 (m, 4H), 2.91 (dd, J=8.2, 6.8 Hz, 4H), 2.19 (ddd, J=9.0, 7.0, 2.3 Hz, 4H), 1.91-1.41 (m, 24H), 1.37-1.26 (m, 12H), 0.94-0.86 (m, 6H).

Example 15: Compounds of Formulas I and IV Show Increased Stability Against Degradation The stability of selected SPMs and their ionic derivatives based on Formulas I and IV was evaluated. The parent SPM and its solid ionic derivative were place in open test tubes and maintained at room temperature between 68-72 F and relative humidity between 20-40% for 6 or 8 weeks. Qualitative demonstration of stability was determined using standard high pressure liquid chromatography (HPLC) analytic methods. Briefly, HPLC analysis was performed on a PFP column (Poroshell 120, PFP, 4.6×150 mm, 2.7 m, Agilent), mounted on a Gilson HPLC system equipped with an ELS detector. The mobile phase consisted of a gradient between solution A, water, and solution B, acetonitrile, both containing 0.1% trifluoroacetic acid. The gradient program was 30-80% with respect to solution B. The flow rate was 0.5 mL/min. The appearance of new HPLC peaks as compared to the baseline HPLC tracing at the initial time point is indicative of decomposition products and the lack of stability. The absence of such new HPLC peaks the subsequent time points is indicative of stability.

Figure 1B:
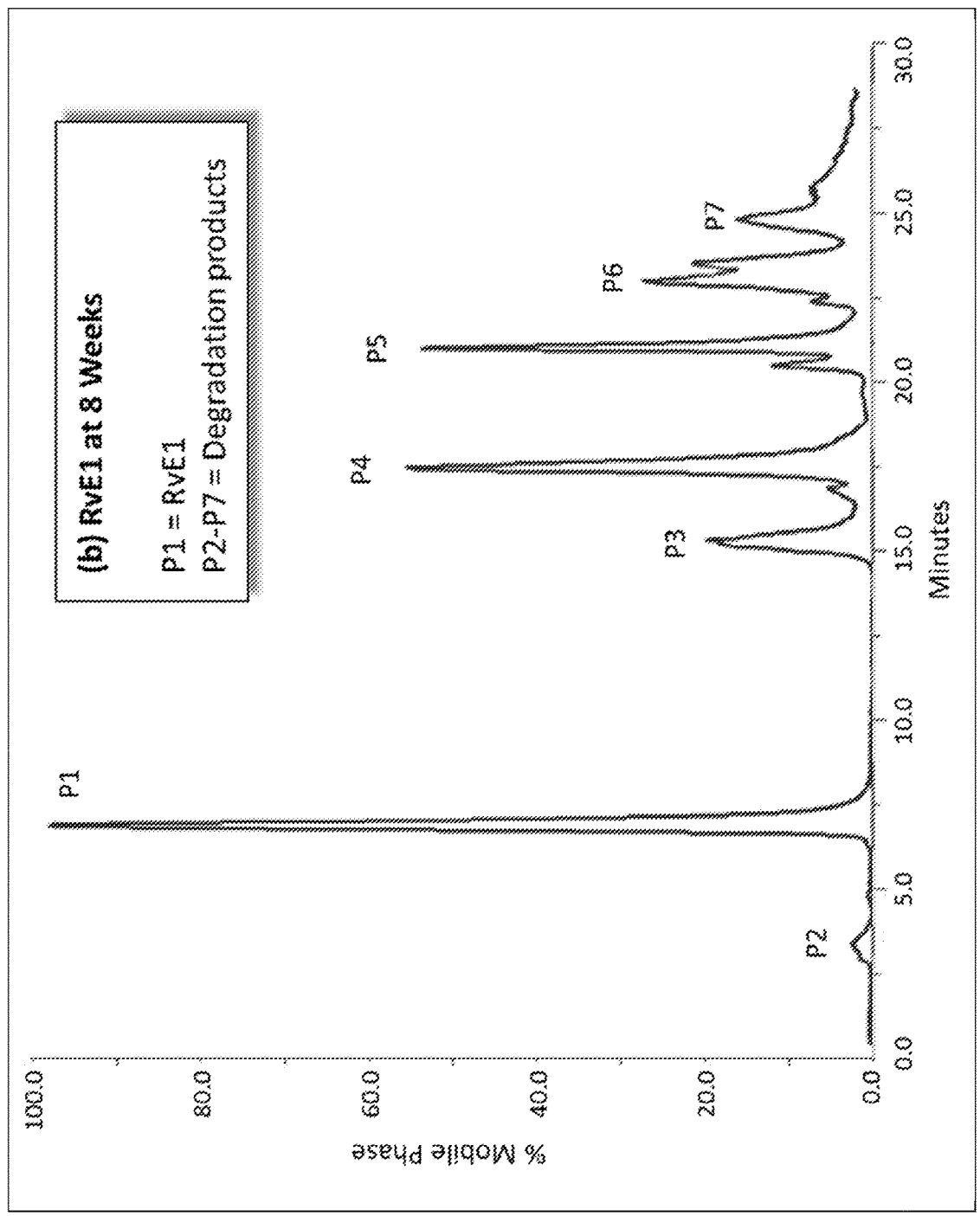

At the initial time point, RvE1 elutes as a single major peak at retention time (rt) 7 minutes, with minor degradation products at 15 and 17.5 minutes (FIG. 1A). Following 8 weeks exposure to the test conditions described above, RvE1 had extensively degraded, as indicated by the appearance of multiple peaks corresponding to degradation products at rt 15 through 25 minutes (FIG. 1B).

Figure 2A:
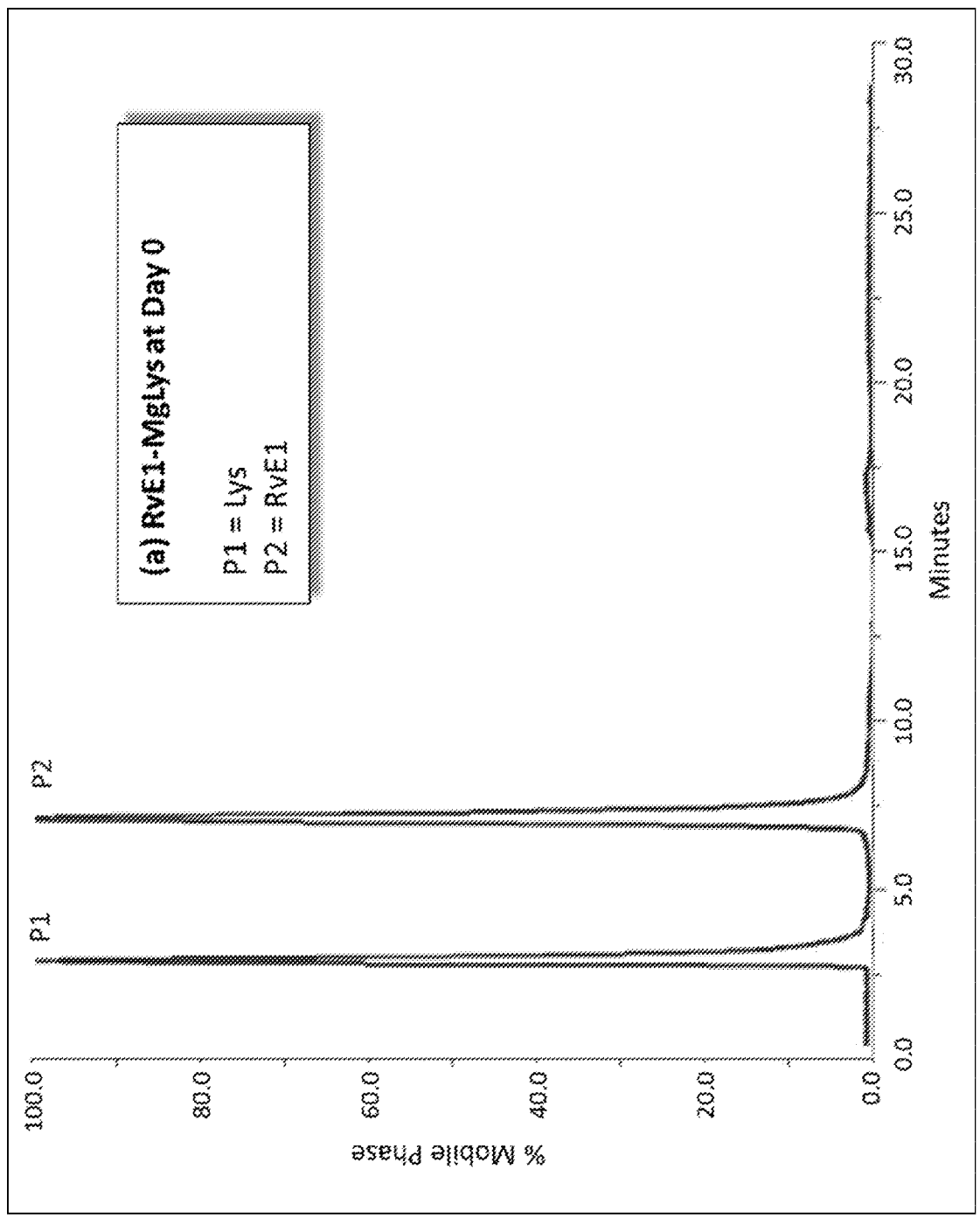
FIG. 2A,B: Chemical Stability of RvE1 Mg-di-lysinate. A, HPLC trace of RvE1 Mg-di-lysinate at time zero. B, HPLC trace of RvE1 Mg-di-lysinate at 8 weeks.
Figure 2B:
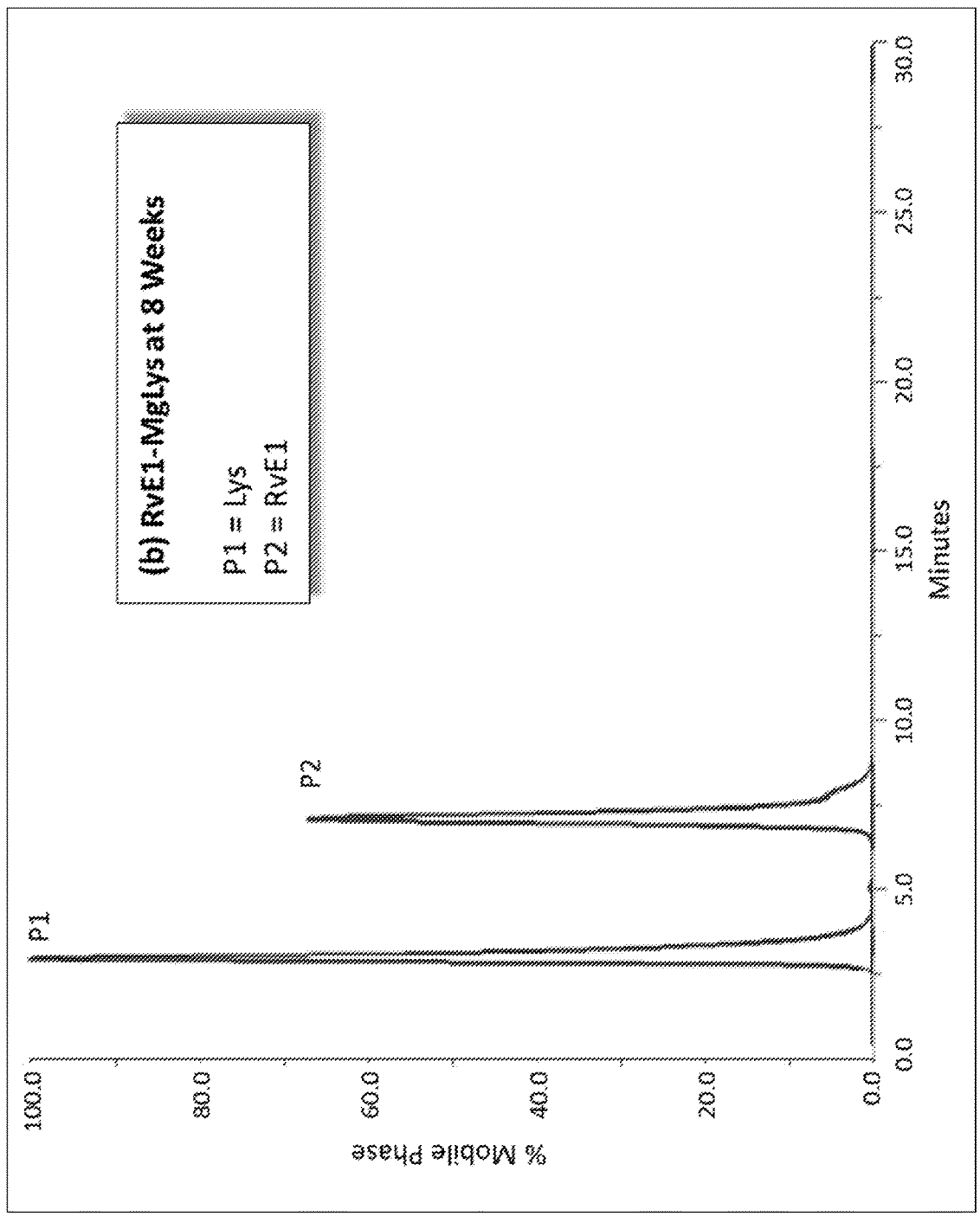

In contrast, under the same conditions, RvE1 magnesium (Mg) di-lysinate did not exhibit any degradation products. At the initial time point, RvE1 Mg di-lysinate elutes as two peaks representing its dissociation into RvE1 (at rt 7 min.) and lysine (at rt 3 min.) from the RvE1 Mg di-lysinate salt (compare FIGS. 2A and 2B).

Figure 3B:
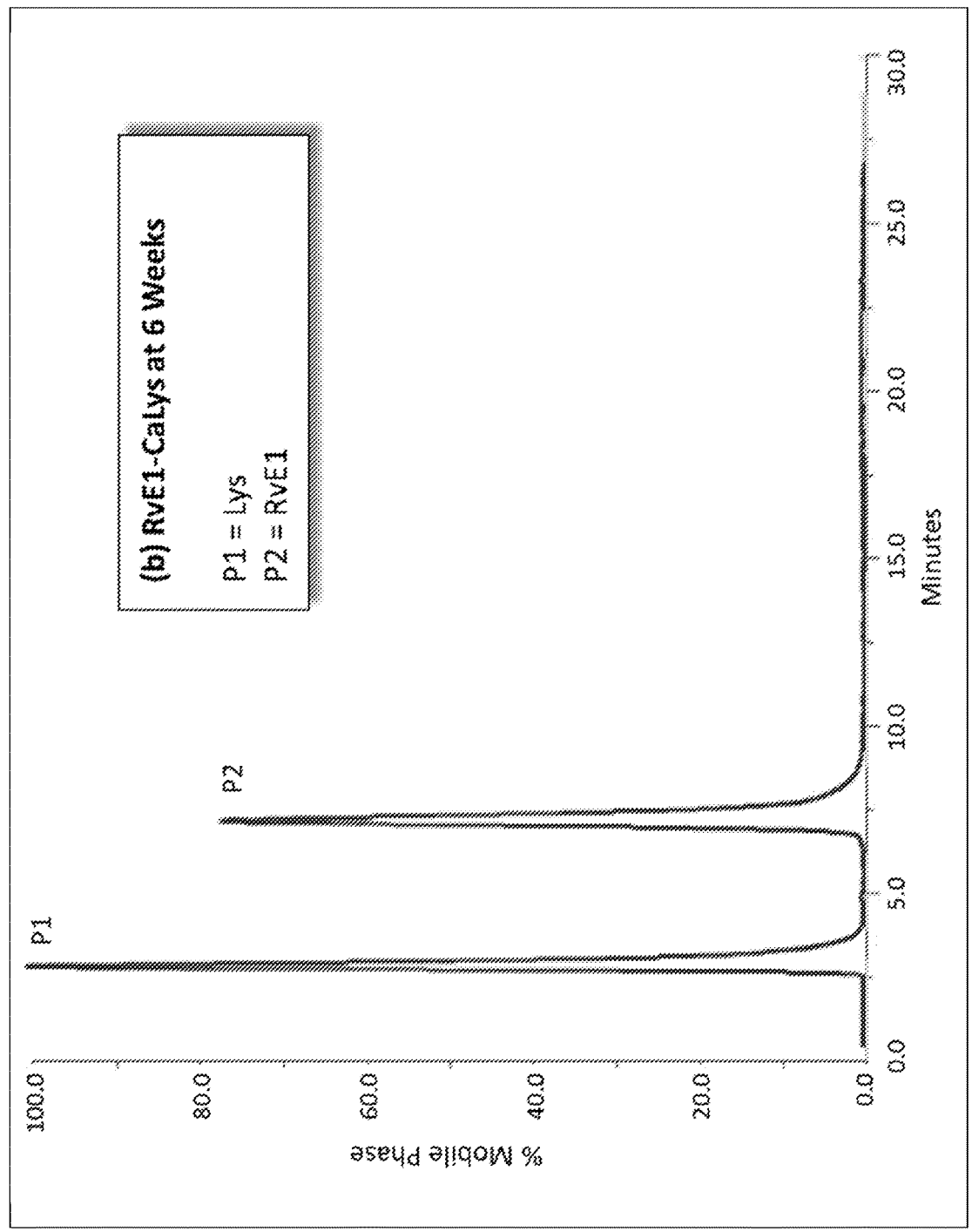
FIG. 3A,B: Chemical Stability of RvE1 Ca-di-lysinate. A, HPLC trace of RvE1 Ca-di-lysinate at time zero. B, HPLC trace of RvE1 Ca-di-lysinate at 6 weeks.

Similarly, the calcium (Ca) di-lysinate salt form of RvE1 exhibited the same enhanced stability profile observed for the Mg di-lysinate salt form (compare FIG. 3A to 3B). In this example and as was observed for the Mg di-lysinate salt, at both the initial time point and after 6 weeks of exposure to the test conditions, the compound elutes as two peaks, RvE1 (rt 7 min) and lysine (rt 3 min) reflecting dissociation of the RvE1 Ca di-lysinate salt. No additional peaks corresponding to degradation products were observed.

Figure 4A:
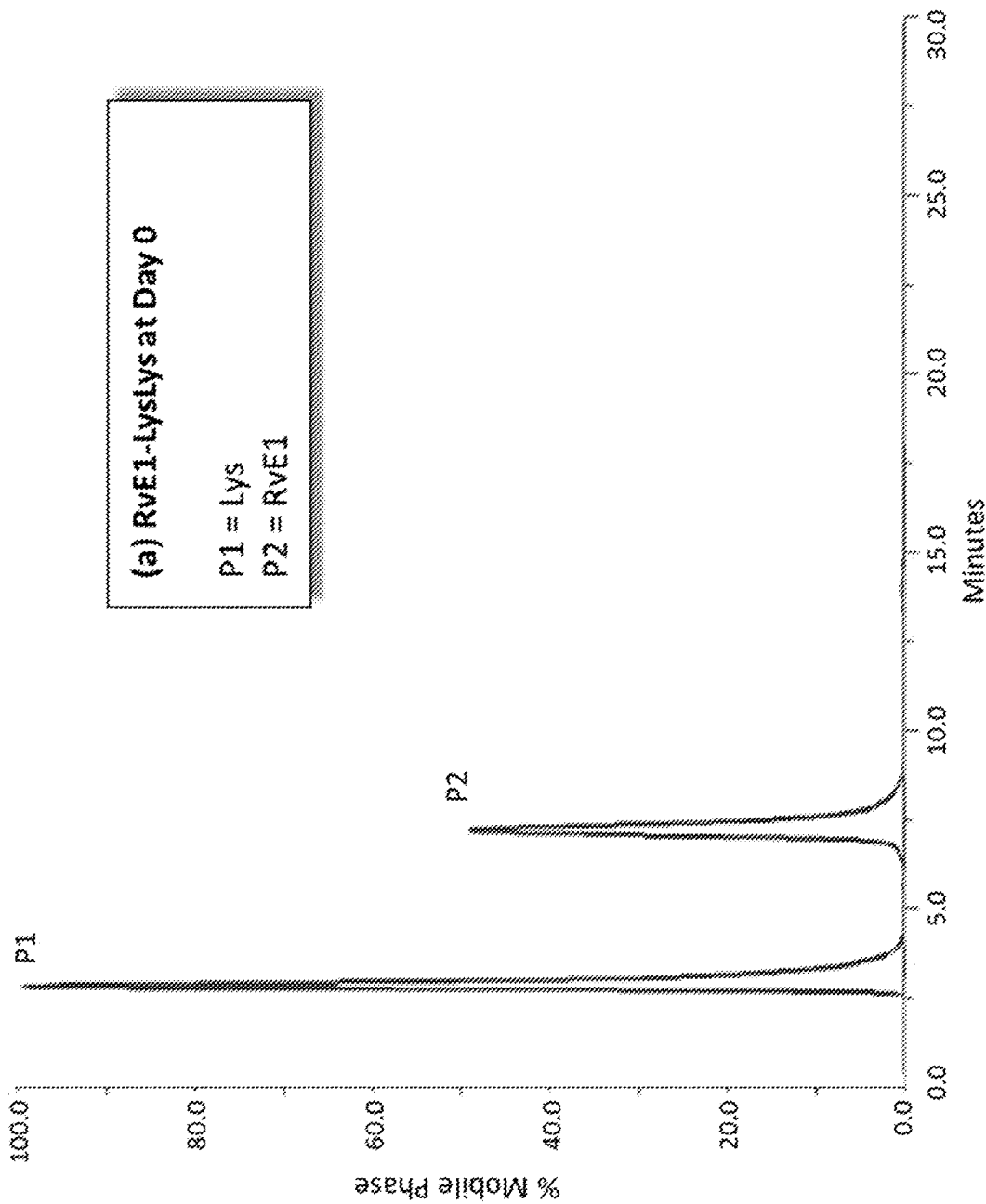
FIG. 4A,B: Chemical Stability of RvE1 lysyl lysine. A, HPLC trace of RvE1 lysyl lysine at time zero. B, HPLC trace of RvE1 lysyl lysine at 8-weeks.
Figure 4B:
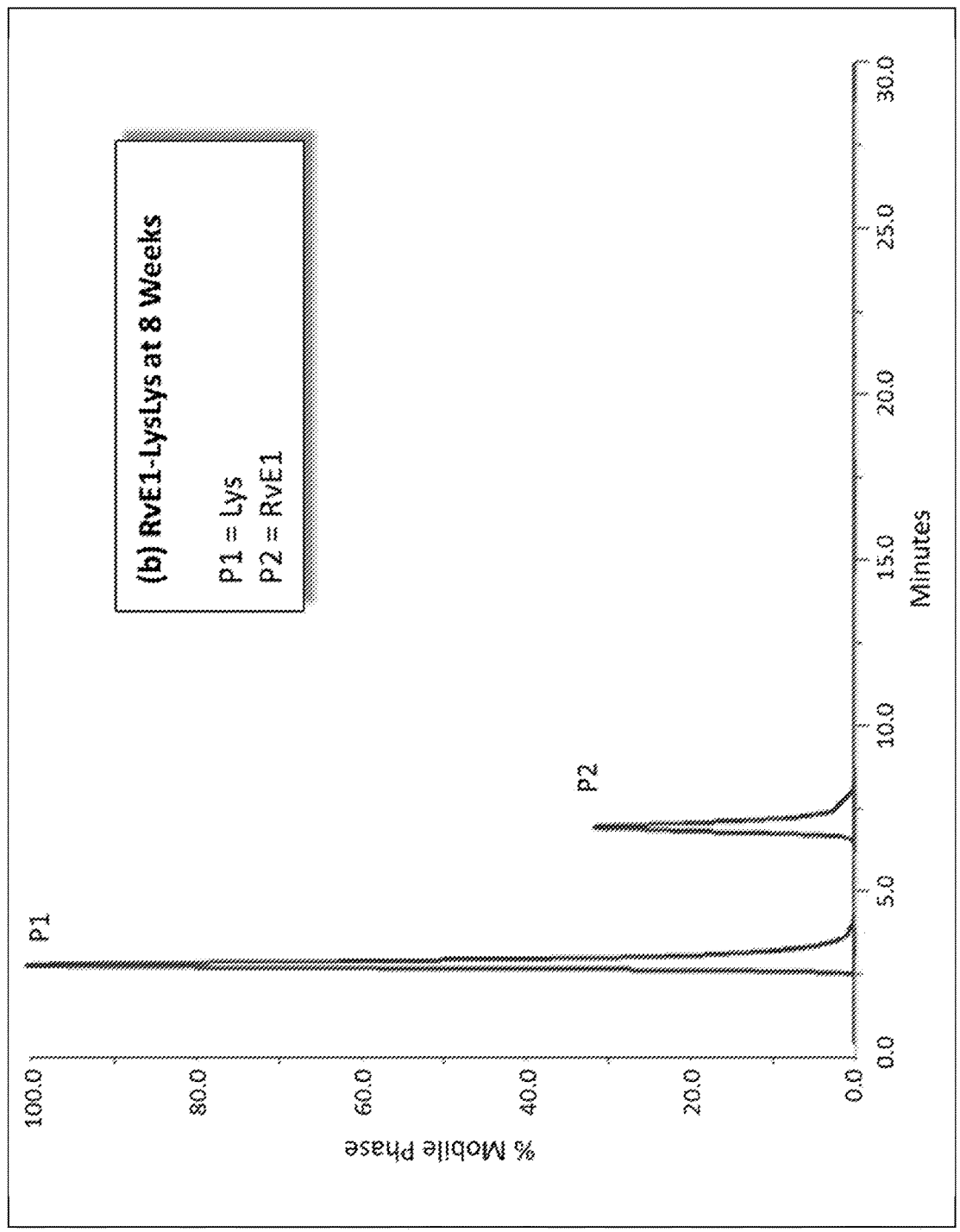

A representative compound of Formula I, a lysyl lysine (lys lys) salt form of RvE1, showed the same enhanced stability. Like the compounds of Formula IV, at the initial time point, RvE1 lys lys elutes as two peaks, RvE1 (rt 7 min) and lysine (rt 3 min) (FIG. 4A). After 8 weeks under the test conditions described above, these same two peaks are present, without degradation products (FIG. 4B).

In summary, these results show that the free acid form of RvE1 experienced significant degradation during 8 weeks of exposure to the test conditions (compare FIG. 1A to 1B), while representative compounds of Formulas I and IV having RvE1 as the SPM component showed no degradation of the SPM under the same conditions for the same or similar periods of time. These results indicate that compounds of Formulas I and IV can significantly improve the stability of the free acid form of an SPM that is otherwise unstable under the conditions used here.

Example 16: RvE1-Mg-Di-Lysinate Shows Efficacy in Pre-Clinical Mouse Model of Colitis A representative compound of Formula IV, RvE1-Mg-di-lysinate, was tested for efficacy in the dextran sulfate sodium (DSS) mouse model of colitis. In this model system, DSS exposure disrupts intestinal barrier function, stimulating local inflammation and inducing a colitis phenotype that mimics the clinical and histopathological features of IBD. See e.g., Laroui H et al. Dextran sodium sulfate (DSS) induces colitis in mice by forming nano-lipocomplexes with medium-chain-length fatty acids in the colon. PLoS ONE. 2012; 7(3):e32084.

In the present study, 8-week old male C57Bl/6J mice were randomized by weight to three experimental groups and administered 2% DSS (w/v) in drinking water for 7 days. Beginning on study day 0, animals were administered either RvE1-Mg-di-lysinate (RvE1-Mg-Lys), an equimolar dose of RvE1, or vehicle via once-daily oral gavage. Disease activity was assessed daily using an established Disease Activity Index (DAI). See e.g., Morin C, Blier P U, Fortin S. MAG-EPA reduces severity of DSS-induced colitis in rats. Am J Physiol Gastrointest Liver Physiol. 2016; 310(10): G808-21. All animals were sacrificed after 7 days of DSS exposure and colons and spleens were harvested. Gross morphological markers of disease activity, including colon length and normalized spleen weight (mg per g body weight) were assessed.

As shown in Table 6, RvE1-Mg-Lys treatment was associated with a statistically significant reduction in DAI relative to vehicle control on study day 7, indicating reduced clinical signs of colitis. In addition, RvE1-Mg-Lys was associated with a statistically significant increase in colon length and a trend towards reduced normalized spleen weight, suggesting reduced intestinal and systemic inflammation.

TABLE 6

RvE1-Mg-di-lysinate shows efficacy in pre-clinical mouse model of colitis

|  | Control (n = 12) | RvE1-Mg-Lys (n = 12) | RvE1 (n = 10) |
| --- | --- | --- | --- |
| Disease Activity Index | 7.2 ± 1.9 | 4.8 ± 1.3*** | 5.6 ± 1.1** |
| Colon Length (mm) | 68.8 ± 7.5 | 77.1 ± 7.8* | 75.2 ± 7.6 |
| Normalized Spleen Weight (mg/g BW) | 4.5 ± 1.9 | 3.6 ± 0.9 | 3.9 ± 0.7 |

All statistical comparisons made versus control using one-way ANOVA.
\* = P <0.05,
\*\* = P <0.01,
\*\*\* = p <0.001

These data demonstrate that RvE1-Mg-Lys is orally active and has therapeutic efficacy in a well-established IBD animal model. Interestingly, the improvements in DAI, colon length, and normalized spleen weight associated with RvE1-Mg-Lys were greater than those associated with an equimolar dose of RvE1 itself. Although these differences did not achieve statistical significance, they suggest that the RvE1-Mg-Lys may have increased biological activity compared to RvE1 itself.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating a pulmonary disease or disorder in a subject in need of such treatment, the method comprising administering to the subject a pharmaceutical composition comprising a compound of Formula IV, or an enantiomer, polymorph, solvate, or hydrate thereof, and a carrier:

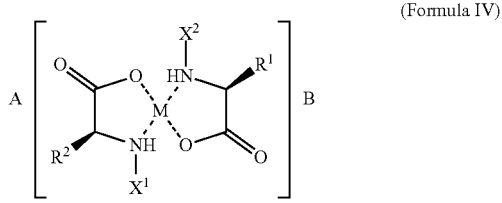

(Formula IV)

wherein

M is a divalent metal selected from magnesium ($Mg^{2+}$), calcium ($Ca^{2+}$), and zinc ($Zn^{2+}$), A and B are each independently an SPM molecule selected from a D series resolvin and an E series resolvin, A and B may be the same or different, either A or B, but not both, may be absent, $R^1$ and $R^2$ are each independently selected from —$(CH_2)_3$—$Y^1$, and —$(CH_2)_4$—$Y^2$, where $Y^1$ and $Y^2$ are each selected from a positively charged primary amine, a positively charged secondary amine, a positively charged tertiary amine, and a positively charged guanidine, $X^1$ and $X^2$ are each independently selected from H and CO—Z and Z is a peptide comprising 1 to 5 amino acids.

2. The method of claim 1, wherein M is selected from magnesium ($Mg^{2+}$) or calcium ($Ca^{2+}$).

3. The method of claim 1, wherein $R^1$ and $R^2$ are independently selected from —$(CH_2)_3$—$Y^1$, and —$(CH_2)_4$—$Y^2$, and $Y^1$ and $Y^2$ are each as set forth in claim 1.

4. The method of claim 3, wherein $X^1$ and $X^2$ are each H.

5. The method of claim 4, wherein $R^1$ and $R^2$ are each —$(CH_2)_4$—$Y^2$ and $Y^2$ is —$NH_3^+$.

6. The method of claim 5, wherein A and B are each independently an E series resolvin selected from the group consisting of resolvin E1 (RvE1), resolvin E2 (RvE2), resolvin E3 (RvE3), aspirin-triggered RvE1 (AT-RvE1), AT-RvE2, and AT-RvE3.

7. The method of claim 6, wherein A and B are the same.

8. The method of claim 7, wherein A and B are RvE1.

9. The method of claim 1, wherein M is magnesium ($Mg^{2+}$), $R^1$ and $R^2$ are each —$(CH_2)_4$—$Y^2$ and $Y^2$ is —$NH_3^+$, $X^1$ and $X^2$ are each H, and A and B are RvE1, which compound is referred to as *bis* RvE1 Mg-di-lysinate.

10. The method of claim 5, wherein A and B are each independently a D series resolvin selected from the group consisting of resolvin D1 (RvD1), resolvin D2 (RvD2), resolvin D3 (RvD3), resolvin D4 (RvD4), resolvin D5 (RvD5), resolvin D6 (RvD6), aspirin-triggered RvD1 (AT-RvD1), AT-RvD2, AT-RvD3, AT-RvD4, AT-RvD5 and AT-RvD6.

11. The method of claim 10, wherein A and B are the same.

12. The method of claim 11, wherein A and B are RvD1.

13. The method of claim 1, wherein M is magnesium ($Mg^{2+}$), $R^1$ and $R^2$ are each —$(CH_2)_4$—$Y^2$ and $Y^2$ is —$NH_3^+$, $X^1$ and $X^2$ are each H, and A and B are RvD1, which compound is referred to as bis RvD1 Mg-di-lysinate.

14. The method of claim 1, wherein the pulmonary disease or disorder is selected from pulmonary inflammation, bronchopulmonary dysplasia, cystic fibrosis, allergic airway response, acute lung injury, lung injury, idiopathic pulmonary fibrosis, bacterial pneumonia, and cigarette smoke-induced lung inflammation.

15. The method of claim 6 or 10, wherein the pulmonary disease or disorder is selected from pulmonary inflammation, bronchopulmonary dysplasia, cystic fibrosis, allergic airway response, acute lung injury, lung injury, idiopathic pulmonary fibrosis, bacterial pneumonia, and cigarette smoke-induced lung inflammation.

16. The method of claim 9 or 13, wherein the pulmonary disease or disorder is selected from pulmonary inflammation, bronchopulmonary dysplasia, cystic fibrosis, allergic airway response, acute lung injury, lung injury, idiopathic pulmonary fibrosis, bacterial pneumonia, and cigarette smoke-induced lung inflammation.

17. The method of claim 14, wherein the pulmonary disease or disorder is pulmonary inflammation.

18. The method of claim 14, wherein the pulmonary disease or disorder is acute lung injury.

19. The method of claim 14, wherein the pulmonary disease or disorder is bacterial pneumonia.

20. The method of claim 14, wherein the pulmonary disease or disorder is bronchopulmonary dysplasia.

21. The method of claim 14, wherein the pulmonary disease or disorder is cystic fibrosis.

22. The method of claim 14, wherein the pulmonary disease or disorder is idiopathic pulmonary fibrosis.

23. The method of claim 14, wherein the subject is human.

24. The method of claim 15, wherein the pulmonary disease or disorder is pulmonary inflammation.

25. The method of claim 15, wherein the pulmonary disease or disorder is acute lung injury.

26. The method of claim 15, wherein the pulmonary disease or disorder is bacterial pneumonia.

27. The method of claim 15, wherein the pulmonary disease or disorder is bronchopulmonary dysplasia.

28. The method of claim 15, wherein the pulmonary disease or disorder is cystic fibrosis.

29. The method of claim 15, wherein the pulmonary disease or disorder is idiopathic pulmonary fibrosis.

30. The method of claim 15, wherein the subject is human.

31. The method of claim 1, wherein the pharmaceutical composition is a parenteral dosage form.

32. The method of claim 31, wherein the parenteral dosage form is selected from the group consisting of an intravenous dosage form, an intra-arterial dosage form, or an intramuscular dosage form.

33. The method of claim 1, wherein the pharmaceutical composition is an intravenous dosage form.

* * * * *